United States Patent
Acemoglu et al.

(10) Patent No.: US 9,278,997 B2
(45) Date of Patent: *Mar. 8, 2016

(54) PROCESSES FOR THE MANUFACTURE OF MACROCYCLIC DEPSIPEPTIDES AND NEW INTERMEDIATES

(71) Applicants: Murat Acemoglu, Basel (CH); Heribert Hellstern, Heitersheim (DE); Felix Kollmer, Riehen (CH); John Lopez, Liestal (CH); Robert Schreiber, Birsfelden (CH); Christian Sprecher, Rafz (CH); Hans Stettler, Allschwil (CH)

(72) Inventors: Murat Acemoglu, Basel (CH); Heribert Hellstern, Heitersheim (DE); Felix Kollmer, Riehen (CH); John Lopez, Liestal (CH); Robert Schreiber, Birsfelden (CH); Christian Sprecher, Rafz (CH); Hans Stettler, Allschwil (CH)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/082,315

(22) Filed: Nov. 18, 2013

(65) Prior Publication Data
US 2014/0080995 A1    Mar. 20, 2014

Related U.S. Application Data

(62) Division of application No. 13/449,937, filed on Apr. 18, 2012, now Pat. No. 8,614,289.

(60) Provisional application No. 61/477,319, filed on Apr. 20, 2011.

(51) Int. Cl.
| | |
|---|---|
| A61K 38/12 | (2006.01) |
| C07K 5/00 | (2006.01) |
| C07K 7/00 | (2006.01) |
| C07K 16/00 | (2006.01) |
| C07K 17/00 | (2006.01) |
| C07K 11/02 | (2006.01) |
| C07K 7/06 | (2006.01) |
| C07K 11/00 | (2006.01) |
| A61K 38/00 | (2006.01) |

(52) U.S. Cl.
CPC . *C07K 11/02* (2013.01); *C07K 7/06* (2013.01); *C07K 11/00* (2013.01); *A61K 38/00* (2013.01)

(58) Field of Classification Search
CPC ........... C07K 11/02; C07K 7/06; C07K 11/00
See application file for complete search history.

(56) References Cited

U.S. PATENT DOCUMENTS

| | | | |
|---|---|---|---|
| 5,595,756 A | 1/1997 | Bally et al. | |
| 6,630,569 B1 | 10/2003 | Jeschke et al. | |
| 8,178,650 B2 | 5/2012 | Krastel et al. | |
| 8,415,305 B2 | 4/2013 | Krastel et al. | |
| 8,614,289 B2 | 12/2013 | Acemoglu et al. | |
| 8,680,054 B2 | 3/2014 | Haug | |
| 2004/0110228 A1 | 6/2004 | McAlpine et al. | |
| 2005/0014684 A1 | 1/2005 | Palomera et al. | |
| 2009/0036487 A1 | 2/2009 | Field et al. | |
| 2009/0186042 A1 | 7/2009 | Johnston et al. | |
| 2010/0209376 A1 | 8/2010 | Richters et al. | |
| 2012/0064136 A1 | 3/2012 | Baker et al. | |
| 2012/0196790 A1 | 8/2012 | Krastel et al. | |
| 2013/0017226 A1 | 1/2013 | Park | |
| 2013/0172267 A1 | 7/2013 | Krastel et al. | |
| 2014/0100353 A1 | 4/2014 | Acemoglu et al. | |
| 2014/0100355 A1 | 4/2014 | Acemoglu et al. | |

FOREIGN PATENT DOCUMENTS

| | | |
|---|---|---|
| EP | 0 052 200 A1 | 9/1981 |
| JP | 2000154198 A | 6/2000 |
| WO | 9534558 A1 | 12/1995 |
| WO | 2004108139 A2 | 12/2004 |
| WO | 2005075667 A1 | 8/2005 |
| WO | 2009/022182 A1 | 2/2009 |
| WO | 2009024527 A1 | 2/2009 |
| WO | 2009024528 A1 | 2/2009 |
| WO | 2011003858 A2 | 1/2011 |
| WO | 2012035468 A2 | 3/2012 |

(Continued)

OTHER PUBLICATIONS

Yokokawa et al., Tetrahedron Letters, 2001, 42, 5903-5908.*

(Continued)

*Primary Examiner* — James H Alstrum Acevedo
*Assistant Examiner* — Kaipeen Yang
(74) *Attorney, Agent, or Firm* — Sophie Binet Cross

(57) ABSTRACT

The invention relates to a method or process for the chemical manufacture of depsipeptides of the formula I,

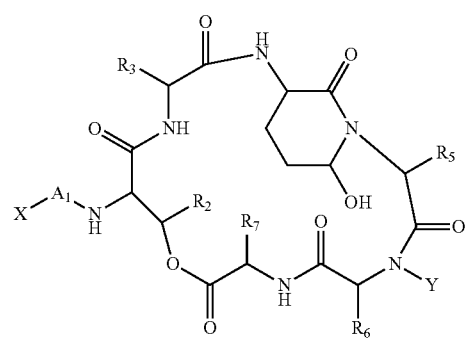

wherein the symbols have the meaning defined in the description, to new intermediates and their manufacture, as well as related invention embodiments.

12 Claims, No Drawings

(56) References Cited

FOREIGN PATENT DOCUMENTS

| WO | 2012103035 A1 | 8/2012 |
|---|---|---|
| WO | 2012103038 A2 | 8/2012 |
| WO | 2015/155676 A1 | 10/2015 |

OTHER PUBLICATIONS

Isidro-Llobet et al., Chem. Rev., 2009, 109, 2455-2504.*
Technical Note 524, Biotage, 2004, p. 1-6.*
Matsuda et al., Tennen Yuki Kagobutsu Toronkai Koen Yoshishu 35:654-661, (1993).
Elert et al, 'Cyanopeptolin 954, a Chlorine-Containing Chymotrypsin Inhibitor of *Microcystis aeruginosa* NIVA Cya 43', J Nat Prod 68(9): 1324-1327 (2005).
Yokokawa et. al., 'Synthetic studies towards 3-Amino-6-hydroxy-2-piperidone (Ahp)-Containing Cyclic Depsipeptides', Peptide Science 38:33-36 (2001).
Johannesson et al., "Angiotensin II Analogues Encompassing 5, 9- and 5,10-Fused ThiazabicycloalkaneTripeptide Mimetics", J. Med. Chem 42(22):4524-4537 ( Nov. 1, 1999).
Yokokawa et. al., Synthetic studies of micropeptin T-20, a novel 3-amino-6-hydroxy-2-piperidone (AHP)-containing cyclic depsipeptide, Tetrahedron Letters 42(34): 5903-5908 (2001).
Yokokawa et. al., Total synthesis of sonamide A, an Ahp (3-amino-6-hydroxy-2-piperidone)-containing cyclic depsipeptide, Tetrahedron Letters 43(48):8673-8677 (2002).
Yokokawa et. al., Synthetic studies of the cyclic depsipeptides bearing the 3-amino-6-hydroxy-2-piperidinone (Ahp) unit. Total synthesis of the proposed structure of micropeptin T-20, Tetrahedron 61(6):1459-1480 (2005).
Itou et al, "Oscillapeptins A to F, Serine Protease Inhibitors from the Three Strains of Oscillatoria agardhii," Tetrahedron 55(22):6871-6882 (1999).
Namikoshi et al., "Bioactive compounds produced by cyanobacteria," J Ind Microbiol Biotech 17(5-6):373-384 (1996).
McDonough et al, "New Structural Insights into the Inhibition of Serine Proteases by Cyclic Peptides from Bacteria," Chem & Biol 10(10):898-900 (Oct. 2003).
Franzke et al, "Antileukoprotease Inhibits Stratum Corneum Chymotryptic Enzyme," J Biol Chem 271(36):21886-21890 (1996).
Harada et al, "Co-production of Microcystins and Aeruginopeptins by Natural Cyanobactieral Bloom," Environ Toxicol 16:298-305 (2001).
Grach et al, "Protease inhibitors from a Slovenian Lake Bled toxic waterbloom of the cyanobacterium *Planktothrix rubescens*," Tetrahedron 59(42):8329-8336 (2003).
Matern et al., "Binding Structure of Elastaste Inhibitor Scyptolin A," Chemistry & Biology 10:997-1001 (Oct. 2003).
Nakanishi et al, "Structure of Porcine Pancreatic Elastase Compled with FR901277, a Novel Macrocyclic Inhibitor of Elastases, at 1.6 A Resolution," Biopolymers 53(5):434-445 (2000).
Hansson et al., "Epidermal Overexpression of Stratum Corneum Chymotryptic Enzyme in Mice: A Model for Chronic Itchy Dermatitis," J. Invest. Dermatol. 118(3):444-449 (2002).
Hachem et al; "Serine Protease Activity and Residual LEKTI Expression Determine Phenotype in Netherton Syndrome"; Journal of Investigative Dermatology, 126:1609-1621 (2006).
Hiemstra, "Novel roles of protease inhibitors in infection and inflammation," Biochem Soc Trans 30(2): 116-120 (2002).
Kunze et al, <<Chondramides A-D, New Antifunal and Cytostatic Depsipeptides from *Chondromyces crocatus*,<< J Antibiot 48(11):1262-1266 (Nov. 1995).
Ekholm and Egelrud "Stratum corneum chymotryptic enzyme in psoriasis," Arch Dermatol Res 291(4):195-200 (1999).
Vasilopoulos et al. "Genetic Association Between an AACC Insertion in the 3'UTR of the Stratum Corneum Chymotryptic Enzyme Gene and Atopic Dermatitis," J. Invest. Dermatol. 123:62-66 (2004).
Banker et al, "Inhibitors of Serine Protease from a Waterbloom of the Cyanobacterium microcystis sp.," Tetrahedron 55(35): 10835-10844 (1999).

Bonjouklian et al., "A90720A, A Serine Protease Inhibitor Isolated From a Terrestrial Blue-Green Alga *Microchaete loktakensis*," Tetrahedron 52(2):395-404 (1996).
Reshef and Carmeli, "Protease inhibitors from a water bloom of the cyanobacterium *Microcystis aeruginosa*," Tetrahedron 57(14):2885-2894 (2001).
Fairlie et al., "Conformational Selection of Inhibitors and Substrates by Proteolytic Enzymes: Implications for Drug Design and Polypeptide Processing," J Med Chem 43(7): 1271-1281 (2000).
Matthew et al., <<Lyngbyastatin 4, a Dolastatin 13 Analogue with Elastase and Chymotrypsin Activity from the Marine Cyanobacterium Lyngbya confervoides, J Nat Prod 70(1):124-127 (2007).
Egelrud, Torbjorn, "Purification and Preliminary Characterization of Stratum Corneum Chymotryptic Enzyme: A Proteinase That May Be Involved in Desquamation," J Invest Dermatol 101(2):200-204 (1993).
Tsukamoto et.al.,MicrocystilideA: A Novel Cell-Differentiation-Prompting Depsipeptide from *Microcystis aeruginosa* NO-15-1840, J. Am. Chem. Soc. 115:11046-11047 (1993).
Harada et al., Application of D,L-FDLA Derivatization to Determine of Absolute Configuration of Constituent Amino Acids in Peptide by Advanced Marfey's Method,Tetrahedron Letters 37(17):3001-3004 (1996).
Fujii et al., "Development of a Method for Determining the Absolute Configuration of Constituent Amino Acids in Peptides Using LC/MS," Tennen Yuki Kagobutsu Toronkai Koen Yoshishu 39:223-228 (1997).
Cochrane et. al., 'Total Synthesis and Assignment of the Side Chain Stereochemistry of LI-F04a: An Antimicrobial Cyclic Depsipeptide', Organic Letters 12(15):3394-3397 (2010).
Seo and Lim, 'Total Synthesis of Halicylindramide A,' Journal of Organic Chemistry 74:906-909 (2009).
Okumura et. al., 'Homotyrosine-Containing Cyanopeptolins 880 and 960 and Anabaenopeptins 908 and 915 from Planktothrix agardhii CYA 126/8', J Nat Prod 72:172-176 (2009).
Ishida et. al., Micropeptins 88-A to 88-F, Chymotrypsin Inhibitors from the Cyanobacterium *Microcystis aeruginosa* (NIES-88), Tetrahedron 54(21):5545-5556 (1998).
Zainuddin et. al., 'Cyclic Depsipeptides, Ichthyopeptins A and B, from Microcystis ichthyoblabe', J. Nat. Prod 70:1084-1088 (2007).
Olsen et al.,Synthesis of Nalpha, Nbeta-protected Ndelta-Hydroxy-L-ornitine from L-Glutamic Acid, J. Org. Chem. 49:3527-3534 (1984).
Yoshiya et al., "O-Acyl isopeptide method for peptide synthesis: synthesis of forty kinds of "O-acyl isodipeptide unit" Boc-Ser/Thr(Fmoc-Xaa)-OH," Organic & Biomolecular Chemistry 5:1720-1730 (2007).
Stolze et al., "Solid phase total synthesis of the 3-amino-6-hydroxy-2-piperidone (Ahp) cyclodepsipeptide and protease inhibitor Symplocamide A", Chemical Communications 46:8857-8859 (2010).
Stolze et al., "Development of a Solid-Phase Approach to the Natural Product Class of Ahp-Containing Cyclodepsipeptides", European Journal of Organic Chemistry 2012:1616-1625 (2012).
Stawikowski and Cudic, "A novel strategy for the solid-phase synthesis of cyclic lipodepsipeptides", Tetrahedron Letters 47:8587-8590 (2006).
Bourel-Bonnet et al., "Solid-Phase Total Synthesis of Kahalalide A and Related Analogues", Journal of Medicinal Chemistry 48:1330-1335 (2005).
Lautenschläger et al., "Fettstoffe—die Basis der Hautpflege" Kosmetische Praxis 6:6-8 (2003).
Pena et. al., "Structural Rheology of a Model Ointment", Pharmaceutical Research 11(6)875-881 (1994).
Bos et. al., "The 500 Dalton rule for the skin penetration of chemical compounds and drugs," Experimental Dermatology 9:165-169 (2000).
Benson et. al. "Proteins and Peptides: Strategies for Delivery to and Across the Skin", Journal of Pharmaceutical Sciences, vol. 97, 3591-3610 (2008).
Berendsen, Herman, "A Glimpse of the Holy Grail?" Science 282:642-643 (Oct. 23, 1998).

(56) References Cited

OTHER PUBLICATIONS

Rudinger J, "Characteristics of the amino acids as components of a peptide hormone sequence," Peptide Hormones, JA Parsons Ed., 1-7 (1976).

Schinzel and Drueckes, "The phosphate recognition site of *Escherichia coli* matodextrin phosphorylase," FEBS 286(1, 2):125-128 (Jul. 1991).

Voet et al, Biochemistry, Second Edition, John Wiley & Sons, Inc, 1995,235-241.

Ngo et al., "Computational Complexity, Protein Structure Prediction and the Levinthal Paradox," The Protein Folding Problem and Tertiary Structure Prediction, K. Merc Jr. and S. Le Grand Edition, 1994, 491-495.

Bradley and Barrick, "Limits of Cooperativity in a Structurally Modular Protein: Response of the Notch Ankyrin Domain to Analogous Alanine Substitutions in Each Repeat," J. Mol. Biol. 324:373-386 (2002).

Sporn and Suh, "Chemoprevention of cancer," Carcinogenesis 21(3):525-530 (2000).

Auerbach et al., "Angiogenesis assays, Problems and pitfalls," Cancer and Metastasis Reviews 19:167-172 (2000).

Gura, T., "Systems for Identifying New Drugs Are Often Faulty," Science 278(5340):1041-1042 (Nov. 7, 1997).

Jain, Rakesh K., "Barriers to Drug Delivery in Solid Tumors," Scientific American 58-65 (Jul. 1994).

Pearce et al., "Failure modes in anticancer drug discovery and development," Cancer Drug Design and Discovery 424-435 (2008).

Custom Peptide Synthesis, "Designing Custom Peptides," SIGMA Genosys, 1-2, (Dec. 16, 2004).

Matsuda et al., Tennen Yuki Kagobutsu Toronkai Koen Yoshishu 35:654-661 (1993).

Dark, Graham, The On-Line Medical Dictionary, World-Wide Web URL: http://cancerweb.nc..ac.uk/omd/index.html, published at the Dept. of Medical Oncology, University of Newcastle upon Tyne, copyright:1997-2003, pp. 1-2.

Residue Definition, http://dictionary.reference.com/browse/residue, (2009), pp. 1-4.

Vishwas S Ganu et al.: "Inactivation of Trypsin-like Proteases by Depsipeptides of p-Guanidinobenzoic Acid", Journal of Medicinal Chemistry, 1981, vol. 24, No. 6, pp. 698-700.

Radau, G.: "Serine proteases inhibiting cyanopeptides", Pharmazie, vol. 55, (2000), pp. 555-560.

\* cited by examiner

PROCESSES FOR THE MANUFACTURE OF MACROCYCLIC DEPSIPEPTIDES AND NEW INTERMEDIATES

This application is a divisional application of U.S. patent application Ser. No. 13/449,937, filed on Apr. 18, 2012, which claims benefit under 35 U.S.C. §119(e) of U.S. Provisional Application No. 61/477,319 filed Apr. 20, 2011; the contents of which is incorporated herein by reference in their entirety.

SUMMARY OF THE INVENTION

The invention relates to a method or process for the manufacture of macrocyclic depsipeptides, to new intermediates and their manufacture, as well as related invention embodiments.

BACKGROUND OF THE INVENTION

Cyclic depsipeptides have numerous uses in pharmacology. As an example, the depsipeptides disclosed in WO2009/024527 are useful for treatment of various diseases. For example, the compound of formula II mentioned in WO2009/024527 is useful for the treatment and prevention of inflammatory and/or hyperproliferative and pruritic skin diseases such as atopic dermatitis, psoriasis, pustular psoriasis, rosacea, keloids, hypertrophic scars, acne, Netherton's syndrome or other pruritic dermatoses such as prurigo nodularis, unspecified itch of the elderly as well as other diseases with epithelial barrier dysfunction such as aged skin.

Nostopeptin BN920, formerly isolated from the cyanobacterium Nostoc, was isolated also from Microcystis. Nostopeptin BN920 inhibited chymotrypsin with an IC50 value of 31 nM (see J. Nat. Prod. 68(9), 1324-7 (2005)).

These compounds can be produced by fermentation (using chondromyces croactus, myxobacteria) along with other depsipeptides comprising the so-called ahp-substructure (ahp: 3-amino-6-hydroxy-piperidin-2-one) and the corresponding dehydro-ahp substructure (dehydro-ahp: 3-amino-3,4-dihydro-1H-pyridin-2-one), also called "dehydrate" herein, respectively. Therefore, the yield of fermentation with regard to any single of these compounds is rather low.

The present invention relates to processes or methods that allow obtaining such cyclic depsipeptides with increased yield and/or in good purity.

In view of the many risks, such as epimerization, tautomerization and the like in the synthesis of a complex molecule with many possible isomers, it has been possible to find a manufacturing process, preferably comprising a mixture of solid phase peptide synthesis and reactions in solution, that allows to produce cyclic depsipeptides of formula I in good yield and/or the required stereoisomerical purity, especially both. It is possible to reduce the amount of by-products, and even to improve yield, by converting such by-products, especially the dehydro-ahp substructure and/or an analogue of the desired ahp-comprising products with a five-membered ring instead of the ahp, into the desired final products. This allows to further increase yield. No synthesis has so far come to our attention making use of solid phase peptide synthesis in this field.

(i/a) In a first embodiment, the invention relates to a method or process for the preparation of a cyclic depsipeptide compound of the formula I,

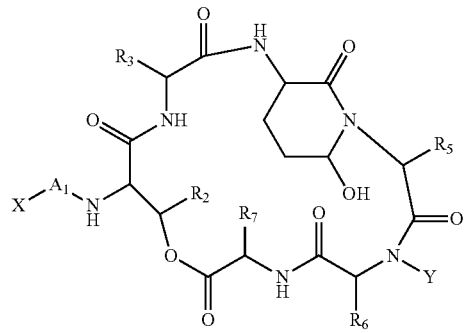

especially of the formula IA

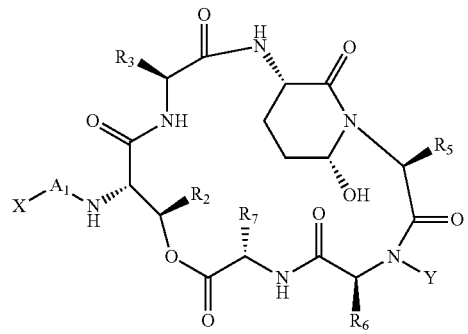

wherein
$A_1$ is a bivalent moiety of an amino acid with a terminal carboxy or carbamoyl group, especially asparagine or glutamine, and is bound at its right hand side in formula I (corresponding to the C-terminus) via a carbonyl (preferably the carbonyl of an α-carboxyl group thereof) to the rest of the molecule; or is $C_{1-8}$-alkanoyl or phosphorylated hydroxy-$C_{1-8}$-alkanoyl;
X is bound via an N of $A_1$ and is acyl, or is absent if $A_1$ is $C_{1-8}$-alkanoyl or phosphorylated hydroxy-$C_{1-8}$-alkanoyl;
$R_2$ is $C_{1-8}$-alkyl, especially methyl;
$R_3$ is the side chain of an amino acid, especially of leucine, isoleucine or valine;
$R_5$ is the side chain of an amino acid, preferably of phenylalanine, leucine, isoleucine or valine;
$R_6$ is the side chain of a hydroxy amino acid, especially of tyrosine;
$R_7$ is the side chain of an amino acid, preferably of the amino acid leucine, isoleucine or valine; and
Y is hydrogen or $C_{1-8}$-alkyl;
or a salt thereof,
said method comprising
selectively deprotecting a compound of the formula II

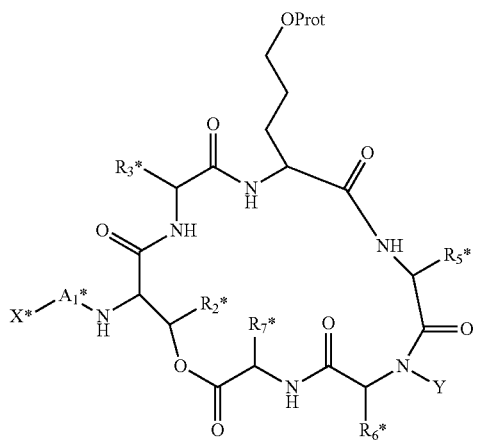

especially of the formula IIA

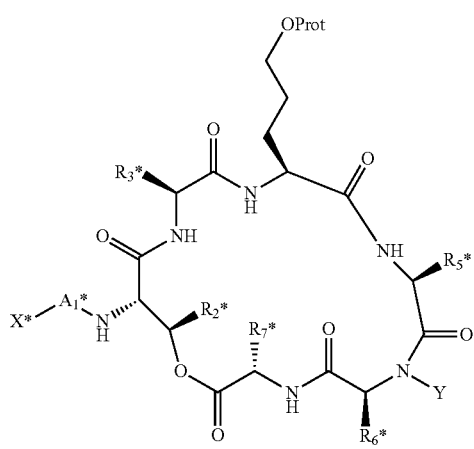

IIA wherein Prot is a protecting group, Y is as defined for a compound of the formula I and X*, A$_1$*, R$_2$*, R$_3$*, R$_5$*, R$_6$*, and R$_7$* correspond to X, A$_1$, R$_2$, R$_3$, R$_5$, R$_6$, and R$_7$ in formula I, respectively, but with the proviso that reactive functional groups on these moieties (such as amino, imino, hydroxy, carboxy, sulfhydryl, amidino, guanidino, O-phosphono (—O—P(=O)(OH)$_2$) are present in protected form at least if they could participate in undesired side reactions, to result in a compound of the formula III,

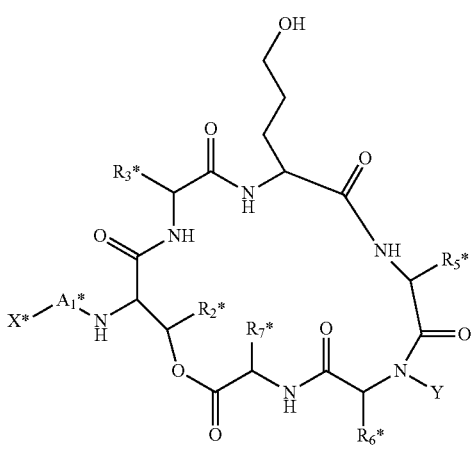

(III)

especially of the formula IIIA,

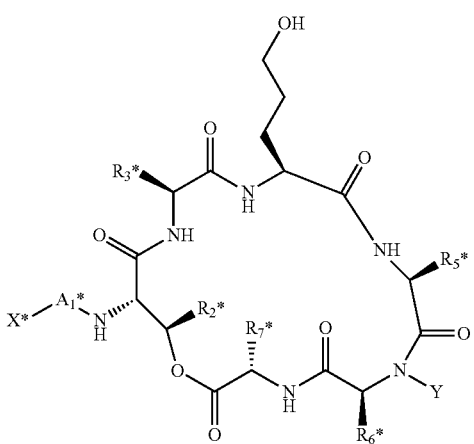

IIIA wherein X*, A$_1$*, R$_2$*, R$_3$*, R$_5$*, R$_6$*, and R$_7$* have the meanings just defined, reacting the free hydroxyl group under oxidizing conditions to form a compound of the formula IV

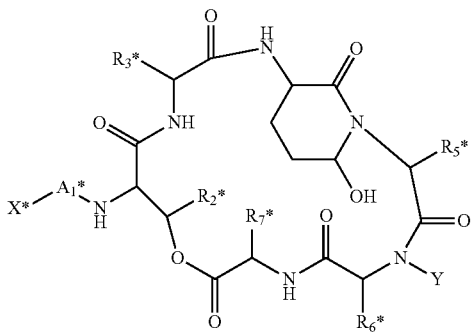

IV especially IVA,

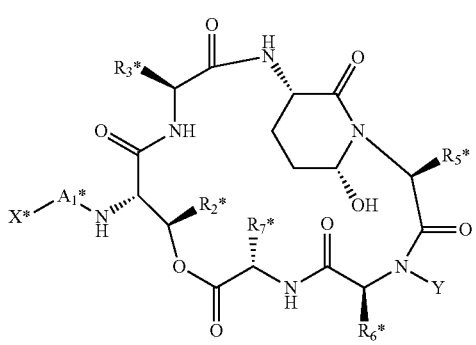

IVA and removing remaining protecting groups to yield a compound of the formula I, or a salt thereof, and, if desired, converting a free compound of the formula I, or especially IA, into a salt, a salt of a compound of the formula I into a different salt of a compound of the formula I, or especially IA, or into the free compound of the formula I, or especially IA, and/or converting a dehydrate analogue and/or five ring analogue of a compound of the formula I, or especially IA, into the corresponding compound of the formula I, or especially IA.

Suitable oxidizing conditions for the oxidation of a compound of the formula III or especially IIIA are usually using IBX in DMSO (J. Org. Chem. 1995, 60, 7272-7276); Pyridinium dichromate or Pyridinium chlorochromate (Tetrahedron Lett. 1979, 5, 399-402); oxalyl chloride, dimethyl sulfoxide and a tertiary amine (J. Peptide Sci. 2006, 12, 140-146), oxoammonium salts (J. Org. Chem. 1985, 50, 1332-1334); alkali hypochlorites catalyzed by oxoammonium salts (J. Org. Chem. 1989, 54, 2970-2972); oxoaminium salts (Tetrahedron Lett. 1988, 29, 5671-5672), RuCl$_2$(PPh$_3$)$_3$ (Tetrahedron Lett. 1981, 22, 1605-1608); TEMPO (1 mol %) in the presence of sodium hypochlorite (Tetrahedron Lett. 1990, 31, 2177-2180); NaIO$_4$, TEMPO, NaBr (Tetrahedron 2006, 62, 8928-8932); SiO$_2$ supported vanadium(IV)oxide and t-BuOOH (Advanced Synthesis & Catalysis 2007, 349, 846-848). Preferably, the reaction is performed with IBX in DMSO or preferably in an inert solvent, such as tetrahydrofuran, in the presence of DMSO, at a temperature between 0-50° C., preferably between 20-25° C.

(ii/a) A further embodiment of the invention refers to the method or process described above, in addition comprising manufacturing the compound of the formula IV or especially IVA by a combination of Solid Phase Peptide Synthesis (especially For synthesis of the precursor XX or especially XXA given below for the oligopeptide precursor of the formula VIII or especially VIIIA given below, or of the oligopeptide precursor of the formula XXIV or especially XXIVA given below for the oligopeptide precursor of the formula XXV or especially XXVA given below) and Solution Phase synthesis (especially from the compounds just mentioned to the final product) from the corresponding starting amino acids and side chain precursors.

(iii/a) Yet a further embodiment of the invention relates to a method or process as described above, further comprising, for the synthesis of a compound of the formula II above, reacting a compound of the formula VI,

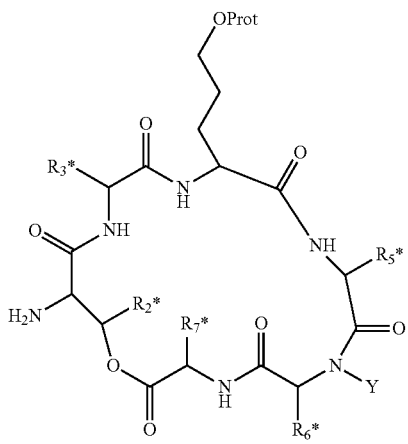

especially VIA,

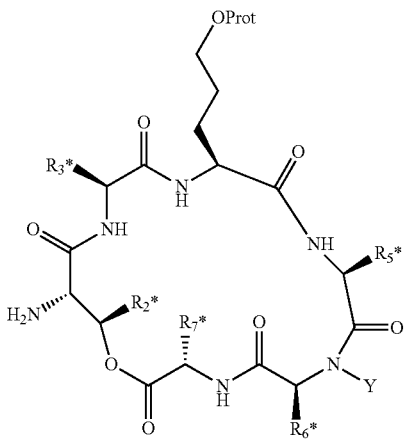

wherein Prot is a protecting group, Y is as defined for a compound of the formula I and $R_2^*$, $R_3^*$, $R_5^*$, $R_6^*$, and $R_7^*$ are as defined for a compound of the formula II above, with an acid of the formula VII

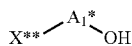

or a reactive derivative thereof,
wherein $X^{**}$ is an amino protecting group or is $X^*$, and wherein $X^*$ and $A_1^*$ are as defined for a compound of the formula II above; and, if $X^{}$ is an amino protecting group, removing said amino protecting group $X^{}$ to yield the derivative of formula II (especially IIA) wherein, instead of $X^*$, H (a hydrogen) is present and coupling the resulting amino group with an acyl group $X^*$ using the corresponding acid $X^*$—OH wherein $X^*$ is as defined for a compound of the formula II defined above, or a reactive derivative thereof.

(iv/a) Another embodiment of the invention relates to the methods or processes described above, especially in the preceding paragraph, further comprising cyclization under lactamization of a linear, that is, not yet cyclic, precursor peptide of the compound of the formula VI, carrying an N-terminal amino group and a C-terminal carboxy group, under reaction conditions that allow for the formation of an amide bond from said amino and said carboxy group, preferably using Solution Phase chemistry.

Lactamizations in solutions are usually carried out at very low concentrations of the substrate in order to avoid oligomerizations and polymerizations. This requires huge amounts of solvents and very large reactors to carry out the reactions. For example, the macrolactamization of an oligopeptide is performed at a concentration of 2 mMols/liter in reference Yokokawa et al., Tetrahedron 2005, 61, 1459-1480. This difficulty can be circumvented by dissolving the tertiary base and the coupling reagent and, in a controlled way adding a solution of the oligopeptide to this solution. The controlled, especially slow, addition of the oligopeptide-solution generates permanently low concentrations of the activated oligopeptide in solution and thus prevents oligomerization and polymerization. The addition rate of the oligopeptide solution can be adjusted according to the reaction rate for the macrocyclization: if the macrocyclization is a fast reaction, the solution of the oligopeptide can be added fast. If the macrocyclization is slow, the addition of the solution must be slow to ensure permanent low concentration of the activated oligopeptide. Thus the controlled addition of the oligopeptide enables to work with much less solvent amounts and still maintaining the concentration of the activated oligopeptide below $10^{-3}$ mM, e.g. in the range from $10^{-4}$ to $10^{-6}$ mM or even lower. This variant of controlled addition of the oligopeptide to the coupling reagent solution is an embodiment of the invention.

(v/a) In yet a further embodiment, the invention relates to the method or process as described above, especially in the preceding paragraph, where the linear (this term where used meaning not yet cyclic) precursor peptide is of the formula VIII,

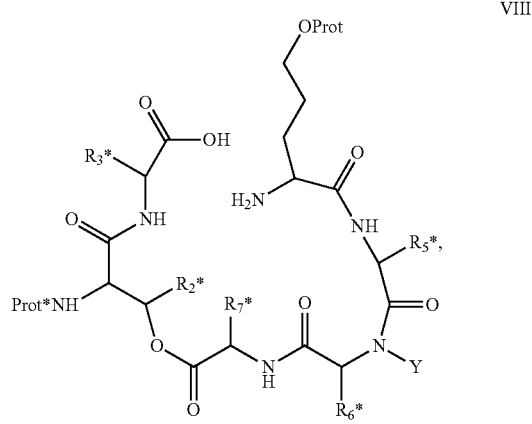

especially VIIIA

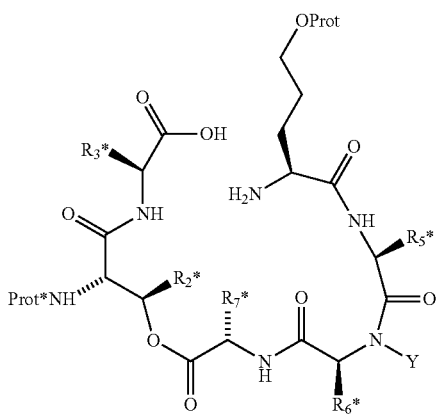

wherein Prot* is a protecting group that can be cleaved off selectively without affecting other protecting groups present and is stable during deprotection steps during synthesis of the linear precursor peptide (e.g. allyloxycarbonyl) and $R_2^*$, $R_3^*$, $R_5^*$, $R_6^*$, and $R_7^*$ are as defined for a compound of the formula VI as described above, further comprising, after cyclisation of the compound of the formula VIII, especially VIIIA, removing the protecting group Prot* in situ to yield the compound of the formula VI, especially VIA.

(vi/a) In another embodiment, the invention relates to the method or process described above, especially in the preceding paragraph, where the linear precursor peptide of the formula VIII, especially VIIIA, is synthesized from the corresponding amino acids by solid phase peptide synthesis and subsequent cleavage from the employed solid support.

(vii/a) An embodiment of the invention further relates to the method or process as described above (especially in the preceding paragraph (vi/a)), further comprising either in a variant a), coupling an amino acid of the formula IX,

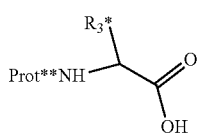

especially of the formula IXA,

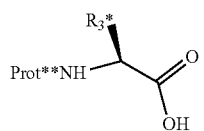

wherein $R_3^*$ is as defined for a compound of the formula II above and Prot is an amino protecting group that can be removed on the resin without cleaving other bonds, or a reactive derivative of said amino acid, via an oxygen to a cleavable linker L which is bound to a solid resin RES (e.g. by reaction with a resin of the formula $(X-L)_z$-RES wherein L and RES are as just defined, X is e.g. halo, e.g. chloro, and z is a number larger than zero, e.g. a natural number) and removing the protecting group Prot;

coupling the obtainable resin bound amino acid symbolized by the formula X,

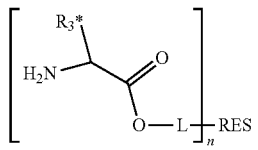

especially XA,

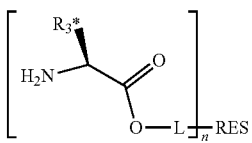

in which RES and $R_3^*$ are as defined for a compound of the formula IX, n is a (e.g. natural) number larger than zero and L is a cleavable linker, with an amino acid of the formula XI,

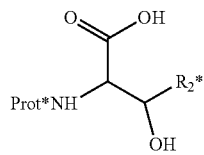

especially XIA,

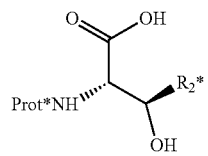

wherein Prot* is as defined for a compound of the formula VIII above and $R_2^*$ is as defined for a compound of the formula II above, or a reactive derivative of said amino acid, coupling the obtainable resin bound dipeptide symbolized by the formula XII,

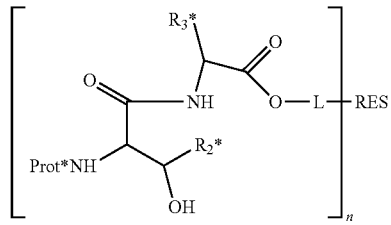

especially XIIA;

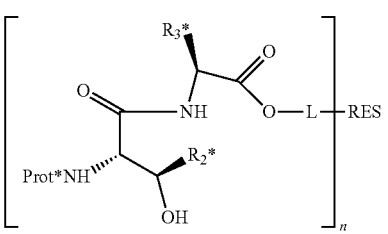

in which Prot* is as defined for a compound of the formula VIII above, $R_2^*$ and $R_3^*$ are as defined for a compound of the formula II above, and n, L and RES are as defined for a compound of the formula X, via the free hydroxy group with an amino acid of the formula XIII,

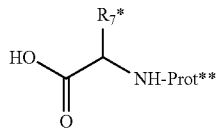

XIII especially XIIIA,

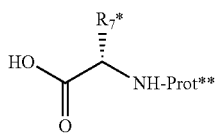

XIIIA wherein Prot** is as defined for a compound of the formula IX and $R_7^*$ is as defined for a compound of the formula II above, or a reactive derivative of said amino acid, and removing the protecting group Prot**;

or, in a variant b), coupling a dipeptide of the formula XXVII,

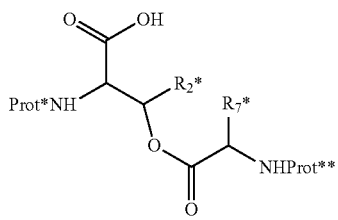

XXVII especially of the formula XXVIIA,

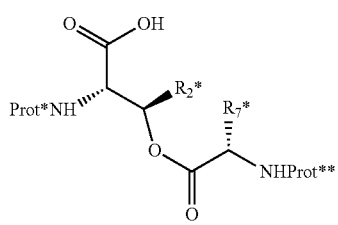

XXVIIA wherein $R_3^*$ and Prot** are as described for a compound of the formula IX, especially IXA, and Prot* is as defined for a compound of the formula VIII above, or a reactive derivative of said dipeptide, to an amino acyl moiety, bound via an oxygen to a cleavable linker L which is bound to a solid resin RES, having the formula X,

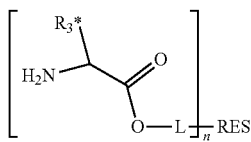

X especially XA,

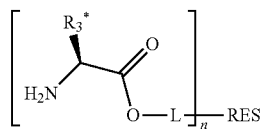

XA that can be obtained as described under variant a), in which RES, and $R_3^*$ are as defined for a compound of the formula IX and L and RES are as just defined;

and removing the protecting group Prot**;

and, after the reactions of variant a) or of variant b), (viii/a) coupling the obtainable compound of the formula XIV,

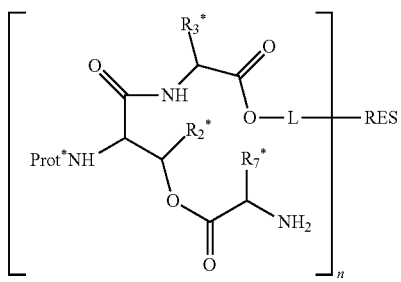

XIV especially XIVA,

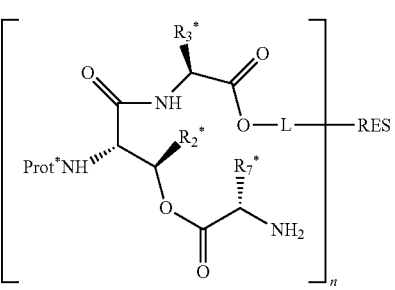

XIVA wherein $R_2^*$, $R_3^*$ and $R_7^*$ are as defined for a compound of the formula II above, Prot* is as defined for a compound of the formula VIII above and n, L and RES are as defined for a compound of the formula X, with an amino acid of the formula XV,

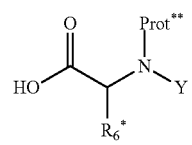

XV especially the formula XVA,

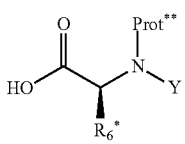

XVA in which $R_6^*$ and Y are as defined for a compound of the formula II above and Prot is as defined for a compound of the formula IX above, or a reactive derivative of said amino acid, and removing the protecting group Prot;

(ix/a) preferably coupling the obtainable compound of the formula XVI

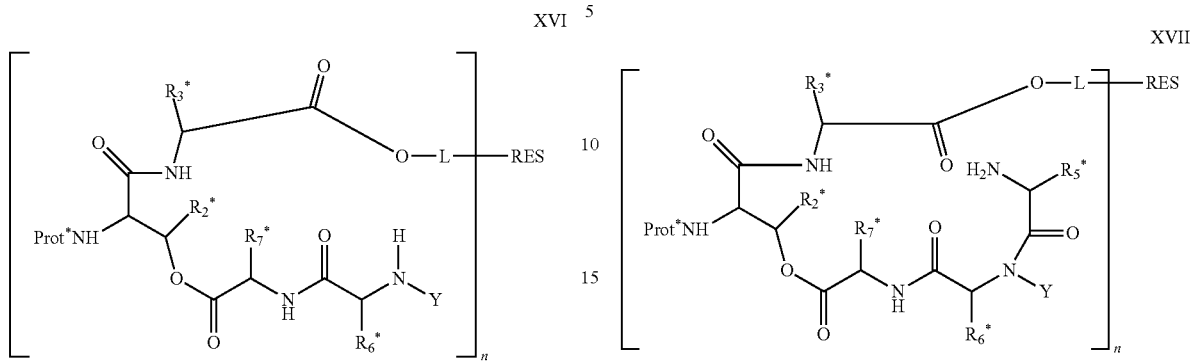

especially the formula XVIA,

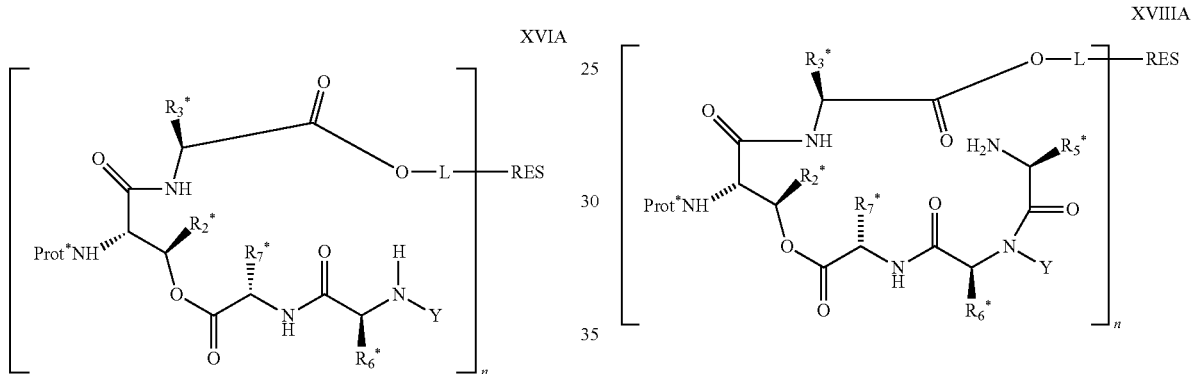

wherein Y, $R_2^*$, $R_3^*$, $R_7^*$ and $R_6^*$ are as defined for a compound of the formula II above, Prot* is as defined for a compound of the formula VIII above and n, L and RES are as defined for a compound of the formula X, with an amino acid of the formula XVII,

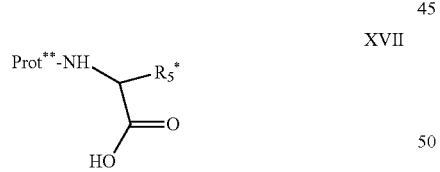

especially formula XVIIA,

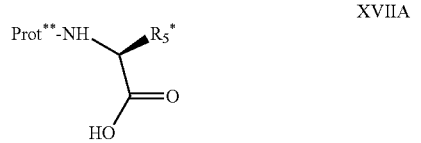

wherein $R_5^*$ is as defined for a compound of the formula II above and Prot is as defined for a compound of the formula IX, or a reactive derivative of said amino acid, and removing the protecting group Prot, and preferably
(x/a) finally coupling the resulting compound of the formula XVIII, especially XVIIIA, wherein Y, $R_2^*$, $R_3^*$, $R_7^*$, $R_6^*$ and $R_5^*$ are as defined for a compound of the formula II above, Prot* is as defined for a compound of the formula VIII above and n, L and RES are as defined for a compound of the formula X above, to an unnatural amino acid (=synthon) of the formula XIX,

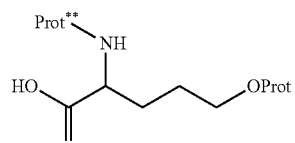

especially the formula XIXA,

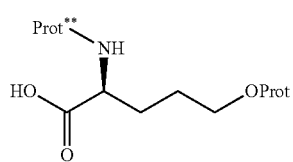

wherein Prot is as defined for a compound of the formula II above and Prot is as defined for a compound of the formula IX, or an activated derivative of said synthon, and removing the protecting group Prot to yield a compound of the formula XX,

XX

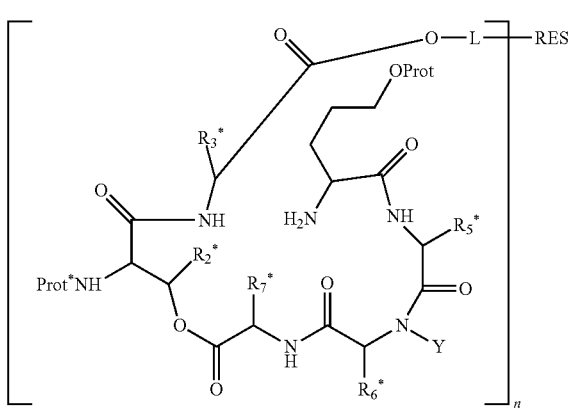

especially XXA,

XXA

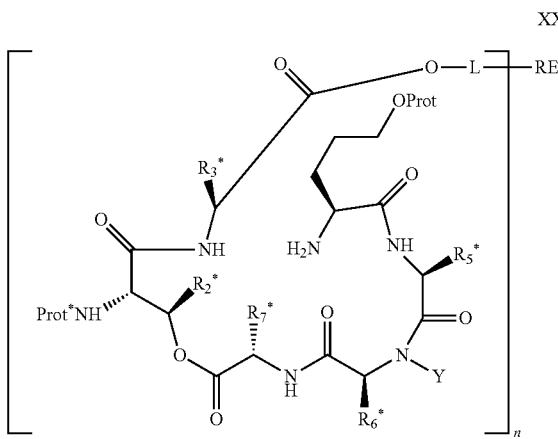

wherein Prot, Y, $R_2^*$, $R_3^*$, $R_7^*$, $R_6^*$ and $R_5^*$ are as defined for a compound of the formula II above, Prot* is as defined for a compound of the formula VIII above and n, L and RES are as defined for a compound of the formula X, and (xi/a) cleaving the solid phase bound peptide in formula XX off the solid phase L-RES to yield the corresponding compound of the formula VIII, especially VIIIA, as shown above.

Another embodiment of the invention relates to the synthesis of a compound of the formula II as given above according to section (i/a), preferably preceded by the reaction according to section (ii/a) or more preferably according to section (iii/a); preferably preceded by the reaction according to section (iv/a) or preferably (via), preferably preceded by the reaction according to section (vi/a), preferably preceded by the reaction according to section (x/a), preferably preceded by the reaction according to section (ix/a), preferably preceded by the reaction according to section (viii/a), preferably preceded by the reaction according to section (vii/a).

(i/b) Another embodiment of the invention relates to a method or process above, comprising, for the synthesis of the compound of the formula II given above, cyclization under lactamization of a linear, not yet cyclic, precursor peptide of the compound of the formula II, carrying an N-terminal amino group and a C-terminal carboxy group, under reaction conditions that allow for the formation of an amide bond from said amino and said carboxy group, preferably using Solution Phase chemistry.

(ii/b) A further embodiment of the invention relates to the method or process according to the preceding paragraph (i/b), where the linear precursor peptide is of the formula XXV,

XXV

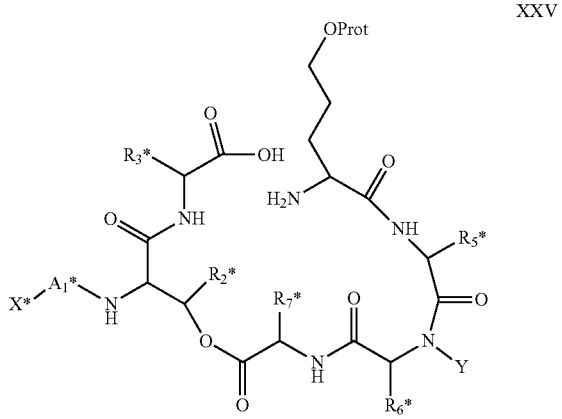

especially XXVA,

XXVA

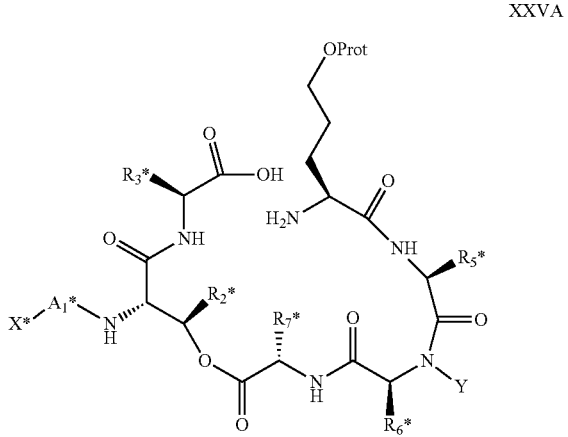

wherein $X^*$, $A_1^*$, $R_2^*$, $R_3^*$, $R_5^*$, $R_6^*$, $R_7^*$ and Prot are as defined for a compound of the formula II above.

(iii/b) Another embodiment refers to the method or process according to the preceding paragraph (ii/b), further comprising, for the synthesis of the compound of the formula XXV, cleaving a compound of the formula XXIV,

XXIV

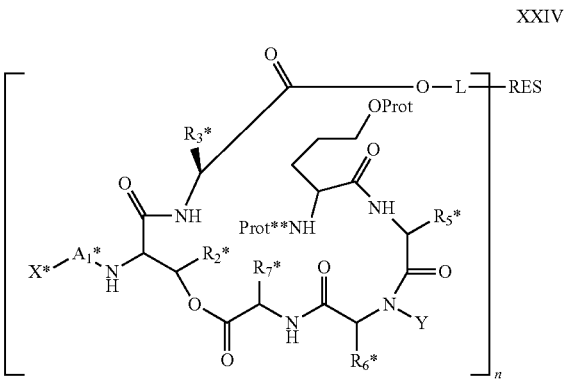

especially XXIVA,

XXIVA

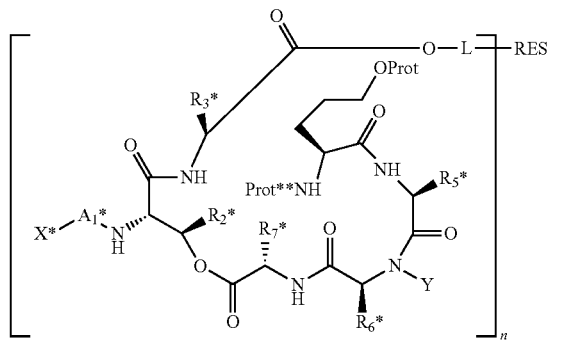

wherein X*, A₁*, R₂*, R₃*, R₅*, R₆*, R₇* and Prot are as defined for a compound of the formula II above, L is a cleavable linker, RES is a solid resin, n is a natural number and Prot is an amino protecting group that can be removed without parallel removal of the protecting group Prot and with the product remaining on the resin, and (before the cleavage, in parallel or subsequently to it) removing the protecting group Prot to yield the compound of the formula XXV.

(iv/b) A further embodiment of the invention relates to the method or process according to the preceding paragraph (iii/b), further comprising, for the synthesis of the compound of the formula XXIV, coupling an amino acid of the formula XIX,

XIX

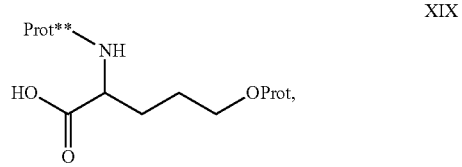

especially XIXA,

XIXA

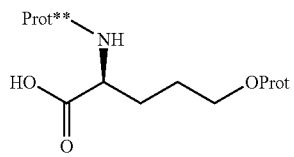

wherein Prot is as defined for a compound of the formula II above and Prot** is as defined for a compound of the formula XXIV above, or an activated derivative of said amino acid, with a compound of the formula XXIII, (XXIII)

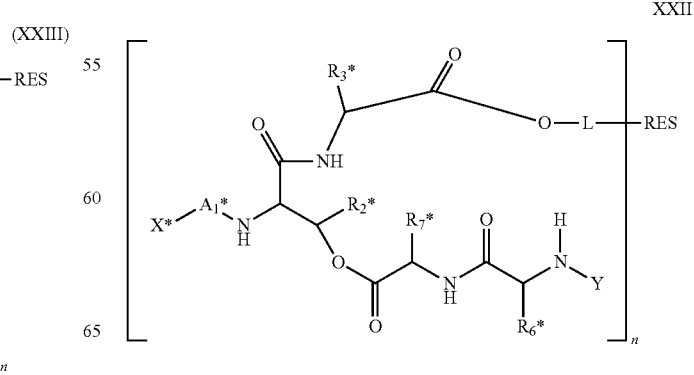

especially XXIIIA,

XXIIIA

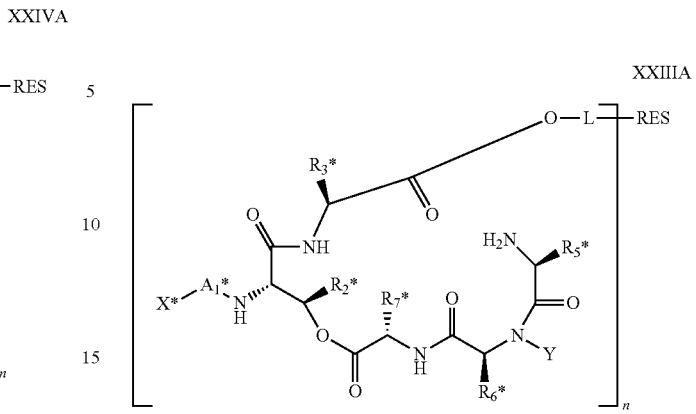

wherein X*, A₁*, R₂*, R₃*, R₅*, R₆* and R₇* are as defined for a compound of the formula II above, L is a cleavable linker, RES is a solid resin, and n is a natural number.

(v/b) Yet a further embodiment of the invention relates to the method or process according to the preceding paragraph (iv/b), further comprising, for the synthesis of the compound of the formula XXIII, coupling an amino acid of the formula XVII*

XVII*

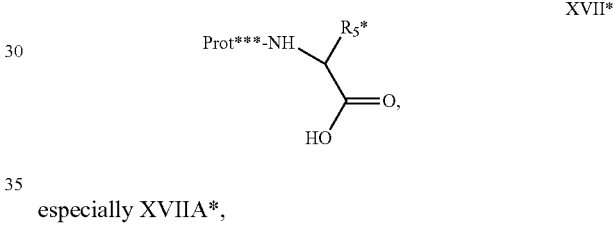

especially XVIIA*,

XVIIA* wherein R₅* is as defined for a compound of the formula II above and Prot*** is an amino protecting group that can be cleaved off selectively without affecting other protecting groups present and with the product remaining on the resin, or a reactive derivative of said amino acid, with a compound of the formula XXII,

XXII especially XXIIA

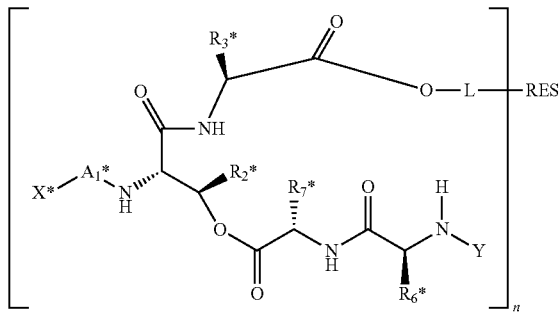

XXIIA wherein X*, A$_1$*, R$_2$*, R$_3$*, R$_6$* and R$_7$* are as defined for a compound of the formula II above, L is a cleavable linker, RES is a solid resin, and n is a natural number, and removing the protecting group Prot***.

(vi/b) In yet a further embodiment, the invention relates to the method or process according to the preceding paragraph (v/b), further comprising, for the synthesis of the compound of the formula XXII, coupling an amino acid of the formula XV*,

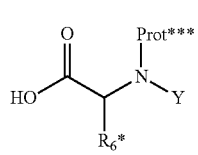

XV* especially XVA*

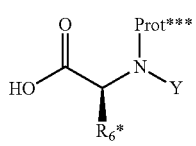

XVA* in which R$_6$* and Y are as defined for a compound of the formula II above and Prot*** is an amino protecting group that can be cleaved off selectively without affecting other protecting groups present and with the product remaining on the resin, or a reactive derivative of said amino acid, with a compound of the formula XXI,

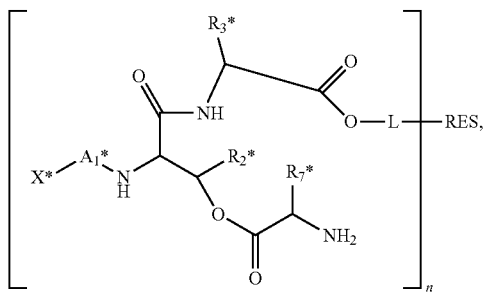

XXI especially XXIA,

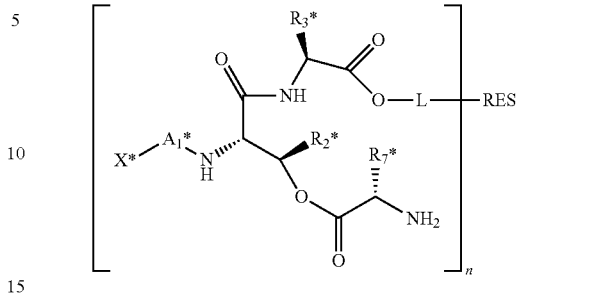

XXIA wherein X*, A$_1$*, R$_2$*, R$_3$* and R$_7$* are as defined for a compound of the formula II above, L is a cleavable linker, RES is a solid resin, and n is a natural number, and removing the protecting group Prot***.

(vii/b) Another embodiment of the invention relates to the method or process according to the preceding paragraph (vi/b), further comprising, for the synthesis of a compound of the formula XXI, reacting an amino acid of the formula XIII*,

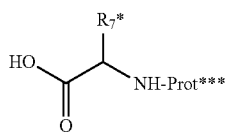

XIII* especially XIIIA*,

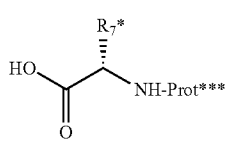

XIIIA* wherein Prot*** is an amino protecting group that can be cleaved off selectively without affecting other protecting groups present and with the product remaining on the resin, and R$_7$* is as defined for a compound of the formula II above, or a reactive derivative of said amino acid, with the hydroxyl group of a compound of the formula XXVI,

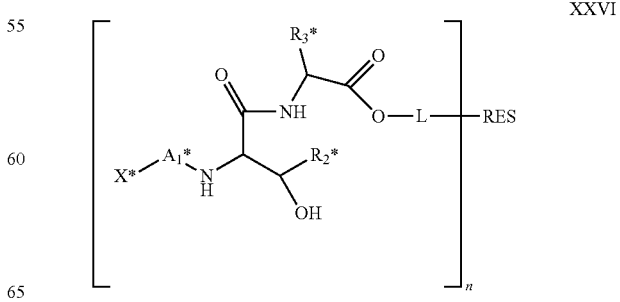

XXVI especially XXVIA,

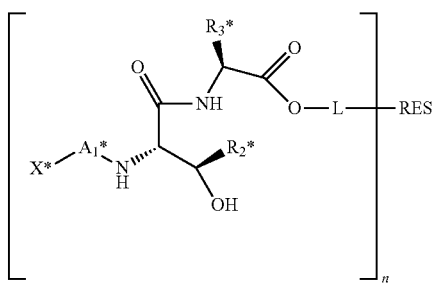

XXVIA wherein $X^*$, $A_1^*$, $R_2^*$ and $R_3^*$ are as defined for a compound of the formula II above, L is a cleavable linker, RES is a solid resin, and n is a natural number;

and removing the protecting group Prot***.

(viii/b) In a further embodiment, the invention relates to the method or process according to the preceding paragraph (vii/b), further comprising, for the synthesis of a compound of the formula XXVI, especially XXVIA, coupling a resin bound dipeptide symbolized by the formula XII*,

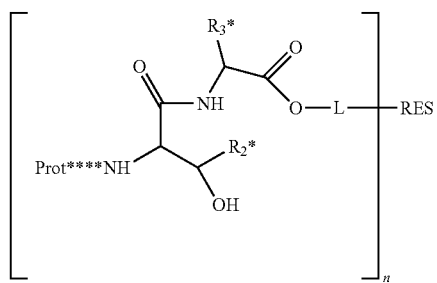

XII* especially XIIA*

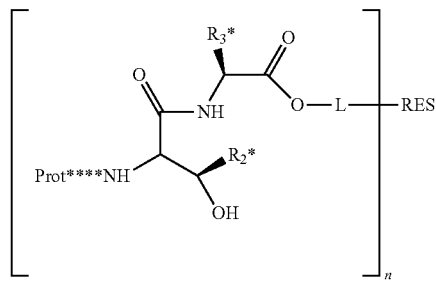

XIIA* in which Prot**** is a protecting group that can be cleaved off selectively without affecting other protecting groups present in a compound of the formula II as defined above and with the product remaining on the resin, $R_2^*$ and $R_3^*$ are as defined for a compound of the formula II above, L is a cleavable linker, RES is a solid resin, and n is a natural number, after removal of the protecting group Prot**** via the thus obtainable free amino group, with. an acid of the formula VII

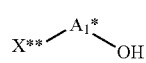 VII wherein $X^{**}$ is an amino protecting group or is $X^*$, and wherein $X^*$ and $A_1^*$ are as defined for a compound of the formula II above, or a reactive derivative of said acid;

and, if $X^{}$ is an amino protecting group, removing said amino protecting group $X^{}$ to yield the derivative of formula II wherein, instead of $X^*$, H is present and coupling the resulting amino group with an acyl group $X^*$ using the corresponding acid $X^*$—OH wherein $X^*$ is as defined for a compound of the formula II above, or a reactive derivative of said acid.

(ix/b) A yet further embodiment of the invention relates to the method or process according to the preceding paragraph (viii/b), further comprising, for the synthesis of a compound of the formula XII, coupling a resin bound amino acid symbolized by the formula X,

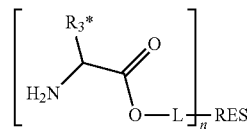

X especially XA,

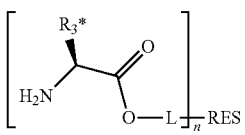

XA wherein $R_3^*$ is as defined for a compound of the formula II above, L is a cleavable linker, RES is a solid resin, and n is a natural number, with an amino acid of the formula XI*,

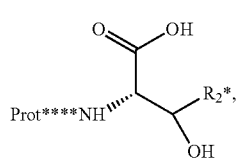

XI* especially XIA*,

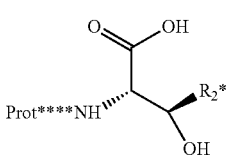

XIA* wherein Prot**** is a protecting group that can be cleaved off selectively without affecting other protecting groups present and with the product remaining on the resin, and $R_2^*$ is as defined for a compound of the formula II above, or a reactive derivative of said amino acid.

(x/b) A further embodiment of the invention relates to the method or process according to the preceding paragraph (ix/b), further comprising, for obtaining the resin bound amino acid of the formula X, coupling an amino acid of the formula IX*,

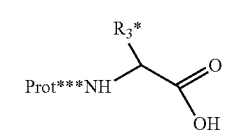

IX* especially IXA*,

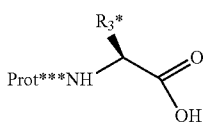

IXA* wherein R₃* is as defined for a compound of the formula II in claim 1 and Prot* is an amino protecting group can be cleaved off selectively without affecting other protecting groups present and with the product remaining on the resin; or a reactive derivative of said amino acid of the formula IX, to a cleavable linker L which is bound to a solid resin RES, and removing the protecting group Prot*.

(i/c) Another embodiment of the invention relates to the method or process according to any one of the preceding paragraphs (i/a) to (x/b) where the symbols $A_1$, R2, R3, R5, R6, R7, X and Y or the corresponding unprotected or protected moieties $R_2^*$, $R_3^*$, $R_5^*$, $R_6^*$, $R_7^*$, X* and Y3 are selected so that, in the resulting compound of the formula I, or a salt thereof, $A_1$ is the bivalent radical of L-glutamine bound via the carbonyl of its α-carboxy group to the amino group at the right of $A_1$ in formula I and via its α-amino group to X, or is 2S-(2-hydroxy-3-phosphonooxy)-propionyl;

$R_2$ is methyl;

$R_3$ is isopropyl, isobutyl (2-methyl-n-propyl wherever used) or benzyl, especially isobutyl;

$R_5$ is sec-butyl or benzyl, especially sec-butyl;

$R_6$ is 4-hydroxybenzyl;

$R_7$ is isopropyl or sec-butyl (1-methyl-n-propyl wherever used), especially sec-butyl;

X is acetyl or isobutyryl, or is absent if $A_1$ is 2S-(2-hydroxy-3-phosphonooxy)-propionyl and Y is methyl. This paragraph is also named paragraph a) below.

(i/d) In another particular embodiment, the invention relates to a method or process for converting a dehydrate of a compound of the formula I given above or in particular with the substituents as defined in the preceding paragraph (i/c) into the corresponding compound of the formula I, where the dehydrate has the formula V, especially VA,

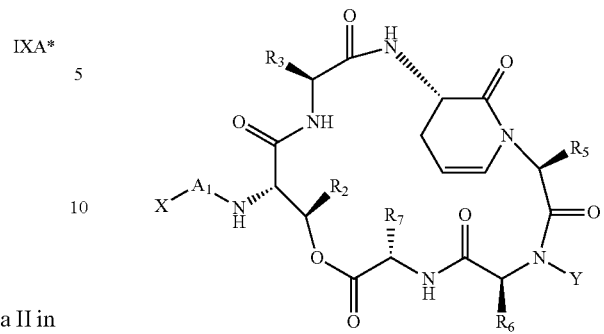

VA in which Y, X, $A_1$, $R_2$, $R_3$, $R_5$, $R_6$ and $R_7$ are as defined for a compound of the formula I above;

or especially a method or process for shifting the equilibrium of a mixture of a compound of the formula I and its corresponding dehydrate, and/or its corresponding hemiaminal analogue with a five-ring instead of the ahp structure in formula I which may also be formed as byproduct and has the formula V*,

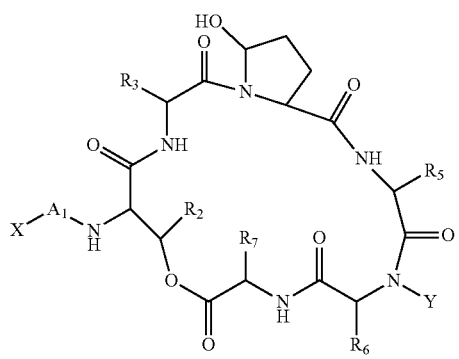

V* especially the formula VA*,

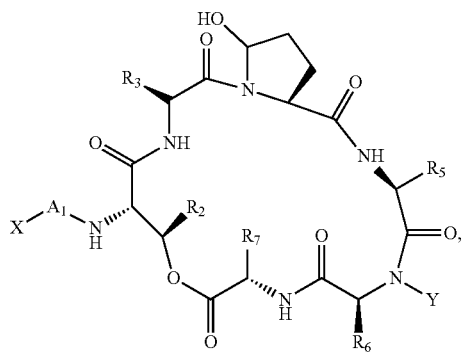

VA* in which Y, X, $A_1$, $R_2$, $R_3$, $R_5$, $R_6$ and $R_7$ are as defined for a compound of the formula I above, respectively;

in favor of the compound of the formula I, said method or process comprising using an aqueous acid as reactive solvent to drive the reaction. This method can be used independently (e.g. also for the product of fermentation or biosynthesis) or in addition to the other processes or methods described above and below to increase the yield or to re-convert a compound of the formula V, especially VA, and/or the analogue with a five-membered ring instead of the ahp structure in formula I, into the corresponding compound of the formula I.

The method described for the conversion of the dehydrate and/or the five ring analogue (always regarding the desired ahp ring) into the desired compound of the formula I or especially IA, e.g. of Compound A-dehydrate from Example 3 B into Compound A, enables a straight-forward synthesis of this class of compounds. Up to now, an acidic treatment as final step had to be circumvented in order to avoid the dehydration of the product.

(i/e) A further embodiment of the invention relates to the method according to the preceding paragraph (i/d), wherein the acid is a carboxylic acid, especially a halo substituted $C_{1-8}$alkanoic acid, more especially trifluoroacetic acid or trichloroacetic acid.

(i/f) The invention, in yet a further embodiment, relates to a compound of the formula II,

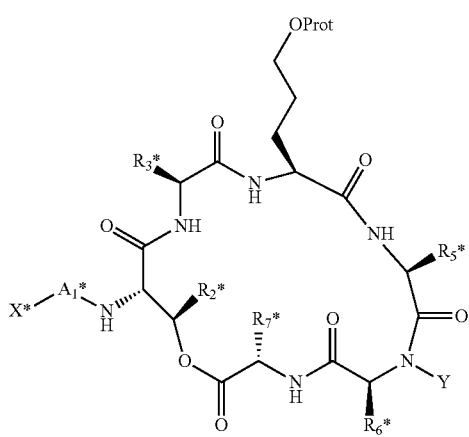

II wherein Prot is a protecting group, Y is as defined for a compound of the formula I in the first instance above or in particular as or claim 17 and $X^*$, $A_1^*$, $R_2^*$, $R_3^*$, $R_5^*$, $R_6^*$, and $R_7^*$ correspond to X, $A_1$, $R_2$, $R_3$, $R_5$, $R_6$, and $R_7$ in formula I as defined in claim 1 or in paragraph (ia) given above, respectively, however with the proviso that reactive functional groups on these moieties are present in protected form.

(i/g) In a further embodiment, the invention relates to a novel compound selected from the group consisting of compounds of the formula II, III, IV, V, VI, VIII, X, XII, XIV, XVI, XVIII, XIX, XX, XXI, XXII, XXIII, XXIV, XXV, XXVI and XXVIII, and especially of the formula IIA, IIIA, IVA, VA, VIA, VIIIA, XA, XIIA, XIVA, XVIA, XVIIIA, XIXA, XXA, XXIA, XXIIA, XXIIIA, XXIVA, XXVA, XXVIA and XXVIIIA, yet more especially to the group consisting of the following compounds given in the examples: From Scheme 1: compound 2, compound 3, compound 4, synthon 1; from Scheme 2: compound 5; Fmoc-Leu-Linker-Resin according to Example 1B(2); Fmoc-Thr-Leu-Linker-Resin according to Example 1B(3); Fmoc-Gln(Trt)-Thr-Leu-Linker-Resin according to Example 1B(4); Isobutyryl-Gln(Trt)-Thr-Leu-Linker-Resin according to Example 1B(5); Isobutyryl-Gln(Trt)-Thr(Ile-Fmoc)-Leu-Linker-Resin according to Example 1B(6); the product of Example 1B(7)=Isobutyryl-Gln(Trt)-Thr(Ile-Tyr(tBu)Me-Fmoc)-Leu-Linker-Resin (previously named: Isobutyryl-Gln(Trt)-Thr(Ile-N-me-Tyr(tBu)-Fmoc)-Leu-Linker-Resin); Isobutyryl-Gln(Trt)-Thr(Ile-Tyr(tBu)Me-Ile-Fmoc)-Leu-Linker-Resin (previously named: Isobutyryl-Gln(Trt)-Thr(Ile-N-me-Tyr(tBu)-Ile-Fmoc)-Leu-Linker-Resin) according to Example 1B(8); Isobutyryl-Gln(Trt)-Thr(Ile-Tyr(tBu)Me-Ile-Synthon 1-H)-Leu-Linker-Resin (previously named: Isobutyryl-Gln(Trt)-Thr(Ile-N-Me-Tyr(tBu)-Ile-Synthon 1-H)-Leu-Linker-Resin) according to example 1B(9). Isobutyryl-Gln(Trt)-Thr(Ile-Tyr(tBu)Me-Ile-Synthon 1-H)-Leu-OH (previously named: Isobutyryl-Gln(Trt)-Thr(Ile-N-Me-Tyr(tBu)-Ile-Synthon 1-H)-Leu-OH) according to example 1B(10) and Scheme 3; H-Thr-Leu-Resin according to example 1B(12); H-Gln(Trt)-Thr-Leu-Resin according to example 1B(13); Isobutyryl-Gln(Trt)-Thr-Leu-Resin according to example 1B(14); Isobutyryl-Gln(Trt)-Thr(Ile-H)-Leu-Resin according to example 1B(15); Isobutyryl-Gln(Trt)-Thr(Ile-Tyr(tBu)Me-H)-Leu-Resin according to example 1B(16); Isobutyryl-Gln(Trt)-Thr(Ile-Tyr(tBu)Me-Ile-H)-Leu-Resin according to example 1B(17); Isobutyryl-Gln(Trt)-Thr(Ile-Tyr(tBu)Me-Ile-Synthon 1-H)-Leu-Resin according to example 1B(18); from Scheme 3, Compound 6 and/or 7 (the latter preferred); from Scheme 4: Compound 8 and the 5-ring hemiaminal-isomer; from Scheme 5, precursor peptide 2, compound 9, compound 10 (this one being preferred in the present enumeration regarding Scheme 5), and/or compound 11; Fmoc-Thr-Leu-Trt-Tentagel-S from Example 2A(1); Fmoc-Gln(Trt)-Thr-Leu-Trt-Tentagel-S according to Example 2A(2); Ac-Gln(Trt)-Thr-Leu-Trt-Tentagel-S according to Example 2A(3); Ac-Gln(Trt)-Thr(Val-Fmoc)-Leu-Trt-Tentagel-S according to Example 2A(4); Ac-Gln(Trt)-Thr(Val-Tyr(tBu)Me-Fmoc)-Leu-Trt-Tentagel-S (previously named: Ac-Gln(Trt)-Thr(Val-N-Me-Tyr(tBu)-Fmoc)-Leu-Trt-Tentagel-S) according to Example 2A(5); Ac-Gln(Trt)-Thr(Val-Tyr(tBu)Me-Phe-Fmoc)-Leu-Trt-Tentagel-S (previously named: Ac-Gln(Trt)-Thr(Val-N-Me-Tyr(tBu)-Phe-Fmoc)-Leu-Trt-Tentagel-S) according to Example 2A(6); and Ac-Gln(Trt)-Thr(Val-Tyr(tBu)Me-Phe-Synthon1-H)-Leu-OH (previously named: Ac-Gln(Trt)-Thr(Val-N-Me-Tyr(tBu)-Phe-Synthon1-H)-Leu-OH) (precursor peptide 2) according to Example 2A(7).

The following definitions (or also definitions already included above) can replace more general terms used in invention embodiments above and below in order to define further embodiments of the invention, with either one, two or more or all general terms being replaceable by the more specific terms in order to define such invention embodiments:

A bivalent moiety of an amino acid with a terminal carboxy or carbamoyl group is preferably an alpha-carbamoyl or carboxyl-$C_{1-8}$-substituted amino acid, especially the bivalent moiety of asparagine or glutamine, and is bound at its right hand side in formula I via a carbonyl (preferably the carbonyl of its α-carboxyl group) to the rest of the molecule.

$C_{1-8}$-alkanoyl or phosphorylated hydroxy-$C_{1-8}$-alkanoyl ($C_{1-8}$-alkanoyl carrying both a hydroxyl and a phosphono (—O—P(=O)(OH)$_2$) group) $A_1$ is e.g. 2,3-dihydroxy-propanoyl (preferably in S-form) or 2-hydroxy-3-phosphono-propanoyl (preferably in S-form).

$R_2$ and $R_2^*$ are $C_{1-8}$-alkyl, especially methyl wherever mentioned.

$R_3$ is the side chain of an amino acid, especially of a natural amino acid. Preferably, it is $C_{1-8}$ alkyl which may be branched or linear. Most especially, $C_{1-8}$alkyl is n-(2-methyl)propyl (isobutyl), n-(1-methylpropyl(sec-butyl) or methyl, that is, the amino acid carrying the moiety is leucine, isoleucine or valine.

$R_3^*$ is the corresponding side chain in protected form if a functional group is present that has to be hindered to participate in a reaction. Preferably, it is $C_{1-8}$alkyl which may be branched or linear, especially as defined in the preceding paragraph.

A "side chain of an amino acid" may be selected from any moiety, e.g. a mono- or polycyclic, linear, saturated, unsaturated (e.g. with conjugated double bonds) or partially saturated organic moiety, e.g. with up to 20 carbon atoms and 0 to 5 heteroatoms in the basis structure independently selected from N, O and S replacing the corresponding number of carbon atoms, and may be substituted by up to three moieties selected from amino, imino, hydroxy, carboxy, carbamoyl, sulfhydryl, amidino, guanidino, O-phosphono (—O—P(=O)(OH)$_2$). Preferably, the side chains are selected from those of the 20 standard alpha-amino acids arginine, histidine, lysine, aspartic acid, glutamic acid, serine, threonine, asparagine, glutamine, cysteine, glycine, alanine, leucine, isoleucine, methionine, phenylalanine, tryptophan, tyrosine, valine and further proline (then with internal cyclization including the alpha-amino group).

For the amino acids, either their names or the customary three letter codes are used in the present disclosure, in accordance with the following table:

| Amino acid | Three letter code |
|---|---|
| Alanine | Ala |
| Arginine | Arg |
| Asparagine | Asn |
| Aspartic acid | Asp |
| Asparagine or aspartic acid | Asx |
| Cysteine | Cys |
| Glutamic acid | Glu |
| Glutamine | Gln |
| Glutamine or glutamic acid | Glx |
| Glycine | Gly |
| Histidine | His |
| isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Try |
| Tyrosine | Tyr |
| Valine | Val |

$R_5$ is the side chain of an amino acid, preferably a standard amino acid. Preferably, it is $C_{1-8}$ alkyl which may be branched or linear and which is unsubstituted or substituted by phenyl. Most especially it is benzyl, n-(2-methyl)propyl, isobutyl or methyl, that is, the amino acid carrying the moiety is phenylalanine, leucine, isoleucine or valine.

$R_6$ is the side chain of a hydroxy amino acid, especially of tyrosine.

$R_7$ is the side chain of an amino acid, especially of a natural amino acid. Preferably, it is $C_{1-8}$alkyl which may be branched or linear. Most especially it is n-(2-methyl)propyl(isobutyl), n-(1-methyl)propyl(sec-butyl) or methyl, that is, the amino acid carrying the moiety is leucine, isoleucine or valine.

$C_{1-8}$-alkyl can be linear or branched one or more times; for example, it can be n-(2-methyl)propyl, n-(1-methyl)propyl or methyl.

All of the compounds can, where salt-forming groups such as basic groups, e.g. amino or imino, or acidic groups, e.g. carboxyl or phenolic hydroxyl, are present, be used in free form or as salts or as mixtures of salts and free forms. Thus where ever a compound is mentioned, this includes all these variants. For example, basic groups may form salts with acids, such as hydrohalic acids, e.g. HCl, sulfuric acid or organic acids, such as acetic acid, while acidic groups may form salts with positive ions, e.g. ammonium, alkylammonium, alkali or alkaline-earth metal salt cations, e.g. Ca, Mg, Na, K or Li cations, or the like.

"Or the like" or "and the like", wherever used in this disclosure, refers to the fact that other alternatives to those mentioned preceding such expression are known to the person skilled in the art and may be added to those expressions specifically mentioned; in other embodiments, "or the like" and "and the like" may be deleted in one or more or all invention embodiments.

The protecting groups Prot, Prot*, Prot, Prot*, Prot**** and any further protecting groups present on the moieties A*, $R_2$*, $R_3$*, $R_5$*, $R_6$*, $R_7$*, X*, where ever mentioned throughout the present description and claims, are selected so that they allow for orthogonal protection.

Orthogonal protection is a strategy allowing the deprotection of multiple protective groups one (or more but not all) at the time where desired each with a dedicated set of reaction conditions without affecting the other protecting group(s) or bonds to resins, e.g. via linkers on solid synthesis resins. In other terms: The strategy uses different classes of protecting groups that are removed by different chemical mechanisms, also using appropriate linkers in the case of solid phase peptide synthesis (where the linker-resin bond might together be considered as a carboxy protecting group).

Preferably, the protecting groups are selected as follows:

The protecting group Prot is preferably selected so as to resist removal of any other protecting groups used or present during the synthesis according to the invention of a depsipeptide, e.g. able to resist mild bases (see Prot*), but removable with fluoride ion (especially under anhydrous conditions), e.g. Bu$_4$N$^+$F$^-$ (also if created in situ, e.g. using Bu$_4$N$^+$Cl$^-$ with KF.H$_2$O, KF with 18-crown-6, LiBr with 18-crown-6, BF$_3$.diethylether, pyridine-HF, HF in urea, Et$_3$N(HF)$_3$ (wherein Et is ethyl) or the like, where the solvent is e.g. selected from the group consisting of N,N-dimethylformamide, acetonitrile, chloroform and tetrahydrofurane.

Preferably, Prot is an ether protecting group, especially selected from the group consisting of silyl protecting groups in which the silyl moiety carries up to three organic moieties bound via a carbon (optionally via a further Si atom), such as tert-butyldiphenylsilyl, trimethylsilyl, triisopropylsilyl, tert-butyldimethylsilyl, triphenylsilyl, diphenylmethylsilyl, ti-tert-butyldimethylsilyl, tert-butylmethoxyphenylsilyl, tris(trimethylsilyl)silyl or the like.

Prot* is a protecting group that can be cleaved off selectively without affecting other protecting groups present, and also without affecting the depsipeptide forming ester bond or a linker to a resin RES, and is stable during deprotection steps during synthesis of the linear precursor peptide (e.g. removal of allyloxycarbonyl); it is preferably a protecting group removable by specific triphenylphosphin complexes in the presence of metal hydrides or other reductants, e.g. (PH$_3$P)$_4$Pd preferably in combination with di-n-butyl tin hydride or tri-n-butyl tin hydride, phenylsilane, sodium borohydride or dimedone, in an appropriate solvent, e.g. tetrahydrofurane, and is preferably not cleavable under conditions that allow for the removal of a protecting group Prot**; for example, and Prot* is selected from the group consisting of C$_3$-C$_8$alk-2-enyloxycarbonyl moieties, e.g. allyloxycarbonyl (Alloc), 1-isopropylallyloxycarbonyl, 4-nitrocinnamyloxycarbonyl and 3-(3'-pyridyl)prop-2-enyloxycarbonyl.

Prot** is a protecting group that can be removed on the resin without cleaving other bonds (no cleavage of an amino acid or peptide bound via the carbonyl of its (especially α-carboxyl group to the binding via a linker L mentioned below; also without cleaving off the protecting group Prot once present), especially a protecting group removable without cleavage of an ester (instead of an amide) bond in a depsipeptide or depsipeptide precursor and under conditions other than those for the protecting groups Prot* and Prot, while preserving the binding via the linker to a resin RES where present; it is preferably removable by a mild base e.g. piperidine, morpholine, dicyclohexylamine, p-dimethyl-amino-pyridine, diisopropylamine, piperazine, tris-(2-aminoethyl)amine in an appropriate solvent, e.g. N,N-dimethyl-formamide, methylene chloride; Prot** is, e.g., selected from the group consisting of fluoren-9-ylmethoxycarbonyl (Fmoc); 2-(2' or 4'-pyridyl)ethoxycarbonyl and 2,2-bis(4'nitrophenyl)ethoxycarbonyl.

Prot* (an amino protecting group that can be cleaved off selectively without affecting other protecting groups present and with the product remaining on the resin) and Prot (a protecting group that can be cleaved off selectively without affecting other protecting groups present in a compound of the formula II as defined above and below and with the product remaining on the resin) are preferably protecting groups that can be removed as Prot and are, e.g., selected from those mentioned for R**, e.g. fluoren-9-ylmethoxycarbonyl (Fmoc).

The preferred orthogonal synthesis method in this case makes use of the Fmoc method known in general for peptide synthesis using solid phase peptide synthesis combined with solution phase macrolactamization and further chemical conversions.

Alternatively, e.g. the Boc protecting group might be used instead of Fmoc Prot, Prot* and Prot****.

However, this will require different side chain protecting groups and also the hydroxy-group of N-methyl-Tyr will then have to be protected in a different way to maintain orthogonality of the protection groups.

Other protecting groups present as well as the binding linker to a resin RES where present are preferably not removable under conditions under which Prot* and Prot** can be removed, e.g. in A*, the amide can be N-protected e.g. with trityl (triphenylmethyl) (cleavage e.g. with trifluoro acetic acid (TFA); in $R_6^*$ a tyrosine hydroxy can be protected as t-butyl-ether, or protected by tert-butyldimethylsilyl, methoxymethyl, Boc (tert-butoxycarbonyl) or arylacetate (cleavage with TFA).

Appropriate protecting groups are known in the art, as well methods for their introduction and removal. For example, the protecting groups, their introduction and removal methods may be selected from those described in standard textbooks such as "Protective Groups in Organic Synthesis", 3$^{rd}$ ed., T. W. Green and P. G. M. Wuts (Eds.). J. Wiley & Sons, Inc., New York etc. 1999.

The protecting groups Prot, Prot*, Prot, Prot*, Prot**** and other protecting groups are thus not limited to those mentioned above—rather they should fulfill conditions that make them appropriate for orthogonal protection, e.g. as described above or below.

It is recommended to avoid too basic conditions (though the bases described for Fmoc cleavage, such as piperidine, are usually allowable) to avoid cleavage of the depsipeptide (ester) bond.

Among the possible solid support for Solid Phase Peptide Synthesis (SPPS), the following may be mentioned:
  Gel-type supports without or with spacer: These are highly solvated polymers with an equal distribution of functional groups. This type of support is the most common, and includes:
Polystyrene: Styrene cross-linked with e.g. 1-2% divinylbenzene; Polyacrylamide or polymethacrylamide: as hydrophilic alternative to polystyrene; Polyethylene glycol (PEG): PEG-Polystyrene (PEG-PS) is more stable than polystyrene and spaces the site of synthesis from the polymer backbone; PEG-based supports: Composed of a PEG-polypropylene glycol network or PEG with polyamide or polystyrene (these already include a spacer, PEG);
  Surface-type supports: Materials developed for surface functionalization, including controlled pore glass, cellulose fibers, and highly cross-linked polystyrene.
  Composites: Gel-type polymers supported by rigid matrices.

Usually these gels carry reactive groups to which a linker L as mentioned for various precursors above and below can be bound. For example, such groups include aminomethyl groups, polyethyleneglycol groups with a terminal hydroxy, and the like.

Any such support can be used in the embodiments of the present invention.

Gel type supports are used in another special embodiment of the invention, Among these, polystyrene (divinylbenzene crosslinked); polyacrylamide and polymethacrylamide resins are especially preferred.

Among the possible linkers, all commonly known and appropriate may be used.

Examples in possible embodiments of the invention are the 2-methoxy-4-benzyloxy-benzyl alcohol linker (a Sasrin-Linker, Sasrin stands for superacid sensitive resin, binds the amino acids or peptides via alcoholic OH); the trityl linker family (e.g, Trityl, 2Cl-Trityl, which bind the amino acids or peptides via OH); the 4-(2,4-dimethoxyphenylhydroxymethyl)phenoxymethyl-Linker (Rink-Acid-Linker, binds the amino acids or peptides via OH); or tris(alkoxy)benzyl ester linkers (HAL-Linker, binds the amino acids or peptides via OH).

Where reactive derivatives of acids, especially amino acids, or peptides, e.g. dipeptides, are mentioned, they may be formed in situ or may be used as such.

Reactive (or active) derivatives used as such include the acyl-halides, e.g. acyl-chlorides, -fluorides or -nitrophenyl esters, e.g. the 2,4-dinitrophenyl esters, or acid anhydrides (symmetric or e.g. with acetic acid) of the carboxy groups of the acids to be reacted.

For in situ amino acid activation, customary coupling agents may be applied. Such reagents are known to the person skilled in the art and can be purchased conveniently from many sources, e.g. Aldrich ChemFiles—Peptide Synthesis (Aldrich Chemical Co., Inc., Sigma-Aldrich Corporation, Milwaukee, Wis., USA) Vol. 7 No. 2, 2007 (see http://www.sigmaaldrich.com/etc/medialib/docs/Aldrich/Brochure/al_chemfile_v7_n2.Par.0001.File.tmp/al_chemfile_v7_n2.pdf). Among the possible coupling agents for amide and ester bond synthesis the following may be mentioned:

Triazoles, uronium or hexafluorophosphonium derivatives, e.g. 1-hydroxy-benzotriazole (HOBt), 1-hydroxy-7-aza-benzotriazole (HOAt), ethyl 2-cyano-2-(hydroxyimino) acetate, 2-(1H-7-Azabenzotriazol-1-yl)-1,1,3,3-tetramethyluronium hexafluorophosphate methanaminium (HATU), benzotriazol-1-yl-oxytripyrrolidinophosphonium hexafluorophosphate (PyBOP), Benzotriazole-1-yl-oxy-tris-(dimethylamino)-phosphonium hexafluorophosphate (BOP), 1-(mesitylene-2-sulfonyl)-3-nitro-1,2,4-triazole (MSNT), 2-(1H-benzotriazol-1-yl)-1,1,3,3-tetramethyluronium-hexafluorophosphate (HBTU), 2-(1H-benzotriazol-1-yl)-1,1,3,3-tetramethyluronium-hexafluoroborate (TBTU), 2-succinimido-1,1,3,3-tetramethyluronium-tetrafluoroborate (TSTU), 2-(5-norbornen-2,3-dicarboximido)-1,1,3,3-tetramethyluronium-tetrafluoroborate (TNTU), O-[(cyano (ethoxycarbonyl)-methyliden)amino]-1,1,3,3-tetramethyluronium-tetrafluoroborate (TOTU), O-(benzotriazol-1-yl)-1,3-dimethyl-1,3-dimethylene uronium hexafluorophosphate (HBMDU), O-(benzotriazol-1-yl)-1,1,3,3-bis(tetramethylene)uronium hexafluorophosphate (HBPyU), O-(benzotriazol-1-yl)-1,1,3,3-bis(pentamethylene)uronium hexafluorophosphate (HBPipU), 3-hydroxy-4-oxo-3,4-dihydro-1,2,3-benzotriazine (HODhbt), 1-hydroxy-7-aza-benzotriazole and its corresponding uronium or phosphonium salts, designated HAPyU and AOP, 1-cyano-2-ethoxy-2-oxoethylideneaminooxy-dimethylamino-morpholino-carbenium hexafluorophosphate (COMU), chlorotripyrrolidinophosphonium hexafluorophosphate (PyCloP), or the like;

Carbodiimides, e.g. dicyclohexylcarbodiimide, N-(3-dimethylaminopropyl)-N'-ethylcarbodiimide, 1-tert-butyl-3-ethylcarbodiimide, N-cyclohexyl-N'-2-morpholinoethyl)carbodiimide or diisopropylcarbodiimide (especially for ester formation via O-acyl urea formation of the carboxylic group); or active ester forming agents, e.g. 2-mercaptobenzothiazole (2-MBT), azide forming agents, e.g. diphenyl phosphoryl azide, acid anhydrides, such as propane phosphonic acid anhydride, acid halogenation agents, e.g. 1-chloro-N,N,2-trimethyl-1-propenylamine, chloro-N,N,N',N'-bis(tetramethylene)formamidinium tetrafluoroborate or hexafluorophosphate, chloro-N,N,N',N'-tetramethlformamidinium hexafluorophosphate, fluoro-N,N,N',N'-tetramethylformamidinium hexafluorophosphate, fluoro-N,N,N',N'-bis(tetramethylene)formamidinium hexafluorophosphate, or the like, or mixtures of two or more such agents.

Also for the ester coupling of compounds of the formula XII or XIIA with those of the formula XIII or XIIIA, respectively, or of compounds of the formula XIII* or XIIIA*with those of the formula XXVI or XXVIA, respectively, the corresponding reactive carboxyl compounds can be used or formed in situ. Here, especially MSNT is preferred as coupling agent as this allows for the maintenance of high stereospecificity.

The reaction may, where appropriate, be conducted in the presence of a mild base (e.g. N-methylmorpholine, a trialkylamine, e.g. ethyldiisopropylamine, a di-(alkyl)aminopyridine, such as N,N-dimethylaminopyridine, or the like (taking care that the conditions are not so basic as to allow for the hydrolysis of ester groups, e.g. the depsipeptide ester group, present in precursors of the compound of the formula I), where appropriate or required in the presence of an appropriate solvent or solvent mixture, e.g. an N,N dialkyl-formamide, such as dimethylformamide, a halogenated hydrocarbon, e.g. dichloromethane, N-alkylpyrrolidones, such as N-methylpyrrolidone, nitriles, e.g. acetonitrile, or further an aromatic hydrocarbon, e.g. toluene, or mixtures of two or more, where, provided an excess of coupling agent is present, also water may be present. The temperatures may be ambient temperature or lower or higher, e.g. in the range from −20° C. to 50° C.

The amino acids of the formula IX, IXA, XI, XIA, XIII, XIIIA, XV, XVA, XVII, XVIIA, XXVII (obtainable e.g. by Solution Phase synthesis), XVII*, XVIIA*, XV*, XVA*, XIII*, XIIIA*, XI*, XIA*, IX* and XIA* are known or they can be synthesized according to methods known in the art, they are commercially available, and/or they can be synthesized in analogy to methods known in the art.

Also the remaining starting materials, e.g. the acid of the formula XIX or VII, or the dipeptide of the formula XXVII or XXVIIA, are known or they can be synthesized according to methods known in the art, they are commercially available, and/or they can be synthesized in analogy to methods known in the art.

For example, the synthon of the formula XIX can be prepared as described in Example 1 A(4) (which is a specific embodiment of the invention) or in analogy thereto. The synthesis of the intermediate compound 1 (Scheme 1) is described in Tetrahedron 61, 1459-1480 (2005).

The coupling reactions for dipeptides make use of the corresponding carboxylic groups of amino acids in free form or in activated form.

EXAMPLES

The following examples illustrate the invention without limiting its scope.

Abbreviations
aq. aqueous
Boc/BOC tert-Butoxycarbonyl
brine sodium chloride solution in water (saturated at RT)
Bzl benzyl
COMU 1-cyano-2-ethoxy-2-oxoethylideneaminooxy-dimethylamino-morpholino-carbenium hexafluorophosphate
DCM dichloromethane
DIPEA N,N-diisopropylethylamine
DMAP 4-Dimethylaminopyridine
DMF N,N-dimethylformamide
Fmoc/FMOC 9-fluorenymethoxycarbonyl
Et ethyl
HATU 2-(1H-7-Azabenzotriazol-1-yl)-1,1,3,3-tetramethyluronium hexafluorophosphate Methanaminium
HFIP Hexafluoroisopropanol
HPLC High Performance Liquid Chromatography
HR-MS High Resolution Mass Spectroscopy
IPA Isopropylacetate
IPC In-Process Control
IR Infrared Spectroscopy
IT internal temperature
Kaiser test Ninhydrin-based test to monitor deprotection in SPPS (see E. Kaiser, R. L. Colescott, C. D. Bossinger, P. I. Cook, Analytical Biochemistry 1970, 34 595); if mentioned to be OK, this means successful deprotection.
me methyl
MS Mass Spectroscopy
MSNT 1-(Mesitylene-2-sulfonyl)-3-nitro-1,2,4-triazole
NMR Nuclear Magnetic Resonance Spetroscopy
PyBOP benzotriazol-1-yl-oxytripyrrolidinophosphonium hexafluorophosphate
BOP Benzotriazole-1-yl-oxy-tris-(dimethylamino)-phosphonium hexafluorophosphate
RP Reversed Phase
RT/rt room temperature
SPPS Solid Phase Peptide Synthesis
TBME tert-Butyl-methylether
TFA trifluoroacetic acidTEMPO 2,2,6,6-Tetramethyl-1-piperidinyloxy, free radical.
RBF Round bottomed flask For amino acid abbreviations see the table above.

Compounds Names . . .

The names of the open chain oligopeptides have been derived according to recommendations of the Joint Commission on Biochemical Nomenclature ("International Union of Pure and Applied Chemistry" and "International Union of Biochemistry") published in Pure & Appl. Chem. 1984, 56, 595-624. Previously, a simple peptide naming convention was used for these compounds. The previous names are given in parenthesis.

Example 1

Synthesis of Compound A

1A Synthesis of Synthon 1
(i) Alternative 1:

Reaction Scheme 1:

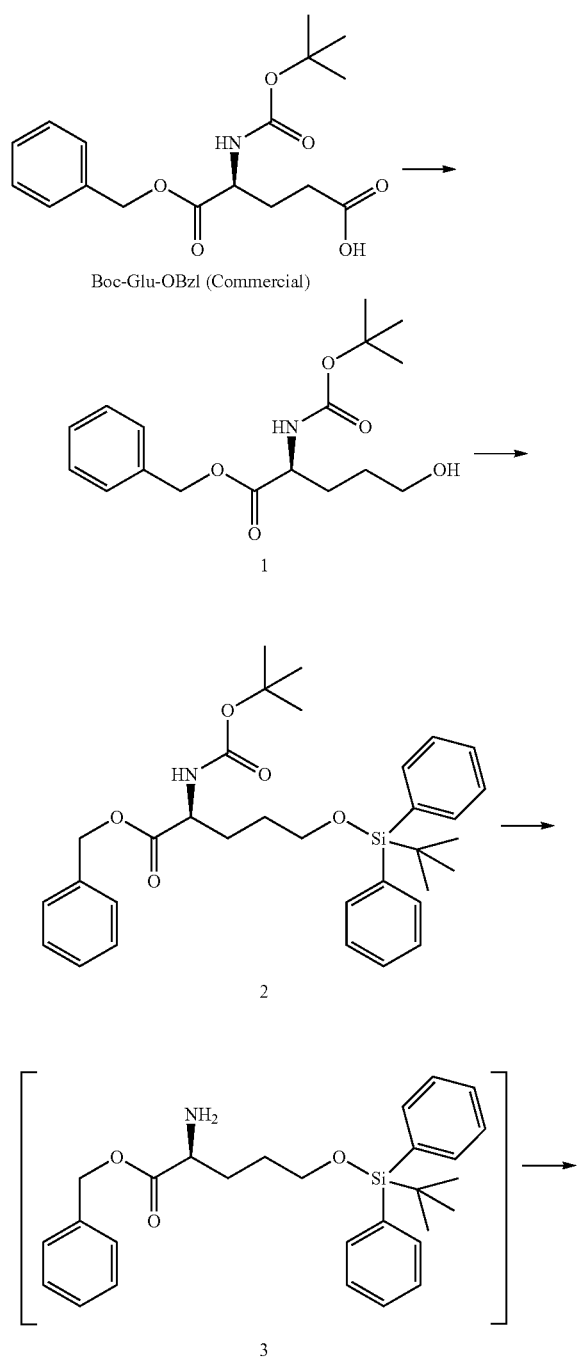

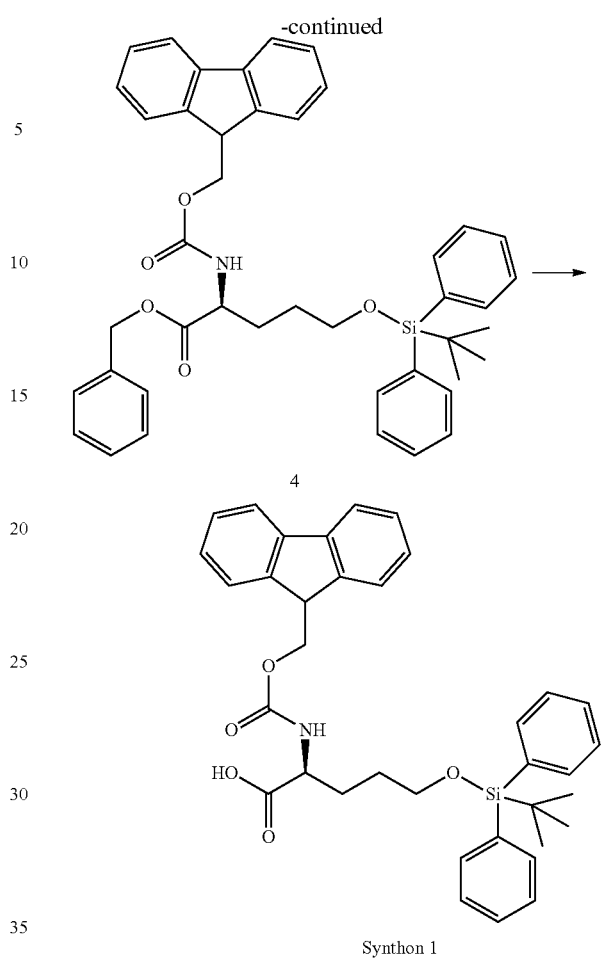

1A(1) Preparation of Compound 1
(S)-Benzyl 2-((tert-butoxycarbonyl)amino)-5-hydroxypentanoate Compound 1 was prepared by a procedure similar to the procedure reported in R. K. Olson, K. Ramasamy, T. Emery, *J. Org. Chem.* 1984, 49, 3527. BOC-Glu-OBzl (50 g, 148.2 mmol) was dissolved in tetrahydrofuran (800 mL) and triethylamine (47.3 g, 467.4 mmol) was added. The solution was cooled down to IT=−10° C. Ethyl-chloroformate (51.8 g, 98% purity, 467.8 mmol) was added slowly, maintaining the temperature at IT=−10 to −15° C. The suspension thus obtained was stirred for an additional hour. IPC (HPLC) indicated the disappearance of the starting material. The reaction mixture was allowed to warm-up to 0° C. and water (800 mL) was added at 0-5° C. within 25-30 minutes. Separation of the mixture into 2-phases became visible. Under intensive stirring, sodium-borohydride (11.8 g, 299.4 mmol) was added in 10 portions at 0-5° C. Caution was exercised as hydrogen gas evolved during addition of sodium-borohydride. The reaction mixture was stirred for additional 5 minutes at 0-5° C. and the temperature was increased to 20-25° C. within 30 minutes. Caution was required as hydrogen-gas continued to evolve during temperature increase. The reaction mixture was stirred for 15 minutes at 20-25° C. before work-up.

For work-up, water (1250 mL) was added to the reaction mixture, followed by the addition of ethyl acetate (1250 mL). The phases were separated and the aqueous phase was extracted with ethyl acetate (600 mL). The organic layers were combined and were washed with brine (2×600 mL). The organic layer was dried over magnesium sulfate, the solvent was evaporated at reduced pressure and 40-45° C. to obtain 50.8 g crude product. HPLC purity: 94 a %. The crude product was purified by flash chromatography on silica gel with hexane fraction/ethyl acetate (7:3 to 1:1) as mobile phase.

Yield: 40.85 g (85.2%). Purity: 98% (HPLC). MS and NMR confirmed the proposed structure.

1A(2) Preparation of Compound 2: (S)-Benzyl 2-((tert-butoxycarbonyl)amino)5-((tert-butyldiphenylsilyl)oxy)pentanoate The alcohol (compound 1) from the previous step (40.3 g, 124.6 mmol) was dissolved in dimethyl formamide (200 mL) and imidazole (12.8 g, 99.5% purity, 186.9 mmol) was added. The mixture was stirred at room temperature, until a solution was formed (5-10 min). tert.-Butyl-diphenyl-silyl-chloride (41.9 g, 98% purity, 149.5 mmol) was added dropwise within 10 minutes and stirring was continued for additional 15 minutes at room temperature. IPC(HPLC) indicated disappearance of the starting material (alcohol). For work-up, isopropyl acetate (400 mL) was added to the reaction mixture, followed by the slow addition of a half-saturated aq. sodium bicarbonate solution (400 mL). Caution was exercised as the addition was exothermic, gas evolution takes place. The phases were separated and the aqueous phase was extracted with isopropyl acetate (400 mL). The organic layers were combined and extracted with water (400 mL). The organic layer was dried on magnesium sulfate and the solvent was evaporated at 40-45° C. under reduced pressure. The residue was dried over night in vacuo at 25° C. to obtain 83.25 g crude product as colorless oil. HPLC analysis indicated the presence of 81 a % desired product and 18.6 a % of the corresponding silanole. The crude product was used without further purification for the next step. NMR and HR-MS of a purified sample confirmed the proposed structure. HR-MS: calculated for $C_{33}H_{43}NO_5Si$: $[M+H]^+$: 562.29833; $[M+NH_4]^+$: 579.32488; $[M+Na]^+$: 584.28027. Found: $[M+H]^+$: 562.29848; $[M+NH_4]^+$: 579.32489; $[M+Na]^+$: 584.27995.

1A(3) Preparation of Compound 4
(S)-Benzyl 2-((((9H-fluoren-9-yl)methoxy)carbonyl) amino)-5-((tert-butyldiphenylsilyl)oxy)pentanoate 83.25 g crude product from the previous step (corresponding to 70 g theoretical yield of compound 2, 124.6 mmol) was dissolved in dichloromethane (650 mL) and trifluoroacetic acid (358.8 g, 99% purity, 3115 mmol) was added dropwise to the intensively stirred solution. IPC (HPLC) after 30 minutes indicated complete cleavage of the BOC protecting group. The reaction mixture (clear solution) was transferred into a 6 L 4-bottomed flask with mechanical stirrer and was diluted with 1000 mL of dichloromethane. Aqueous half saturated sodium carbonate solution (1800 mL) was slowly added to the intensively stirred solution. Caution was exercised as strong gas evolution was observed during addition of sodium carbonate. pH of the aqueous phase after completion of the addition: 9-10. The reaction mixture was stirred for additional 15 minutes and the phases were separated. The aqueous phase was extracted with dichloromethane (1000 mL) and the organic layers were combined to obtain a solution of the product in dichloromethane.

The solution was concentrated at 40-45° C. under reduced pressure to a final volume of ca. 650 mL. for the next step.

HPLC indicated the presence of 80.5% of compound 3 and 19.5 a % silanole in the solution.

For FMOCylation, saturated aq. sodium bicarbonate solution (650 mL) was slowly added to the intensively stirred solution of compound 3, followed by the addition of FMOC-chloride (36.55 g, 97% purity, 137 mmol). Caution was exercised as gas evolution was observed during the addition of FMOC-Cl. Stirring was continued for 15 minutes at room temperature. An IPC(HPLC) of the organic layer indicated disappearance of the intermediate compound 3 and complete conversion into compound 4. For work-up, the layers were separated and the aqueous phase was extracted with dichloromethane (650 mL). The organic layers were combined and were extracted with water (650 mL). The organic layer was dried over magnesium sulfate and the solvent was removed at 40-45° C. under reduced pressure to obtain 112.6 g crude product.

The crude product was suspended in ethanol/isopropanol/water (89:5:6; 2400 mL) and the suspension was heated to IT 50° C. to obtain a solution. The solution was cooled down to 45° C., seed crystals were added and the temperature was continued to cool down to 20-25° C. within 1 hour. Crystallization started at ca. 40° C. The suspension was stirred at 20-25° C. over night, then cooled down to IT 0-5° C. within 30 minutes and stirring was continued for additional 2 hours at 0-5° C. The product was isolated by filtration, the filter cake was washed with ethanol/isopropanol/water (89:5:6; 240 mL) and dried under reduced pressure to obtain pure compound 4 (100 a % purity according to HPLC). Yield: 66 g (77.4%). The product was fully characterized by MS and NMR HR-MS: Calculated for $C_{43}H_{45}NO_5Si$: $[M+H]^+$: 684.31398; $[M+NaH_4]^+$: 701.34053; $[M+Na]^+$: 706.29592. Found: $[M+H]^+$: 684.31392; $[M+NH_4]^+$: 701.34021; $[M+Na]^+$: 706.29539. The mother liquor gave 30.6 g of a foam comprising 30 a % product and 29 a % silanole according to HPLC.

1A(4) Preparation of Synthon 1 from Compound 4
(S)-2-((((9H-Fluoren-9-yl)methoxy)carbonyl)amino)-5-((tert-butyldiphenylsilyl)oxy)pentanoic acid Compound 4 (66 g, 96.6 mmol) was suspended in ethanol/isopropylalcohol/water (89:5:6; 3000 mL) and the suspension was heated to IT 45° C. to obtain a solution. The solution was cooled down to IT 30° C. After inertization with Argon, palladium-catalyst (10% on barium sulfate; 6.6 g) was added to the solution under an argon stream. The product was then hydrogenated under a hydrogen pressure slightly above the atmospheric pressure at 30-35° C. The hydrogenation was completed after 1.5 h according to HPLC. The reaction mixture was filtered over a cellulose based filter aid (Cellflock 40; cellulose based filtering aid) and the filter aid was washed with ethanol/isopropanol/water (89:5:6; 600 mL). Evaporation of the solvent under reduced pressure at 45-50° C. gave 59.58 g foam as crude product. The crude product was purified by chromatography on silica gel in 2 portions (2×1 kg silica gel 60) using dichloromethane/methanol 95:5 to 80:20 as mobile phase. Yield: 52 g (90.6%). The product was fully characterized by MS and NMR. HR-MS: Calculated for $C_{36}H_{39}NO_5Si$ $[M+H]^+$: 594.26703; $[M+NH_4]^+$: 611.29358; $[M+Na]^+$: 616.24897. Found: $[M+H]^+$: 594.26743; $[M+NH_4]^+$: 611.29385; $[M+Na]^+$: 616.24900.

35

(ii) Alternative 2

Reaction Scheme 2:

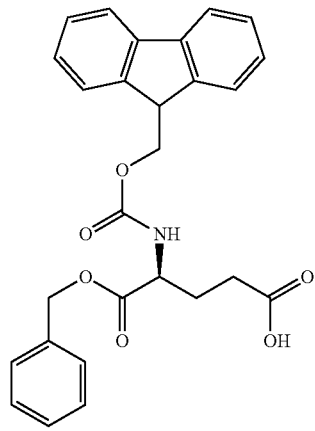

Fmoc-Glu-OBzl (Commercial)

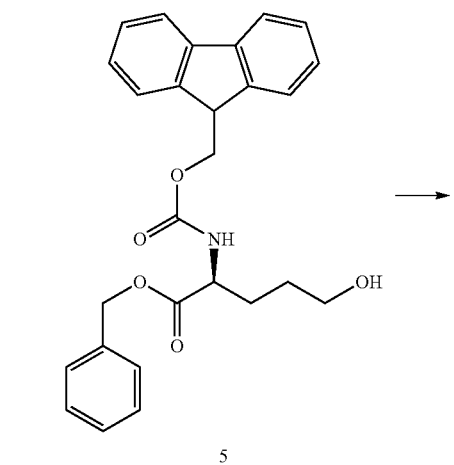

5

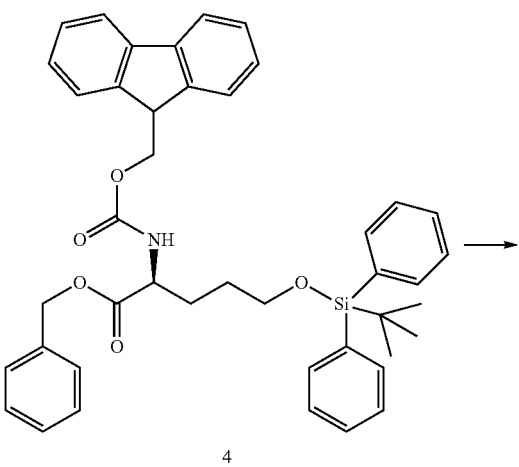

4

36

-continued

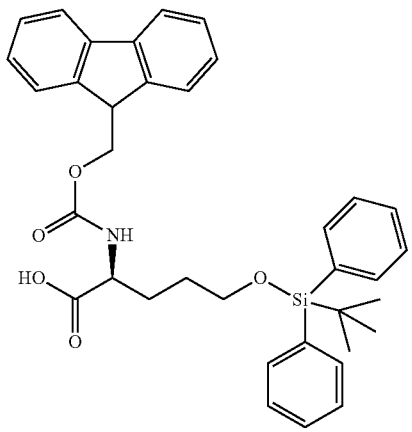

Synthon 1

1A(5) One-Pot Preparation of Compound 4 from Fmoc-Glu-OBzl Via Compound 5

Fmoc-Glu-OBzl (5 g, 10.88 mmol) was dissolved in tetrahydrofurane (80 mL) and triethylamine (3.3 g, 32.6 mmol) was added. The solution was cooled down to −15° C. and ethyl chloroformate (7.3 g, 67.27 mmol) was added to the solution over 30 minutes at −12° C. The suspension thus obtained was stirred for an additional hour at −10 to −15° C. and the temperature was elevated to 0° C. Water (80 mL) was added dropwise to the reaction mixture, maintaining the temperature at 0° C. Sodium borohydride (total 0.805 g, 21.27 mmol) was added in 3 portions (1 portion every 10 minutes) at 0° C. and the reaction mixture was stirred for additional 1 h at 0° C. Caution was exercised as hydrogen gas evolved. The reaction mixture was diluted with water (100 mL) and extracted with isopropyl acetate (150 mL) and the layers were separated. The aqueous phase was extracted again with isopropyl acetate (100 mL) and the organic layers were combined. The combined organic phase was washed with half saturated sodium chloride solution (2×50 mL) and the solution was concentrated at reduced pressure to a final volume of ca. 50 mL. The concentrated solution was clear-filtered and the filter residue was washed with isopropyl acetate (20 mL). The solution of compound 5 thus obtained was transferred into a round bottomed flask and imidazole (1.49 g, 21.89 mmol) was added. The mixture was stirred for 15 min at Rt and tert.-butyl-diphenyl-silyl-chloride (4.45 g, 16.19 mmol) was added. The reaction mixture was stirred for 15 h at rt. For work-up, the suspension was diluted with isopropyl acetate (20 mL) and extracted with water (3×50 mL). The organic layer was separated and the solvent was evaporated under reduced pressure to obtain 9.95 g crude product. The crude product was purified by column chromatography on silicagel with isopropyl acetate/hexane (2:8) as mobile phase to obtain 6.5 g of a solid, which was suspended in hexane and stirred for 3 h at rt. The precipitate was isolated by filtration and dried at 50° C. under reduced pressure to obtain 5.6 g of compound 4. Yield: 75% over two steps. HR-MS: calculated for $C_{43}H_{45}NO_5Si$: $[M+H]^+$: 684.31398; $[M+NH_4]^+$: 701.34053; $[M+Na]^+$: 706.29592. Found: $[M+H]^+$: 684.31430; $[M+NH_4]^+$: 701.34073; $[M+Na]^+$: 706.29577.

1A(6) Alternative One-Pot Preparation of Compound 4 from Fmoc-Glu-OBzl Via Compound 5 Using Isopropyl-Chloroformate Instead of Ethyl-Chloroformate Fmoc-Glu-OBzl (60 g, 130.579 mmol) was dissolved in tetrahydrofuran (550 mL) and triethylamine (40.8 g, 403.202 mmol) was added. A cloudy solution was obtained with some precipitate. This cloudy solution/suspension was transferred into a dropping funnel and was added to a pre-cooled solution of isobutyl-chloroformate (54.96 g, 402.41 mmol) in tetrahydrofuran (300 mL) in a 4.5 L reactor at −35 to −30° C., maintaining this temperature during the addition. Residuals in the dropping funnel were washed with additional tetrahydrofuran (50 mL) and the reaction mixture was stirred at −35 to −30° C. for another 2 hours. Water (960 mL) was added to the reaction mixture within 45 minutes, allowing the temperature to increase until 0° C. A suspension was formed. Sodium borohydride (14.4 g, 380.625 mmol) was added in 20 portions within 1 h at 0° C. and the reaction mixture was stirred for an additional hour at 0° C. Caution was exercised as hydrogen gas evolved.

The suspension was poured onto t-butyl-methylether (600 mL) and the reaction flask was washed with water (600 mL), which was added to the product mixture (2-phases). The phases were separated, the water phase was extracted with t-butyl-methylether (600 mL) and the organic phases were combined. The organic phase was washed with water (2×600 mL), dried over anhydrous magnesium sulfate (200 g) and the solvent was removed under reduced pressure until a final volume of 1 L was achieved. The solution was diluted with dimethyl-formamide (600 g) and the solvent was evaporated under reduced pressure, until a final volume of 400 mL is achieved. The solution of compound 5 thus obtained was transferred into a round bottomed flask. Imidazole (14.4 g, 211.524 mmol) was added to the DMF solution of compound 5 and the mixture was stirred for 5 minutes at rt. Finally, TBDPS-Cl (39.6 g, 144.07 mmol) is added dropwise during 20 minutes at 20-25° C. and the reaction mixture is stirred for an additional hour at this temperature.

The reaction mixture was then poured onto ethyl acetate (1200 mL) and the mixture was extracted with water (700 mL). The layers were separated and the organic layer was washed with water (3×300 mL). Evaporation of the solvent under reduced pressure gave 106 g crude product.

The crude product (106 g) was dissolved in Ethanol/Isopropanol/Water (89:5:6; 1200 mL) at 40-50° C. and seed crystals (0.5 g compound 4) were added. The mixture was allowed to cool down to room temperature and stirred for 17 hrs at rt. The suspension was cooled to −20° C. and stirred for 2 hrs at −20° C. The product was isolated by filtration, the filter cake was washed with the solvent mixture Ethanol/Isopropanol/Water (89:5:6; 3×200 mL) and dried at 40° C. under reduced pressure to obtain 66.5 g of compound 4 (74.6% yield over 2 steps). HPLC indicated >99 a % purity for the product.

Additional product can be isolated from the mother liquor (34 g after evaporation of the solvent), which contains ca. 30 a % compound 4 according to HPLC.

1B Synthesis of Precursor Peptide 1 by SPPS

Precursor Peptide 1: Isobutyryl-Gln(Trt)-Thr(Ile-Tyr(tBu)Me-Ile-Synthon 1-H)-Leu-OH

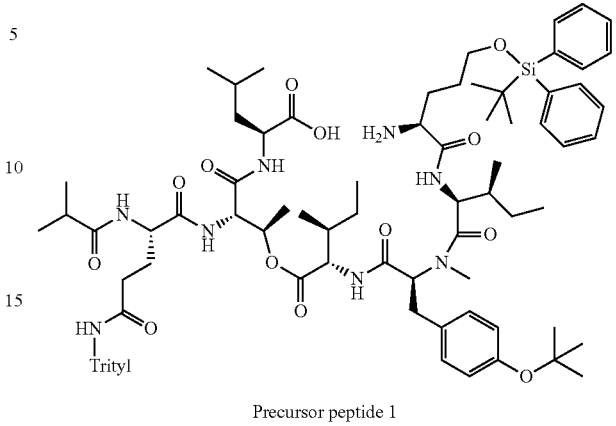

Precursor peptide 1

Precursor Peptide 1 has been Prepared Using 2 Different Solid Supports

Equipment:

Solid phase synthesis reactor with a filter cloth or sintered glass filter plate at the bottom. A nitrogen manifold allows to drain the reactor contents via filter cloth or sintered glass filter plate and bottom valve.

1B(1) Coupling of the Trityl-Linker to the Solid Support 200 g of Aminomethyl-polystyrene resin (crosslinked with 1% divinyl benzene, loading of aminomethyl groups 1 mmol/g) (supplier: Senn Chemicals AG, Dielsdorf/Switzerland) were stirred alternately with several portions of dimethylformamide (1600 mL) and isopropanol (1600 mL) After two final washes with dimethlyformamide, the resin was treated with a previously prepared solution of 4-hydroxy-diphenylmethyl-benzoic acid (91.3 g 300 mmol), 1-hydroxy-benzotriazole monohydrate (45.9 g, 300 mmol) and diisopropylcarbodiimide (75.7 g, 600 mmol) in dimethylformamide (1600 mL). The reaction mixture was stirred for 1.5 h and a Ninhydrin test was performed. The test still showed free amino groups and thus diisopropylcarbodiimide (7.6 g, 60 mmol) was added and the reaction stirred over night. A further ninhydrin test in the morning was negative and the reaction mixture was filtered off. The resin was washed with dimethylformamide and isopropanol alternatingly. The resin was dried in vacuo and yielded 257 g of dry linker-resin. The material was used for the next synthesis step without further analysis.

1B(2) Coupling of Fmoc-Leu-OH

Preparation of Fmoc-Leu-Linker-Resin

Linker-Resin (190 g, 147.8 mmol) was swollen by stirring in toluene (1400 mL). The solvent was filtered off and replaced by a solution of toluene (1400 mL) and acetyl chloride (53 mL, 1478 mmol). This mixture was stirred for 2 h, filtered off, replaced by an identical mixture which was stirred for another 2 h before filtering off. The chlorinated resin was washed twice with toluene and three times with dichloromethane.

In a round bottom flask, a solution of Fmoc-Leu-OH (104.8 g, 296 mmol) and of N-Methylmorpholine (49 mL, 444 mmol) in dichloromethane (600 mL) was prepared. This solution was added to the resin and stirred over night. In the morning, the solution was filtered of and the resin was washed with dichloromethane and isopropanol alternatingly. The resin 0was dried in vacuo and yielded 234.7 g of dry Fmoc-Leu-linker-Resin. The loading with Fmoc-groups was determined at 0.787 mmol/g what led to a yield of 185 mmol (125% of theory). Amino acid analysis at an external contractor confirmed <0.1% D-Leu enantiomer.

1B(3) Coupling of Fmoc-Thr-OH
Preparation of Fmoc-Thr-Leu-Linker-Resin

Fmoc-Leu-Linker-Resin (140 g, 109 mmol) was swollen by stirring in two successive portions of dimethylformamide (1100 mL) for 30 min each.

Fmoc protecting group was cleaved by two subsequent washings of 20% piperidine in dimethylformamide for 5 min and 15 min respectively. The resin was washed by several alternating washes with dimethylfomamide and isopropanol. Phenolphtalein and water were added to a sample of the final wash solution. The absence of pink colour confirmed successful removal of piperidine.

The resin was washed with tetrahydrofurane (1200 mL) three times to prepare for the following coupling step.

In a round bottomed flask a solution of Fmoc-Thr-OH (112.1 g, 328 mmol), hydroxybenzotriazole monohydrate (51.25 g, 334 mmol) and diisopropylcarbodiimide (51 mL, 655 mmol) in tetrahydrofuran (600 mL) was prepared The solution was added to the resin and the pH checked immediately (pH=6.5). The reaction mixture was stirred for 1.5 h until a ninhydrin test showed complete reaction. The solution was filtered off and the resin was washed with dimethylformamide and isopropanol alternatingly. A small sample of the resin was dried and sent for amino acid analysis (0.13% D-Leu, <0.1% D-Thr, <0.1% L-allo-Thr, <0.1% D-allo-Thr), the bulk of the material was subjected to the next step without further drying.

1B(4) Coupling of Fmoc-Gln(Trt)-OH
Preparation of Fmoc-Gln(Trt)-Thr-Leu-Linker-Resin The Fmoc-Thr-Leu-Linker-Resin from the previous step was swollen by stirring in two subsequent portions of dimethylformamide (1100 mL) for 30 min each.

Fmoc protecting group was cleaved by two subsequent washings with 20% piperidine in dimethylformamide for 5 min and 15 min respectively. The resin was washed by several alternating washes with dimethylfomamide and isopropanol. Phenolphtalein and water were added to a sample of the final wash solution. The absence of pink colour proved successful removal of piperidine.

The resin was washed with dimethylformamide (1100 mL) three times to prepare for the following coupling step.

In a round bottomed flask a solution of Fmoc-Gln(Trt)-OH (138.6 g, 226 mmol), HATU (86.2 g, 226 mmol) and Ethyldiisopropylamine (58.4 g, 452 mmol) in dimethylformamide (400 mL) was prepared.

The solution was added to the resin and the pH checked immediately (pH=10). The reaction mixture was stirred for 3 h until a ninhydrin test showed complete reaction. The solution was filtered of and the resin was washed with dimethylformamide and isopropanol alternatingly.

The resin was dried in vacuo and yielded 170 g of dry Fmoc-Gln(Trt)-Thr-Leu-Linker-Resin. The loading with Fmoc-groups was determined at 0.60 mmol/g indicating a yield of 102 mmol (94% of theory over the last two steps). Amino acid analysis at an external contractor led to the following values: (0.13% D-Leu, <0.1% D-Thr, <0.1% L-allo-Thr, <0.1% D-allo-Thr, <0.8% D-Gln).

1B(5) Coupling of Isobutyric Acid
Preparation of Isobutyryl-Gln(Trt)-Thr-Leu-Linker-Resin Fmoc-Gln(Trt)-Thr-Leu-Linker-Resin (169 g, 101 mmol) was swollen by stirring in two subsequent portions of dimethylformamide (1300 mL) for 30 min each.

Fmoc protecting group was cleaved by two subsequent washings with 20% piperidine in dimethylformamide (1300 mL) for 5 min and 15 min respectively. The resin was washed by several alternating washes with dimethylfomamide and isopropanol. Phenolphtalein and water were added to a sample of the final wash solution. The absence of pink colour proved successful removal of piperidine.

The resin was washed with dimethylformamide (1100 mL) three times to prepare for the following coupling step.

In a round bottom flask a solution of Isobutyric acid (17.9 g, 203 mmol), PyBOP (105.5 g, 203 mmol) and Ethyldiisopropylamine (52.4 g, 406 mmol) in dimethylformamide (550 mL) was prepared.

The solution was added to the resin and the pH checked immediately (pH=9.5). The reaction mixture was stirred for 2.5 h until a ninhydrin test showed complete reaction. The solution was filtered off and the resin was washed with dimethylformamide and isopropanol alternatingly.

The batch was directly subjected to the next step without drying and further analysis.

1B(6) Coupling of Fmoc-Ile-OH (Esterification)
Preparation of Isobutyryl-Gln(Trt)-Thr(Ile-Fmoc)-Leu-Linker-Resin Isobutyryl-Gln(Trt)-Thr-Leu-Linker-Resin (wet from step above, 101 mmol) was swollen by stirring in three subsequent portions of dichloromethane (1200 mL) for 20 min each. The solvent was filtered off and MSNT (88 g, 297 mmol) and Fmoc-Ile-OH (105 g, 297 mmol) were added as solids. Dichloromethane (500 mL) was added as well as a solution of N-methyl imidazole (18.2 g, 223 mmol) and ethyldiisopropyamine (51.2 g, 396 mmol) in dichloromethane (100 mL) The reaction mixture was stirred for 2 h until HPLC in process control showed complete reaction. The solution was filtered off and the resin was washed with three portions of dichloromethane, three portions of dimethylformamide and three portions of isopropanol subsequently. The resin was dried in vacuo and yielded 172 g of dry Isobutyryl-Gln(Trt)-Thr(Ile-Fmoc)-Leu-Linker-Resin. Fmoc loading was determined to be 0.418 mmol/g thus indicating a yield of 72 mmol (71% over the last two steps).

1B(7) Coupling of Fmoc-N-methyl-Tyr(tBu)-OH
Preparation of Isobutyryl-Gln(Trt)-Thr(Ile-Tyr(tBu)Me-Fmoc)-Leu-Linker-Resin (Previously Named: Isobutyryl-Gln(Trt)-Thr(Ile-N-me-Tyr(tBu)-Fmoc)-Leu-Linker-Resin)

Isobutyryl-Gln(Trt)-Thr(Ile-Fmoc)-Leu-Linker-Resin (172 g, 72 mmol) was swollen by stirring in two subsequent portions of dimethylformamide (1300 mL) for 30 min each. Fmoc protecting group was cleaved by two subsequent washings with 20% piperidine in dimethylformamide (1400 mL) for 5 min and 15 min respectively. The resin was washed by several alternating washes with dimethylfomamide and isopropanol. Phenolphtalein and water were added to a sample of the final wash solution. The absence of pink colour proofed successful removal of piperidine.

The resin was washed with dimethylformamide (1100 mL) three times to prepare for the following coupling step.

A solution of Fmoc-N-methyl-Tyr(tBu)-OH (68.7 g, 144 mmol) and HATU (55.1 g, 144 mmol) in dimethylformamide (700 mL) was prepared and added to the peptide-resin, followed by the addition of a solution of Ethyl-diisopropylamine (37.5 g 289 mmol) in dimethylformamide (100 mL) under stirring. pH checks immediately after addition of the coupling solution and after 1 h of reaction gave the same result (pH 10) The solution was stirred for 2 h until a ninhydrin test showed complete reaction. The solution was filtered of and the resin was washed with dimethylformamide and isopropanol alternatingly.

The batch was directly subjected to the next step without drying and further analysis.

1B(8) Coupling of Fmoc-Ile-OH
Preparation of Isobutyryl-Gln(Trt)-Thr(Ile-Tyr(tBu)Me-Ile-Fmoc)-Leu-Linker-Resin. (Previously Named: Isobutyryl-Gln(Trt)-Thr(Ile-N-me-Tyr(tBu)-Ile-Fmoc)-Leu-Linker-Resin.)

The wet Isobutyryl-Gln(Trt)-Thr(Ile-Tyr(tBu)Me-Fmoc)-Leu-Linker-Resin (72 mmol) was swollen by stirring in two subsequent portions of dimethylformamide (1200 mL and 1300 mL) for 30 min each. Fmoc protecting group was cleaved by two subsequent washings with 20% piperidine in dimethylformamide (1400 mL) for 5 min and 15 min respectively. The resin was washed by several alternating washes with dimethylfomamide and isopropanol. Phenolphtalein and water were added to a sample of the final wash solution. The absence of pink colour proved successful removal of piperidine.

The resin was washed with dimethylformamide (1100 mL) three times to prepare for the following coupling step.

In a round bottom flask a solution of Fmoc-Ile-OH (103.9 g, 294 mmol) COMU (125.9 g, 294 mmol) and Ethyldiisopropylamine (76 g, 588 mmol) in dichloromethane (440 mL) and dimethylformamide (440 mL) was prepared.

The solution was added to the resin and the reaction mixture stirred for 20 h. After that time a ninhydrin test was done, showing complete reaction. The solution was filtered off and the resin was washed with dimethylformamide and isopropanol alternatingly.

The resin was dried in vacuo and yielded 185.5 g of dry Isobutyryl-Gln(Trt)-Thr(Ile-Tyr(tBu)Me-Ile-Fmoc)-Leu-Linker-Resin. The loading with Fmoc groups was determined to be 0.40 mmol/g. Thus a quantitative yield of 74 mmol resulted.

1B(9) Coupling of Synthon 1 and Cleavage of Final Fmoc Protecting Group
Preparation of Isobutyryl-Gln(Trt)-Thr(Ile-Tyr(tBu)Me-Ile-Synthon 1-H)-Leu-Linker-Resin
(Previously Named: Isobutyryl-Gln(Trt)-Thr(Ile-N-me-Tyr-Ile-Synthon 1-H)-Leu-Linker-Resin)

Isobutyryl-Gln(Trt)-Thr(Ile-Tyr(tBu)Me-Ile-Fmoc)-Leu-Linker-Resin (30 g, 12 mmol) was swollen by stirring in two subsequent portions of dimethylformamide (240 mL and 250 mL) for 30 min each.

Fmoc protecting group was cleaved by two subsequent washings with 20% piperidine in dimethylformamide (250 mL) for 5 min and 15 min respectively. The resin was washed by several alternating washes with dimethylfomamide and isopropanol. Phenolphtalein and water were added to a sample of the final wash solution. The absence of pink colour proved successful removal of piperidine.

The resin was washed with dimethylformamide (250 mL) three times to prepare for the following coupling step.

In a round bottom flask, a solution of synthon 1 (14.6 g, 24.6 mmol) PyBOP (12.85 g, 24.6 mmol) and Ethyldiisopropylamine (6.4 g, 49.2 mmol) in dimethylformamide (120 mL) was prepared.

The solution was added to the resin and the reaction mixture stirred for 3 h. After that time a ninhydrin test confirmed complete reaction. The solution was filtered off and the resin was washed with dimethylformamide and isopropanol alternatingly.

The resulting peptide-resin was swollen by stirring in two subsequent portions of dimethylformamide (250 mL) for 30 min each.

Fmoc protecting group was cleaved by two subsequent washings with 20% piperidine in dimethylformamide (250 mL) for 5 min and 15 min respectively. The peptide-resin was washed by several alternating washes with dimethylfomamide and isopropanol. Finally the peptide-resin was washed three times with dichloromethane (250 mL) to prepare for the cleavage of the peptide.

1B(10) Cleavage of Precursor Peptide 1 from Solid Support
Preparation of Isobutyryl-Gln(Trt)-Thr(Ile-Tyr(tBu)Me-Ile-Synthon 1-H)-Leu-OH (=Precursor Peptide 1)
(Previously Named: Isobutyryl-Gln(Trt)-Thr(Ile-N-M-Tyr(tBu)-Ile-Synthon 1-H)-Leu-OH)

To the wet Isobutyryl-Gln(Trt)-Thr(Ile-Tyr(tBu)Me-Ile-Synthon 1-H)-Leu-Linker-Resin, a mixture of acetic acid (125 mL) and dichloromethane (125 mL) was added and the suspension stirred for 2 h. The suspension was filtered and the filtrate collected in a round bottomed flask (filtrate 1). The resin was washed twice with dichloromethane (250 mL) and the washes were combined with filtrate 1.

The resin was treated with a fresh portion of acetic acid (125 mL) and dichloromethane (125 mL) for another 2 h. The suspension was filtered and the filtrate collected in a round bottomed flask (filtrate 2). The resin was washed twice with dichloromethane (250 mL) and the washes combined with filtrate 2.

Acetic acid (200 mL) and dichloromethane (50 mL) were added to the resin and the suspension stirred over night. The suspension was filtered and the filtrate collected as filtrate 3.

The three filtrates were worked up separately to assess the effectiveness of the cleavage method. The filtrates were concentrated in a rotary evaporator and the residual acetic acid removed by azeotropic distillation with three portions of toluene (100 mL). The oily residues were then dried in high vacuo at a lyophilisator. Yield: filtrate 1: 12.5 g, filtrate 2: 2.1 g, filtrate 3: 0.3 g.

The crude material, Precursor peptide 1, was purified by RP-chromatography, the fractions concentrated in a rotary evaporator and the concentrate freeze dried. Purity: 98.8% Yield: 8.5 g (48% for the last two steps). The product was characterized by, $^1$H-NMR, $^{13}$C-NMR and HR-MS. The spectra confirmed the proposed structure. The NMR spectra indicated the presence of several conformations.

HR-MS: calculated for $C_{85}H_{116}N_8O_{13}Si$: $[M+H]^+$: 1485.85039. Found: $[M+H]^+$: 1485.84929.

Second SPPS-Synthesis of Precursor Peptide 1 Using a Chlorinated Resin

1B(11) Immobilization of the First Amino Acid (Fmoc-Leu-OH)

2-Chlorotrityl chloride resin (30 g, L=1.2 mmol/g; Merck Novabiochem 855017) was swelled with 240 ml of dried DCM for 10 min and then the solvent was drained, the solid phase reactor was kept close under a soft nitrogen stream. In the meantime, in a round bottom flask were mixed Fmoc-Leu-OH (42.6 g, 120.8 mmol) and 100 ml of dry 1,4-Dioxane. The solvent was evaporated under vacuum at 45° C., then a second portion of 1,4 dioxane was added. The solvent was evaporated again under vacuum at 45° C. until a colorless oil residue was obtained. To this oily residue were then added sequentially dry DCM (155 mL) and DIPEA (40.4 mL), the solution was added in one single portion to the pre-swollen resin and then 5 min later a second portion of DIPEA (16.5 mL) was added. The suspension was stirred for 2 h and the reaction medium was drained. In order to quench potential non-reacted chloride, 240 ml of a quenching solution of DCM/MeOH/DIPEA (70/15/15, v/v) was added and the mixture was stirred for 10 min. A loading of 0.95 mmol/g was measured.

General Protocol for Fmoc Cleavage:

To the pre-swollen resin were added 240 ml of a solution of 25% piperidine in DMF, the suspension was stirred for 5 minutes and then the reaction mixture was removed by filtration, then a second portion of the same solution of piperidine was added, the suspension was stirred for 15 minutes and then the solvent was removed by filtration.

Resin washing with drying down:
The resin was washed as follows:
250 ml of DMF (6×2 min)
250 ml of IPA (3×2 min)
250 ml of TBME (6×2 min)

The resin was dried overnight under vacuum at 40 C.° to obtain 35.7 g of H-Leu-Resin.

1B(12): SPPS Synthesis of H-Thr-Leu-Resin H-Leu-Resin (30 g) from the previous step was swollen with 270 ml of DMF for 30 min then the solvent was drained.

In a round bottomed flask (RBF) were mixed Fmoc-Thr-OH (25.0 g, 73.2 mmol), BOP (40.4 g, 91.5 mmol) and DMF (250 mL), the mixture was stirred for 2 min and then DIPEA (18.9 g, 146.4 mmol) was added. The mixture thus obtained was added in one portion to the pre-swollen peptide-resin and the reaction mixture was stirred for 2.5 h. The Kaiser test was positive and therefore a second coupling was done according to the conditions previously described. After 1.0 h the Kaiser test was negative and the reaction was considered to be complete and the reaction medium was removed via filtration.

The resin was washed as follows:
250 ml DMF (4×2 min)
250 ml IPA (3×2 min)
250 ml TBME (5×2 min).

The resin was dried over night under vacuum at 40 C.° yielding 52.2 g of Fmoc-Thr-Leu-Resin ready for the Fmoc-cleaving step.

Fmoc Cleavage:

The resin (52.2 g) was suspended in 272 ml of DMF and stirred for 1.0 h then the solvent was removed by filtration.

The Fmoc protecting group was cleaved in the same manner as described for 1B(11) and the peptide-resin was washed as follows:
250 ml DMF (6×2 min)
250 ml IPA (3×2 min)
250 ml TBME (6×2 min)

The resin was dried overnight under vacuum at 40 C.° yielding 39.9 g of H-Thr-Leu-Resin 1B(13): SPPS Synthesis of H-Gln(Trt)-Thr-Leu-Resin H-Thr-Leu-Resin from the previous step (39.9 g) was swollen with 270 ml of DMF for 30 min then the solvent was drained.

In an RBF were mixed Fmoc-Gln(Trt)-OH (44.7 g, 73.2 mmol), BOP (40.4 g, 91.5 mmol) and 250 ml of DMF. The mixture was stirred for 2 min and then DIPEA (18.9 g, 146.4 mmol) was added. The resulting mixture was added in one portion to the pre-swollen H-Thr-Leu-Resin and the reaction mixture was stirred for 2.5 h, the Kaiser test was negative, then the reaction was considered to be complete and the reaction medium was removed via filtration.

The resin was washed as follows:
250 ml DMF (4×2 min)
250 ml IPA (3×2 min)
250 ml DMF (4×2 min)

The wet peptide-resin was used for the Fmoc-cleaving step without any further manipulation.

Fmoc Cleavage:

The fmoc protecting group was cleaved according to the procedure described in step 1B(11). Then the resin was washed as follows:
250 ml DMF (4×2 min)
250 ml IPA (3×2 min)
250 ml TBME (5×2 min)

The resin was dried overnight under vacuum at 40 C.° yielding 54.4 g of H-Gln(Trt)-Thr-Leu-Resin.

1B(14): SPPS Synthesis of Isobutyryl-Gln(Trt)-Thr-Leu-Resin

The peptide-resin from the previous step (54.4 g) was swollen with 270 ml of DMF for 30 min, then the solvent was drained.

In a RBF were mixed Isobutyric acid (6.4 g, 73.2 mmol), PyBop (38.1 g, 73.2 mmol) and 230 ml of DMF, the mixture was stirred for 2 min and then DI PEA (28.3 g, 219.6 mmol) was added. The solution was added in one portion to the pre-swollen peptide-resin and the reaction mixture was stirred for 1.5 h. The Kaiser test was negative, then the reaction was considered to be complete and the reaction medium was removed via filtration.

The resin was washed as follows:
250 ml DMF (4×2 min)
250 ml IPA (3×2 min)
250 ml TBME (5×2 min).

The resin was dried overnight under vacuum at 40 C.° yielding 55.8 g of Isobutyryl-Gln(Trt)-Thr-Leu-Resin.

1B(15): SPPS Synthesis of Isobutyryl-Gln(Trt)-Thr(Ile-H)-Leu-Resin

The peptide-resin coming from the previous step (55.8 g) was suspended in 250 ml of dry DCM for 1.0 h. Then the solvent was removed by filtration and the wet peptide-resin was kept under a soft stream of nitrogen and the temperature was adjusted to 0-5° C.

In a RBF were mixed Fmoc-Ile-OH (51.7 g, 146.4 mmol), and 150 ml of dry dioxane. The solvent was evaporated under vacuum at 45° C. until an oily residue was observed. The distillation process was repeated and then to the residue were added 150 ml of dried DCM, the solution was cooled to −10° C. and MSNT (43.3 g, 146.4 mmol) was added, the suspension was stirred for 3 min and then N-methyl-imidazole (14.2 g, 173 mmol) was added, the mixture was stirred for 2 min and the solution was added dropwise in 10 min to the above prepared peptide-resin. After the addition was finished the suspension was stirred under a nitrogen atmosphere for 2.0 h The resin was washed as follows:
250 ml DMC (4×2 min)
250 ml DMF (3×2 min)

The wet peptide-resin was used for the Fmoc-cleaving step without any further manipulation.

Fmoc Cleavage:

The Fmoc protecting group was cleaved according to the general protocol described in 1B(11)

After the Fmoc cleavage was done, the resin was washed as follows:
250 ml DMF (5×2 min)
250 ml IPA (3×2 min)
250 ml TBME (5×2 min)

The resin was dried overnight under vacuum at 40 C.° yielding 57.2 g of Isobutyryl-Gln(Trt)-Thr(O-Ile-H)-Leu-Resin.

1B(16): SPPS Synthesis of Isobutyryl-Gln(Trt)-Thr(O-Ile-Tyr(tBu)MeN)-Leu-Resin

The peptide-resin coming from the previous step (57.2 g) was suspended in 250 ml DMF for 30 min. for swelling, then the solvent was removed by filtration.

In a RBF were mixed Fmoc-NMeTyr(tBu)-OH (52.0 g, 109.8 mmol), HATU (41.7 g, 109.8 mmol) and 230 ml of DMF and the mixture was stirred for 2 min. Then DI PEA (28.3 g, 219.6 mmol) was added and the solution was stirred for 2.0 min. The resulting solution was then added to the pre-swollen peptide-resin.

The reaction mixture was stirred for 1.0 h and a Kaiser-test was performed. The Kaiser test was negative. The reaction was considered to be complete and the reaction medium was removed via filtration.

The peptide-resin was washed as follows:
250 ml DMF (4×2 min)
250 ml IPA (1×2 min)

The wet peptide-resin was used for the Fmoc-cleaving step without any further manipulation.

Fmoc Cleavage:

The Fmoc protecting group was cleaved according to the general protocol used in 1B(11).

After the Fmoc cleavage was done, the resin was washed as follows:
250 ml DMF (5×2 min)
250 ml IPA (1×2 min)
250 ml DMF (5×2 min)

The obtained isobutyryl-Gln(Trt)-Thr(Ile-Tyr(tBu)Me-H)-Leu-Resin was used for the next step without drying.

1B(17): SPPS Synthesis of Isobutyryl-Gln(Trt)-Thr(Ile-Tyr(tBu)Me-Ile-H)-Leu-Resin Isobutyryl-Gln(Trt)-Thr(Ile-Tyr(tBu)Me-H)-Leu-Resin from the previous step was swollen with 270 ml of DMF for 30 min, then the solvent was drained.

In a round bottomed flask were mixed Fmoc-Ile-OH (38.8 g, 109.8 mmol), HATU (41.7 g, 109.8 mmol) and DMF (250 mL), the mixture was stirred for 2 min and then DI PEA (28.3 g, 219.6 mmol) was added. The solution was added in one portion to the pre-swollen peptide-resin and the reaction mixture was stirred for 2.0 h, The Chloranil test was positive and then a second coupling with Fmoc-Ile-OH was performed. 3 h after the second coupling, the peptide-resin was isolated by filtration.

The peptide-resin was washed as follows:
250 ml DMF (4×2 min)
250 ml IPA (3×2 min)
250 ml DMF (4×2 min)

The wet peptide-resin was used for the Fmoc-cleaving step without any further manipulation.

Fmoc Cleavage:

The Fmoc protecting group was removed in the same manner as described in 1B(11), and the peptide-resin was washed as follows.
250 ml DMF (5×2 min)
250 ml IPA (3×2 min)
250 ml TBME (4×2 min).

The peptide-resin was dried overnight under vacuum at 40 C.° yielding 67.0 g of Isobutyryl-Gln(Trt)-Thr(I le-Tyr(tBu)Me-Ile-H)-Leu-Resin.

1B(18): SPPS Synthesis of Isobutyryl-Gln(Trt)-Thr(Ile-Tyr(tBu)Me-Ile-Synthon 1-H)-Leu-Resin Isobutyryl-Gln(Trt)-Thr(Ile-Tyr(tBu)Me-Ile-H)-Leu-Resin from the previous step (33.5 g) was suspended in 150 ml of DMF for 30 min then the solvent was drained. In a RBF were mixed Fmoc-Synthon 1-OH (34.3 g, 57.8 mmol), PyBop (30.0 g, 57.7 mmol) and 113 ml of DMF, the mixture was stirred for 2 min and then DIPEA (14.9 g, 115.2 mmol) was added. The solution was added in one portion to the pre-swollen peptide-resin and the reaction mixture was stirred for 2.0 h. The reaction medium was removed by filtration.

The peptide-resin was washed as follows:
150 ml DMF (4×2 min)
150 ml IPA (3×2 min)
150 ml DMF (4×2 min)

The wet peptide-resin was used for the Fmoc-cleaving step without any further manipulation.

Fmoc Cleavage:

The Fmoc protecting group was removed in the same way as in 1B(11) but using 150 ml of the piperidin solution, and the peptide-resin was washed as follows.
150 ml DMF (5×2 min)
150 ml IPA (3×2 min)
150 ml TBME (4×2 min)

The peptide-resin was dried overnight under vacuum at 40 C.° yielding 36.0 g of Isobutyryl-Gln(Trt)-Thr(Ile-Tyr(tBu)Me-Ile-Synthon 1-H)-Leu-Resin.

1B(19): Alternative SPPS Synthesis: Cleavage of Peptide from Solid Support

Isobutyryl-Gln(Trt)-Thr(Ile-Tyr(tBu)Me-Ile-Synthon 1-H)-Leu-Resin from the previous step (29.75 g) was treated with 350 ml of dried DCM for 1.0 h, the solvent was removed by filtration and then 350 ml of a solution of 30% v/v HFIP in DCM was added. The mixture was stirred for 10 min and then the solvent was removed by filtration and kept aside. To the wet resin was added a second portion of the same HFIP solution and the solution was stirred for 10 min, then the solvent was removed by filtration and pooled with the previous solution. The resin was washed 3 times with DCM (350 ml) and the washes were combined with the cleavage solutions.

The combined solution was concentrated under vacuum until an oily residue was observed and then 200 ml of toluene was added, the solvent was evaporated under reduced pressure at 45° C. until an oily residue was obtained. 350 ml of hexane was added and the suspension was stirred for 2 h. The solvent was removed by filtration and the filter cake was washed with hexane (50 ml), the wet cake was dried overnight under vacuum at 35° C. to yield 19.24 g of crude precursor peptide 1 (=Isobutyryl-Gln(Trt)-Thr(Ile-Tyr(tBu)Me-Ile-Synthon 1-H)-Leu-OH).

Part of the crude precursor peptide 1 (6.0 g) was purified by RP-chromatography, the product fractions were concentrated in a rotary evaporator and the concentrate was freeze dried to obtain 2.2 g of pure precursor peptide 1 in 99.3% a purity. Product containing side fractions were treated similarly to obtain additional 1.25 g of less pure precursor peptide in 71.4% a purity. Extrapolated for the whole amount of crude precursor peptide 1 (19.24 g), this would correspond to 7.05 g pure precursor peptide 1 from major fractions and additional 4.01 g precursor peptide 1 (in 71.4% a purity) from side fractions.

1C Solution Phase Synthesis of Compound 8
Reaction Scheme 3
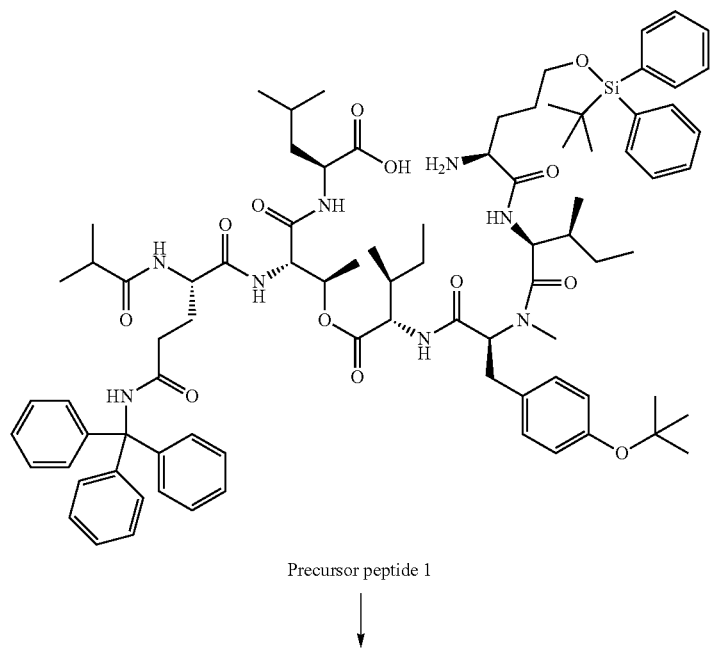
Precursor peptide 1
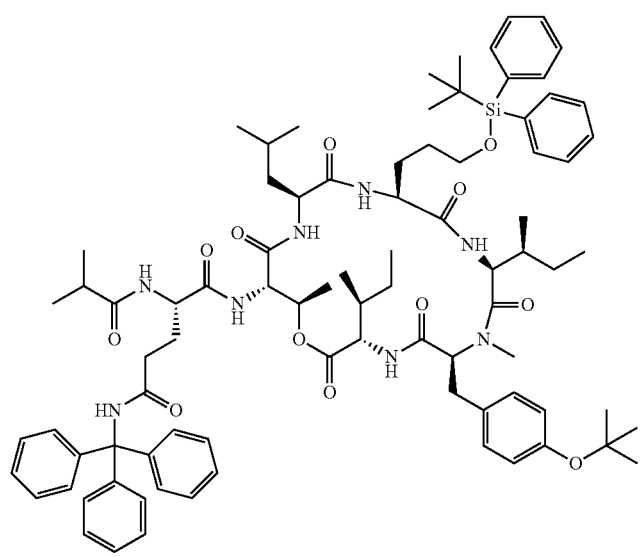
Compound 6

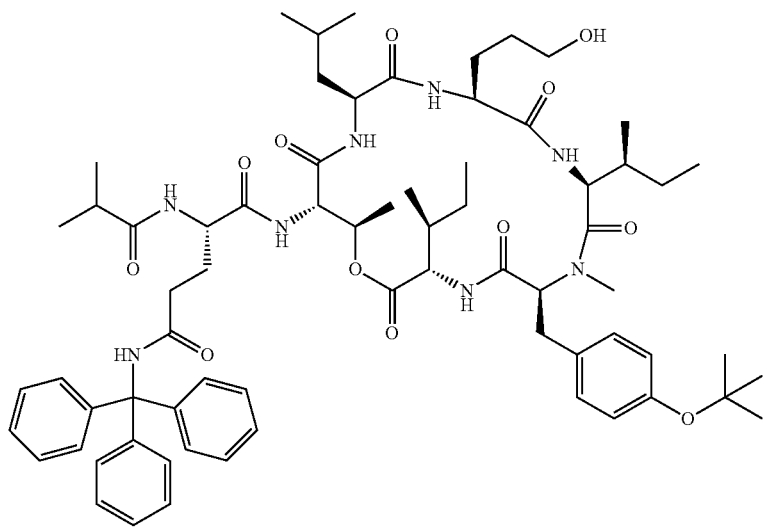

Compound 7

1C(1) Synthesis of Compound 6

(S)—N$^1$-((3S,6S,9S,12S,15S,18S,19R)-6-(4-(tert-butoxy)benzyl)-3,9-di((S)-sec-butyl)-12-(3-((tert-butyldiphenylsilyl)oxy)propyl)-15-isobutyl-7,19-dimethyl-2,5,8,11,14,17-hexaoxo-1-oxa-4,7,10,13,16-pentaazacyclononadecan-18-yl)-2-isobutyramido-N$^5$-tritylpentanediamide A cloudy solution/suspension of Precursor peptide 1 (1.9 g, 1.28 mmol) in acetonitrile (120 mL) was added during 90 min to a stirred mixture of HATU (972 mg, 2.56 mmol) and DMAP (468.6 mg, 3.84 mmol) in acetonitrile (100 mL) at 35° C. The dropping funnel was washed with acetonitrile (30 mL). An IPC(HPLC) after the addition of the suspension indicated the absence of the precursor peptide and the completion of the cyclization. For work-up, the solvent was evaporated under reduced pressure until a final volume of ca. 50 mL and the residue was diluted with isopropyl acetate (250). The organic phase was extracted with water (2×100 mL) and the solvent was evaporated under reduced pressure to obtain 2.3 g of crude product. The crude product was purified by flash-chromatography on silicagel with ethyl acetate as mobile phase to obtain 1.79 g (1.22 mmol) compound 6 as a foam. Yield: 95%. The product was characterized by, $^1$H-NMR $^{13}$C-NMR and HR-MS. The spectra confirmed the proposed structure. NMR spectra indicated the presence of several conformations.

HR-MS: calculated for C$_{85}$H$_{114}$N$_8$O$_{12}$Si: [M+H]$^+$: 1467.83983; [M+NH$_4$]$^+$:1484.86637; [M+Na]$^+$: 1489.82177. Found: [M+H]$^+$:1467.83984; [M+NH$_4$]$^+$: 1484.86555; [M+Na]$^+$: 1489.82073.

Second Example for the Synthesis of Compound 6 (15 g Scale)

A solution of the precursor peptide 1 (15.0 g) in t-butyl-methyl-ether (750 mL) was added slowly during 1.5 h to a pre-cooled solution of DMAP (2.80 g) and HATU (5.87 g) in acetonitrile (375 mL) at 0° C. The reaction mixture was stirred for additional 30 min at room temperature. The reaction mixture was then diluted with t-butyl-methyl-ether (750 mL) and poured onto half-saturated aq. NaCl-solution (1500 mL). The phases were separated and the organic phase was extracted again with half-saturated aq. NaCl-solution (1500 mL). The organic layer was separated and the solvent was partly evaporated under reduced pressure to a final volume of ca. 175 mL. This solution was filtered over silica gel (column with 225 g silica gel) using t-butyl-methyl-ether as mobile phase. Evaporation of the solvent and drying in vacuo at 40-45° C. gave compound 6 in 97.53% purity according to HPLC. Yield: 14.19 g (95.7%).

1C(2) Synthesis of Compound 7

(S)—N$^1$-((3S,6S,9S,12S,15S,18S,19R)-6-(4-(tert-butoxy)benzyl)-3,9-di((S)-sec-butyl)-12-(3-hydroxypropyl)-15-isobutyl-7,19-dimethyl-2,5,8,11,14,17-hexaoxo-1-oxa-4,7,10,13,16-pentaazacyclononadecan-18-yl)-2-isobutyramido-N$^5$-tritylpentanediamide Compound 6 (1.79 g, 1.22 mmol) was dissolved in tetrahydrofurane (60 mL) and Et$_3$N(HF)$_3$ (6.62 g, 41.1 mmol) was added at room temperature. The reaction mixture was stirred at room temperature for 8.5 hours, then diluted with isopropyl acetate (200 mL), and the resulting solution/suspension was slowly added to an intensively stirred saturated aq. NaHCO$_3$-solution. The organic phase was separated and extracted with water (100 mL). Evaporation of the solvent under reduced pressure gave 1.86 g crude product, which was purified by flash-chromatography on silica gel with ethyl acetate/isopropanol (95:5) as mobile phase to obtain 1.24 g (1.00 mmol) of compound 7.

Yield: 82%.

The product was fully characterized by IR, NMR and MS. The spectra confirmed the proposed structure.

HR-MS: calculated for $C_{69}H_{96}N_8O_{12}$: [M+H]$^+$: 1229.72205; [M+NH$_4$]$^+$: 1246.74860; [M+Na]$^+$: 1251.70399. Found: [M+H]$^+$: 1229.72128; [M+NH$_4$]$^+$: 1246.74780; [M+Na]$^+$: 1251.70310.

Second Example for the Preparation of Compound 7 (14 g Scale)

Compound 6 (14.0 g, 9.537 mmol) was dissolved in tetrahydrofuran (220 mL) and t-butyl-methyl-ether (116 mL) was added. The solution was treated with Et$_3$N(HF)$_3$ (23.05 g) by slow addition within 10 minutes. The reaction mixture was stirred for 24 h at room temperature. For work-up the reaction mixture was diluted with t-butyl-methyl-ether (570 mL) and the mixture was poured onto half saturated aq. NaHCO$_3$-solution (632 mL). The biphasic mixture was stirred for 30 min and the phases were separated. The organic phase was extracted with water (280 mL). Both aqueous phases were extracted with t-butyl-methyl-ether (380 mL) and the organic phases were combined. The organic phase was dried over anhydrous MgSO$_4$ (8.0 g) and the solvent was partly evaporated under reduced pressure to a final volume of ca. 100 mL. Toluene (140 mL) was added and the solvent was evaporated again to a final volume of 80 mL. This solution was diluted with t-butyl-methyl-ether (70 mL) and the product was precipitated by slow addition of heptanes (140 mL) during 30 min. The formed suspension was heated to 50-55° C. and stirred for 30 min at this temperature. The suspension was then cooled down to 0° C. within 30 min, stirred at 0° C. for 2 h and the product was isolated by filtration. The product, a white precipitate, was dried in vacuo to obtain 11.08 g of compound 7. (94.5% yield). HPLC of the product indicated 97 a % purity.

1C(3) Synthesis of Compound 8 (See Reaction Scheme 4 for Structure)

(S)—N$^1$-((3S,6S,9S,12S,15S,18S,19R)-6-(4-(tert-butoxy)benzyl)-3,9-di((S)-sec-butyl)-15-isobutyl-7,19-dimethyl-2,5,8,11,14,17-hexaoxo-12-(3-oxopropyl)-1-oxa-4,7,10,13,16-pentaazacyclononadecan-18-yl)-2-isobutyramido-N$^5$-tritylpentanediamide Compound 7 (1.2 g, 0.98 mmol) was dissolved in a mixture of tetrahydrofuran (190 mL) and dimethyl sulfoxide (62 mL). 1-Hydroxy-1,2-benziodoxol-3(1H)-one 1-oxide (IBX) (2.42 g, 45% g/g, 3.9 mmol) was added and the solution was stirred for ca. 4.5 hours, after which time HPLC indicated disappearance of the starting material (compound 7). The reaction mixture was then poured onto saturated, aq. NaHCO$_3$-solution (300 mL) and was extracted with dichloromethane (2×300 mL). The organic layers were combined and were washed with water (2×300 mL). Evaporation of the solvent under reduced pressure gave 2.31 g of crude product as a foam. The crude product was purified by flash-chromatography on silicagel with ethyl acetate/isopropanol (95:5) to obtain 1.16 g of a product mixture, comprising at least 2 products with the desired mass in LC-MS. The product mixture was used as such for the next step.

HR-MS (major isomer): calculated for $C_{69}H_{94}N_8O_{12}$: [M+H]$^+$: 1227.70640; [M+NH$_4$]$^+$: 1244.73295; [M+Na]$^+$: 1249.68834. Found: [M+H]$^+$: 1227.70599; [M+NH$_4$]$^+$: 1244.73200; [M+Na]$^+$: 1249.68733.

HR-MS (minor isomer): calculated for $C_{69}H_{94}N_8O_{12}$: [M+H]$^+$: 1227.70640; [M+NH$_4$]$^+$: 1244.73295; [M+Na]$^+$: 1249.68834. Found: [M+H]$^+$: 1227.70598; [M+NH$_4$]$^+$: 1244.73198; [M+Na]$^+$: 1249.68751.

Second Example for the Synthesis of Compound 8 (10 g Scale)

Compound 7 (10.0 g, 8.13 mmol) was dissolved in tetrahydrofuran (127 mL) and dimethylsulfoxide (42 mL). To this solution, 1-Hydroxy-1,2-benziodoxol-3(1H)-one 1-oxide (IBX) (15.18 g, 45% m/m, 24.4 mmol) was added under intense stirring at room temperature. The reaction mixture was stirred for 16 h at room temperature. The reaction mixture was then poured onto aq. NaHCO$_3$-solution (500 mL) and ethyl acetate (250 mL) was added. The biphasic mixture was stirred for 30 minutes and the layers were separated. The organic phase was washed with half-saturated aq. NaCl-solution (250 mL) and the layers were separated. The water layers were extracted with ethyl acetate ((250 mL) and the organic phases were combined. The combined organic phase was dried on anhydrous magnesium sulfate and the solvent was partly evaporated to obtain ca. 50 g solution. This solution was flashed over a silica gel column (100 g silica gel) using ethyl acetate/methanol (98:2 v/v) as mobile phase. The product solution (537.4 g) thus obtained was treated with toluene (135 mL) and the resulting solution was concentrated to 112 g final weight by partly evaporation of the solvent at 45° C. under reduced pressure. The resulting solution was cooled to 0° C. and heptanes (135 mL) was added during 30 min. The suspension thus obtained was stirred for 1 h at 0° C., the product was isolated by filtration and washed with heptanes (2×30 mL). Finally the product was dried in vacuo at 45° C. over night to obtain 8.824 g of a mixture of compound 8 and its hemiaminal-isomers. Yield: 88.4%.

1D Synthesis of Compound A
(S)—N¹-((2S,5S,8S,11R,12S,15S,18S,21R)-2,8-di-(S)-sec-butyl-21-hydroxy-5-(4-hydroxybenzyl)-15-isobutyl-4,11-dimethyl-3,6,9,13,16,22-hexaoxo-10-oxa-1,4,7,14,17-pentaazabicyclo[16.3.1]docosan-12-yl)-2-isobutyramidopentanediamide
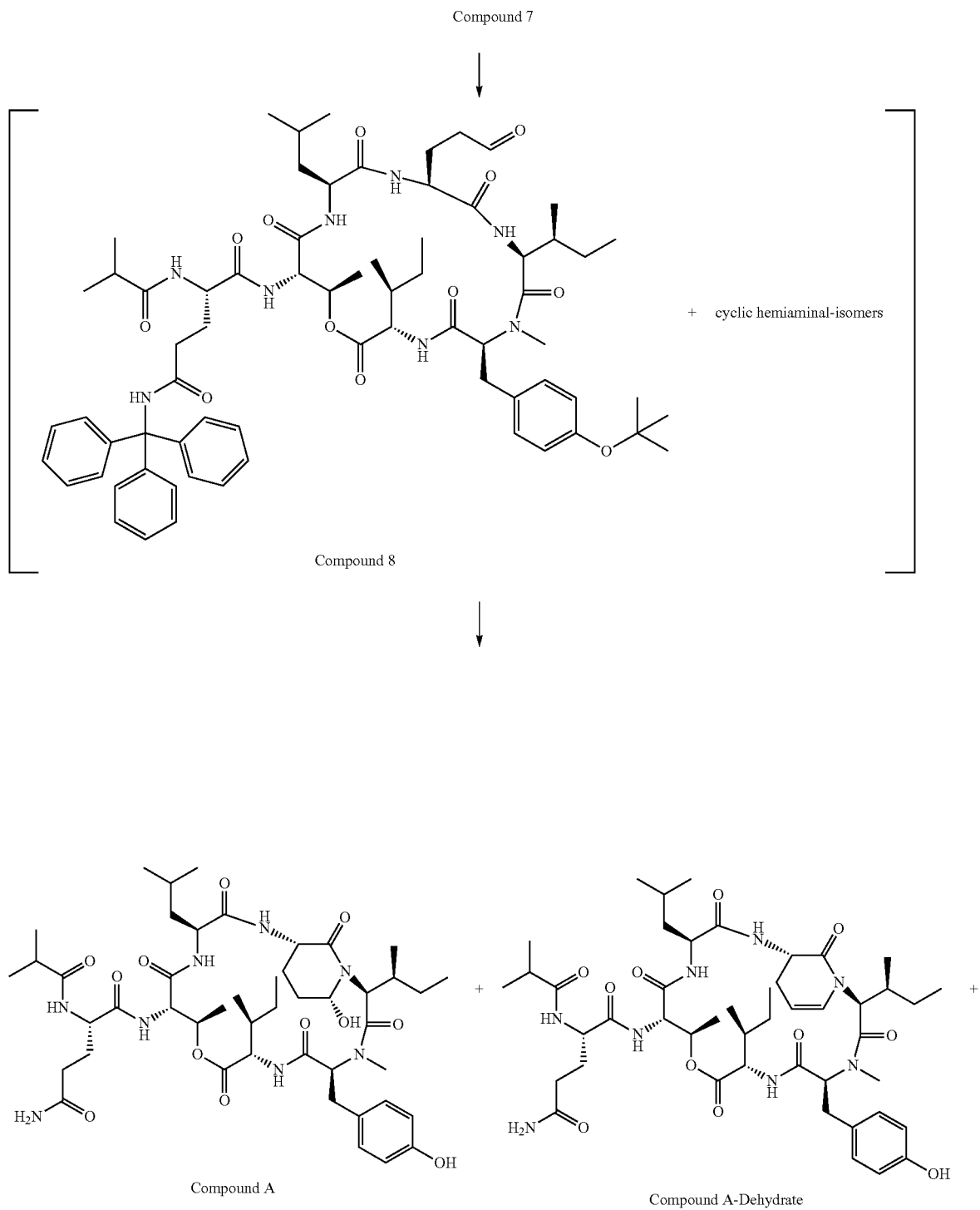

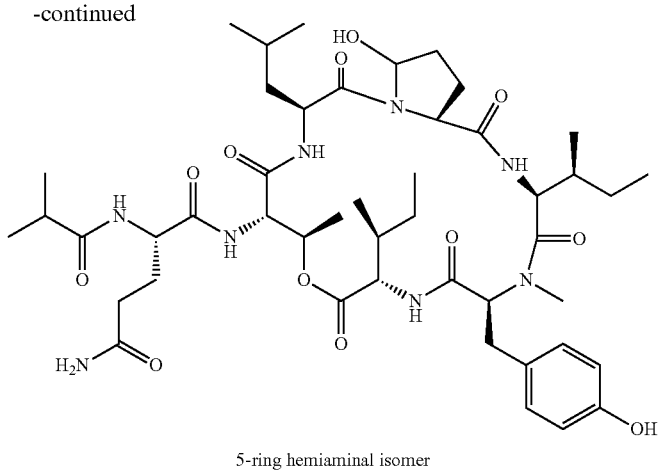

5-ring hemiaminal isomer

Compound 8 (2.0 g) was dissolved in dichloromethane (400 mL) and the solution was cooled down to 0° C. Trifluoroacetic acid (115.9 g) was added to the stirred solution at 0° C. and the reaction mixture was stirred for 4 h at 0° C. Dichloromethane (400 mL) was added at this temperature, followed by the addition of water (20 g). The reaction mixture was allowed to warm-up to room temperature and stirring was continued for additional 5 hours at room temperature. For work-up, the reaction mixture was poured onto a stirred solution of sodium acetate (165.1 g) in water (800 mL) and ethyl acetate (400 mL) was added to obtain a solution. The upper layer (aqueous phase) was removed and the lower organic phase (dichloromethane phase) was washed with water (2×200 mL). The water layers were extracted with ethyl acetate (200 mL) and the organic layers were combined. The solvent was removed under reduced pressure to obtain crude Compound A as a mixture of 5- and 6-ring isomers (see Reaction Scheme 5), accompanied by trityl alcohol and other byproducts of the reaction.

The crude product was purified by RP-chromatography on Silica Kromasil 100-10-C8 with a gradient of acetonitrile/water as mobile phase. The product containing fractions were evaporated to remove acetonitrile, the precipitate was dissolved in ethyl acetate and the solvent was removed under reduced pressure to obtain 0.895 g of compound A; yield: 59.1%. The product was fully characterized by NMR and MS and the spectra of the product were identical to Compound A from fermentation.

HR-MS: Calculated for $C_{46}H_{72}O_{12}N_8$: $[M+H]^+$: 929.53425; $[M+NH_4]^+$: 946.56080; $[M+Na]^+$: 951.51619. Found: $[M+H]^+$: 929.53445; $[M+NH_4]^+$: 946.56129; $[M+Na]^+$: 951.51624.

$^1$H-NMR (600 MHz, $d_6$-DMSO) $\delta_H$: −0.11 (3H, d, J=6.2 Hz), 0.64 (4H, m), 0.77 (3H, d, J=6.2 Hz), 0.81 (3H, t, J=7.3 Hz), 0.84 (3H, d, J=7.0 Hz), 0.88 (3H, d, J=6.6 Hz), 1.02 (3H, d, J=6.7 Hz), 1.02 (1H, m), 1.03 (3H, d, J=6.7 Hz), 1.09 (1H, m), 1.20 (3H, d, J=6.2 Hz), 1.24 (1H, m), 1.39 (1H, m), 1.51 (1H, m), 1.75 (6H, m), 1.83 (1H, m), 1.92 (1H, m), 2.12 (2H, m), 2.47 (1H, m), 2.58 (1H, m), 2.67 (1H, m), 2.71 (3H, s), 3.16 (1H, d, J=14.2 Hz), 4.30 (1H, m), 4.34 (1H, m), 4.42 (1H, d, J=10.6 Hz), 4.45 (1H, m), 4.61 (1H, d, J=9.2 Hz), 4.71 (1H, dd, J=9.5, 5.5 Hz), 4.93 (1H, s), 5.05 (1H, dd, J=11.4, 2.6 Hz), 5.48 (1H, m), 6.07 (1H, d, J=2.6 Hz), 6.64 (2H, d, J=8.4 Hz), 6.73 (1H, s), 6.99 (2H, d, J=8.4 Hz), 7.25 (1H, s), 7.35 (1H, d, J=9.2 Hz), 7.64 (1H, d, J=9.5 Hz), 7.73 (1H, d, J=9.2 Hz), 8.01 (1H, d, J=7.7 Hz), 8.42 (1H, d, J=8.8 Hz), 9.17 (1H, s).

$^{13}$C-NMR (150 MHz, $d_6$-DMSO) $\delta_C$: 10.35, $CH_3$; 11.21 $CH_3$; 13.85, $CH_3$; 16.00, $CH_3$; 17.68, $CH_3$; 19.52, 2×$CH_3$; 20.89, $CH_3$; 21.75, $CH_2$; 23.30, $CH_3$; 23.74, $CH_2$; 24.21, CH; 24.48, $CH_2$; 27.35, $CH_2$; 29.78, $CH_2$; 30.08, $CH_3$; 31.49, $CH_2$; 33.18, CH; 33.24, $CH_2$; 33.76, CH, 37.41, CH; 39.23, $CH_2$; 48.84, CH; 50.69, CH; 52.11, CH; 54.17 CH; 54.70, CH; 55.31, CH; 60.66, CH; 71.89, CH; 73.97, CH; 115.32, 2×CH; 127.34, Cq; 130.37, 2×CH; 156.27, Cq; 169.12, Cq; 169.29, Cq; 169.37, Cq; 169.79 Cq; 170.65, Cq; 172.40, Cq; 172.53, Cq; 173.87 Cq; 176.38, Cq.

Second Example for the Synthesis of Compound A (8.5 g Scale)

Compound 8 (8.5 g, 6.924 mmol) was dissolved in dichloromethane (595 mL) and the solution was cooled to 0° C. A solution of trifluoroacetic acid (127.5 mL) in dichloromethane (127.5 mL) was added to the cooled solution, maintaining the temperature at 0-5° C. The reaction mixture was stirred for 5.5 h at 0° C. and was diluted with dichloromethane (850 mL), followed by addition of water (42.5 mL). The reaction mixture was allowed to warm up to room temperature and was stirred for 17.5 h at room temperature. For work-up, the reaction mixture was poured onto a stirred, biphasic mixture of aqueous sodium acetate (169 g sodium acetate in 722 g water) and ethyl acetate (700 mL). The phases were separated and the organic phase was washed again with aqueous sodium acetate solution (169 g sodium acetate in 722 g water). The layers were separated and the organic phase was washed with water (2×850 mL). The individual aqueous phases were extracted with ethyl acetate (700 mL) and the organic layers were combined. The organic layer was dried over anhydrous magnesium sulfate and the solvent was partly evaporated at 40-45° C. under reduced pressure to obtain 187 g of a thin suspension. Heptane (187 g) was added within 15 minutes and the suspension formed was cooled to 0° C. The suspension was stirred for 1 h at 0° C. and the product was isolated by filtration. The crude product was dried in vacuo at 40° C. to obtain 5.65 g crude compound A. Crude yield: 87.8%.

0.96 g of the crude product was purified by RP-chromatography on Silica Kromasil 100-10-C8 with a gradient of acetonitrile/water as mobile phase. The product containing fractions were evaporated to remove acetonitrile, the precipitate was dissolved in ethyl acetate and the solvent was partly removed under reduced pressure to obtain 40 g of a solution. Heptane (40 g) was added to the stirred solution during 30 min at room temperature and the resulting suspension was stirred at room temperature for additional 2 h. The product was isolated by filtration and washed with ethyl acetate/heptane (1:1, 2×10 mL). The product was dried in vacuo at 40-45° C. for 16 h to obtain 0.702 g of compound A. Yield after RP-chromatography and precipitation: 64%.

Example 2

Synthesis of Compound B (Nostopeptin BN920)

(S)-2-acetamido-N¹-((1S,2S,5S,8S,11R,12S,15S, 18S,21R)-2-benzyl-21-hydroxy-5-(4-hydroxybenzyl)-15-isobutyl-8-isopropyl-4,11-dimethyl-3,6,9,13, 16,22-hexaoxo-10-oxa-1,4,7,14,17-pentaazabicyclo [16.3.1]docosan-12-yl)pentanediamide Reaction Scheme 5:

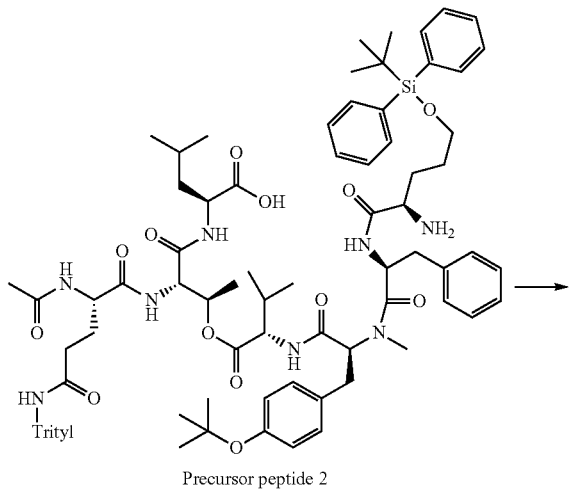

Precursor peptide 2

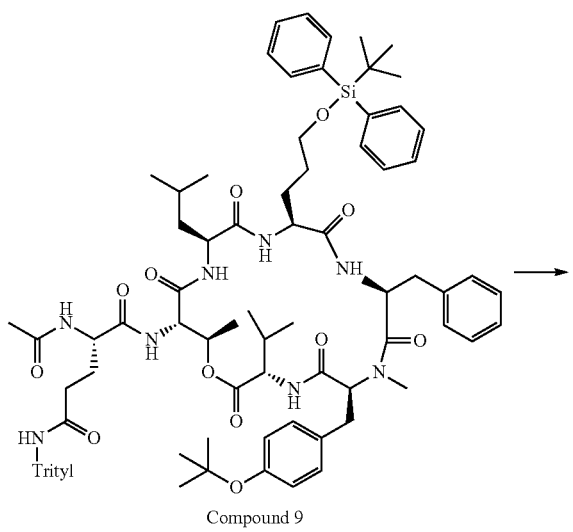

Compound 9

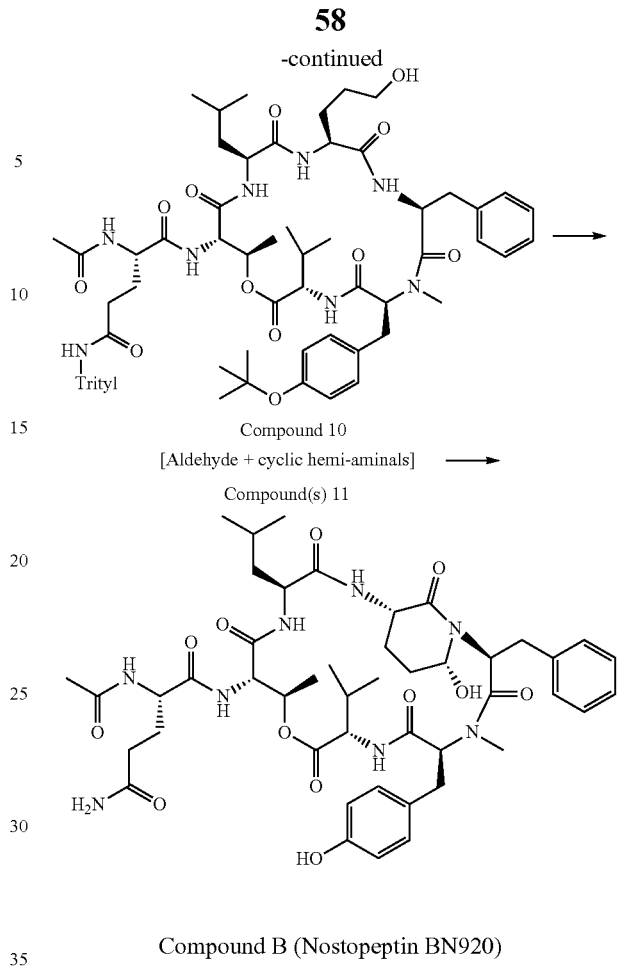

Compound 10

[Aldehyde + cyclic hemi-aminals] ⟶ Compound(s) 11

Compound B (Nostopeptin BN920)

2A Synthesis of Precursor Peptide 2 by SPPS
Ac-Gln(Trt)-Thr(Val-Tyr(tBu)Me-Phe-Synthon1-H)-Leu-OH
Equipment:
Peptide-synthesizer equipped with a 250 ml glass-reactor with frit and manifold for automatic solvent delivery, shaking and sucking off reagents.
2A(1) Synthesis of Fmoc-Thr-Leu-Trt-Tentagel-S
Fmoc-Leu-Trt-Tentagel-S-Resin (18.7 g loading 0.37 mmol/g (supplied by Rapp Polymere GmBH, Tübingen/Germany)) were swollen in DMF by shaking for 30 min.
The Fmoc protecting group was cleaved by two subsequent treatments with 20% piperidine in DMF for 5 min and 15 min respectively. After resin washing by several alternating washes with DMF and isopropanol the complete removal of bases was checked with the absence of a pink color after Phenolphthalein and water addition to the last washing step.
4.7 g of Fmoc-Thr-OH, 5.26 g of HATU and 1.8 g of DIPEA were dissolved in 50 ml of DMF. After 5 min of stirring additional 1.8 g of DI PEA were added. After checking the pH (>11) the mixture was added to the deprotected resin and shaken for 2 h. The performed Kaiser test was OK and the resin was washed by several alternating washes with DMF and isopropanol. After drying the resin weight was 19.01 g. A small sample was cleaved and checked by HPLC. A single main peak showed a successful conversion.
2A(2) Synthesis of Fmoc-Gln(Trt)-Thr-Leu-Trt-Tentagel-S
19.01 g Fmoc-Thr-Leu-Trt-Tentagel-S-Resin (6.6 mmol) were pre-swollen in DMF and the Fmoc protecting group was cleaved by two subsequent treatments of 20% piperidine in DMF for 5 min and 15 min respectively. After resin washing by several alternating washes with DMF and isopropanol the complete removal of bases was checked with the absence of a pink color after Phenolphthalein and water addition to the last washing step.

8.07 g of Fmoc-Gln(Trt)-OH, 5.01 g of HATU and 3.4 g of DIPEA were dissolved in 50 ml of DMF. After checking the pH (>11) the mixture was added to the deprotected resin and shaken for 1.5 h. The performed Kaiser test was OK and the resin was washed by several alternating washes with DMF and isopropanol. The resulting resin was directly used in the following step below, only a small sample was cleaved and checked by HPLC. A single main peak showed successful conversion.

2A(3) Synthesis of Ac-Gln(Trt)-Thr-Leu-Trt-Tentagel-S

The Fmoc-Gln(Trt)-Thr-Leu-Trt-Tentagel-S resin from above was re-swollen in DMF by shaking in DMF for 10 min. The Fmoc protecting group was cleaved by two subsequent treatments with 20% piperidine in DMF for 5 min and 15 min respectively. The resin was washed by several alternating washes with DMF and isopropanol. Phenolphthalein and water were added to a sample of the final wash solution. The absence of pink color proved successful removal of piperidine.

0.774 g of acetic-acid, 6.707 g of PyBOP and 3.33 g of DIPEA were dissolved in 50 ml of DMF. After checking the pH (>11) the mixture was added to the deprotected resin and shaken for 2.5 h. The performed Kaiser test was OK and the resin was washed by several alternating washes with DMF and isopropanol. The resulting resin was directly used in the following step below, only a small sample was cleaved and checked be HPLC. A single main peak showed successful conversion.

2A(4) Synthesis of Ac-Gln(Trt)-Thr(Val-Fmoc)-Leu-Trt-Tentagel-S (Previously Named: Ac-Gln(Trt)-Thr(Val-Fmoc)-Leu-Trt-Tentagel-S)(Side-Chain Esterification)

The Ac-Gln(Trt)-Thr-Leu-Trt-Tentagel-S resin from above was re-swollen in DMF by shaking in DMF for 10 min.

8.7 g of Fmoc-Val-OH and 8.3 g of DIPEA were dissolved in 25 ml of DCM. In parallel 2.76 g of MSNT were dissolved in another 25 ml of DCM. Both solutions were combined and after 3 min pre-activation put to the peptide resin and shaken for 2 h. The resin was washed by several alternating washes with DMF and isopropanol. The resulting resin was directly used in the following step below, only a small sample was cleaved and checked be HPLC. A single main peak showed successful conversion.

2A(5) Synthesis of Ac-Gln(Trt)-Thr(Val-Tyr(tBu)Me-Fmoc)-Leu-Trt-Tentagel-S (Previously Named: Ac-Gln(Trt)-Thr(Val-N-me-Tyr(tBu)-Fmoc)-Leu-Trt-Tentagel-S)

The Ac-Gln(Trt)-Thr(Val-Fmoc)-Leu-Trt-Tentagel-S resin from above was re-swollen in DMF by shaking in DMF for 10 min.

The Fmoc protecting group was cleaved by two subsequent treatments with 20% piperidine in DMF for 5 min and 15 min respectively. The resin was washed by several alternating washes with DMF and isopropanol. Phenolphthalein and water were added to a sample of the final wash solution. The absence of pink color proved successful removal of piperidine.

6.1 g of Fmoc-N-Me-Tyr(tBu)-OH, 4.8 g of HATU and 3.3 g of DIPEA were dissolved in 50 ml of DMF. After checking the pH (>11) the mixture was added to the deprotected resin and shaken for 2.5 h. The performed Kaiser test was OK and the resin was washed by several alternating washes with DMF and isopropanol. The resulting resin was directly used in the following step below, only a small sample was cleaved and checked be HPLC. A single main peak showed successful conversion.

2A(6) Synthesis of Ac-Gln(Trt)-Thr(Val-Tyr(tBu)Me-Phe-Fmoc)-Leu-Trt-Tentagel-S (Previously Named: Ac-Gln(Trt)-Thr(Val-N-me-Tyr(tBu)-Phe-Fmoc)-Leu-Trt-Tentagel-S)

Ac-Gln(Trt)-Thr(Val-Tyr(tBu)Me-Fmoc)-Leu-Trt-Tentagel-S resin from above was re-swollen in DMF by shaking in DMF for 10 min.

The Fmoc protecting group was cleaved by two subsequent treatments with 20% piperidine in DMF for 5 min and 15 min respectively. The resin was washed by several alternating washes with DMF and isopropanol. Phenolphthalein and water were added to a sample of the final wash solution. The absence of pink color proved successful removal of piperidine.

9.66 g of Fmoc-Phe-OH, 9.48 g of HATU and 6.4 g of DIPEA were dissolved in 100 ml of DMF. After checking the pH (>11) the mixture was added to the deprotected resin and shaken for 2 h. The performed Kaiser test was OK and the resin was washed by several alternating washes with DMF and isopropanol. The resulting resin was directly used in the following step below, only a small sample was cleaved and checked be HPLC. A single main peak showed successful conversion.

2A(7) Synthesis of Ac-Gln(Trt)-Thr(Val-Tyr(tBu)Me-Phe-Synthon1-H)-Leu-OH (Previously named: Ac-Gln(Trt)-Thr (Val-N-me-Tyr(tBu)-Phe-Synthon1-H)-Leu-OH) (=Precursor peptide 2)

Ac-Gln(Trt)-Thr(Val-Tyr(tBu)Me-Phe-Fmoc)-Leu-Trt-Tentagel-S resin from above was re-swollen in DMF by shaking in DMF for 10 min.

The Fmoc protecting group was cleaved by two subsequent treatments with 20% piperidine in DMF for 5 min and 15 min respectively. The resin was washed by several alternating washes with DMF and isopropanol. Phenolphthalein and water were added to a sample of the final wash solution. The absence of pink color proved successful removal of piperidine.

6.77 g of Synthon1, 5.9 g of PyBOP and 2.95 g of DIPEA were dissolved in 100 ml of DMF. After checking the pH (>11) the mixture was added to the deprotected resin and shaken for 2 h. The performed Kaiser test was OK and the resin washed by several alternating washes with DMF and isopropanol. After taking a small sample for a HPLC check, the Fmoc protecting group was cleaved by two subsequent treatments with 20% piperidine in DMF for 5 min and 15 min respectively. The resin was washed by several alternating washes with DMF and isopropanol. Finally the resin was washed two times with DCM. Cleavage of the synthesized peptide from the resin was achieved by shaking in a mixture of 80% of acetic acid in DCM over night. The resulting peptide solution was filtered off and the resin was washed two times with DCM. The combined filtrates were evaporated and finally purified by RP-chromatography using a gradient system. The collected fractions were analyzed by HPLC and the pure fractions were pooled, evaporated and finally lyophilized.

Yield: 3.54 g (42%) Precursor peptide 2.

HR-MS: Calculated for $C_{85}H_{108}N_8O_{13}Si$: $[M+H]^+=$ 1477.78779. Found: $[M+H]^+=1477.78691$.

2B Synthesis of Compound B (S)-2-acetamido-$N^1$-((1S,2S,5S,8S,11R,12S,15S,18S,21R)-2-benzyl-21-hydroxy-5-(4-hydroxybenzyl)-15-isobutyl-8-isopropyl-4,11-dimethyl-3,6,9,13,16,22-hexaoxo-10-oxa-1,4,7,14,17-pentaazabicyclo[16.3.1]docosan-12-yl)pentanediamide

2B(0) Synthesis of Compound 9

(S)-2-acetamido-$N^1$-((3S,6S,9S,12S,15S,18S,19R)-9-benzyl-6-(4-(tert-butoxy)benzyl)-12-(3-((tert-butyldiphenylsilyl)oxy)propyl)-15-isobutyl-3-isopropyl-7,19-dimethyl-2,5,8,11,14,17-hexaoxo-1-oxa-4,7,10,13,16-pentaazacyclononadecan-18-yl)-$N^5$-tritylpentanediamide The lactamization of Precursor peptide 2 to obtain Compound B was performed under similar conditions described for the preparation of Compound 6. The product, Compound 9, was fully characterized by IR, NMR and MS. The spectra confirmed the proposed structure.

HR-MS: Calculated for $C_{85}H_{106}N_8O_{12}Si$: $[M+H]^+$: 1459.77723; $[M+NH_4]^+$: 1476.80377. Found: $[M+H]^+$: 1459.77719; $[M+NH_4]^+$: 1476.80291.

2B(1) Synthesis of Compound 10

(S)-2-acetamido-$N^1$-((3S,6S,9S,12S,15S,18S,19R)-9-benzyl-6-(4-(tert-butoxy)benzyl)-12-(3-hydroxypropyl)-15-isobutyl-3-isopropyl-7,19-dimethyl-2,5,8,11,14,17-hexaoxo-1-oxa-4,7,10,13,16-pentaazacyclononadecan-18-yl)-$N^5$-tritylpentanediamide The de-silylation reaction to obtain compound 10 was performed under similar conditions described for the preparation of compound 7. The product was fully characterized by IR, NMR and MS. The spectra confirmed the proposed structure.

HR-MS: Calculated for $C_{69}H_{88}N_8O_{12}$: $[M+H]^+$: 1221.65945; $[M+NH_4]^+$: 1238.6860; $[M+Na]^+$: 1243.64139. Found: $[M+H]^+$: 1221.65894; $[M+NH_4]^+$: 1238.68518; $\{M+Na\}^+$: 1243.64001.

2B(2) Synthesis of Compound 11 (Aldehyde)

(S)-2-acetamido-$N^1$-((3S,6S,9S,12S,15S,18S,19R)-9-benzyl-6-(4-(tert-butoxy)benzyl)-15-isobutyl-3-isopropyl-7,19-dim ethyl-2,5,8,11,14,17-hexaoxo-12-(3-oxopropyl)-1-oxa-4,7,10,13,16-pentaazacyclononadecan-18-yl)-$N^5$-tritylpentanediamide The oxidation of Compound 10 to obtain Compound 11 was performed under similar conditions described for the preparation of Compound 8. LC-MS analysis showed several peaks with the desired mass, indicating the presence of a mixture of the aldehyde, 5-ring-hemiaminale and 6-ring-hemiaminale. The mixture was used as such for the next step.
HR-MS (major peak): Calculated for $C_{69}H_{86}N_8O_{12}$: $[M+H]^+$: 1219.64380; $[M+NH_4]^+$: 1236.67035; $[M+Na]^+$: 1241.62574. Found: $[M+H]^+$: 1219.64404; $[M+NH_4]^+$: 1236.67053; $\{M+Na\}^+$: 1241.62524.

2B(3) Synthesis of Compound B (Nostopeptin BN920) from Compound 11

(S)-2-acetamido-$N^1$-((1S,2S,5S,8S,11R,12S,15S,18S,21R)-2-benzyl-21-hydroxy-5-(4-hydroxybenzyl)-15-isobutyl-8-isopropyl-4,11-dimethyl-3,6,9,13,16,22-hexaoxo-10-oxa-1,4,7,14,17-pentaazabicyclo[16.3.1]docosan-12-yl)pentanediamide Compound(s) 11 (1.0 g, 0.82 mmol) was dissolved in dichloromethane (200 mL). Trifluoroacetic acid (57.8 g) was added at 15 to 25° C. during 10 minutes and the reaction mixture was stirred for 45 hours at room temperature. The reaction mixture was then diluted with dichloromethane (200 mL) and water (10 mL) was added. Stirring was continued for additional 24 hours at room temperature. The reaction mixture was poured onto a saturated aq. $NaHCO_3$-solution (700 mL) within 20 minutes and dichloromethane (500 mL), isopropanol (50 mL) and water (500 mL) were added sequentially. The layers were separated and the aqueous layer was extracted with a solution of isopropanol (50 mL) in dichloromethane (500 mL). The layers were again separated and the aqueous layer was extracted several times with dichloromethane (5×300 mL). The organic layers were combined and the solvent was evaporated under reduced pressure to obtain crude product mixture (1.0 g), comprising the desired Nostopeptin BN920 along with trityl alcohol and other byproducts of the reaction. The crude product was purified by silica gel chromatography with dichloromethane/isopropanol as mobile phase to obtain pure Nostopeptin BN920 (212 mg, 97% (A) purity). Collection of less pure fractions gave additional 402 mg Product with 90% (A) purity. Yield from all fractions: 614 mg (81%). The product was fully characterized by IR, NMR and MS. The spectra confirmed the proposed structure.

HR-MS: Calculated for $C_{46}H_{64}N_8O_{12}$: $[M+H]^+$: 921.47165; $[M+NH_4]^+$: 938.49820; $[M+Na]^+$: 943.45359. Found: $[M+H]^+$: 921.47167; $[M+NH_4]^+$: 938.49861; $[M+Na]^+$: 943.45337.

Example 3

Shift of Equilibrium

Reaction Scheme 4 shows the presence of the dehydrate form of Compound A. It has now been discovered that this can be converted easily (back) into Compound A using a simple procedure for hydration of the dehydrate form depicted in the following reaction scheme:

Reaction Scheme 6:

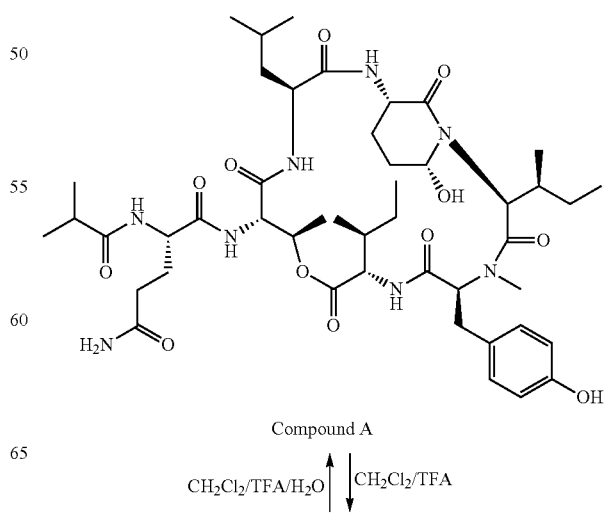

Compound A $CH_2Cl_2/TFA/H_2O$ ↑ ↓ $CH_2Cl_2/TFA$

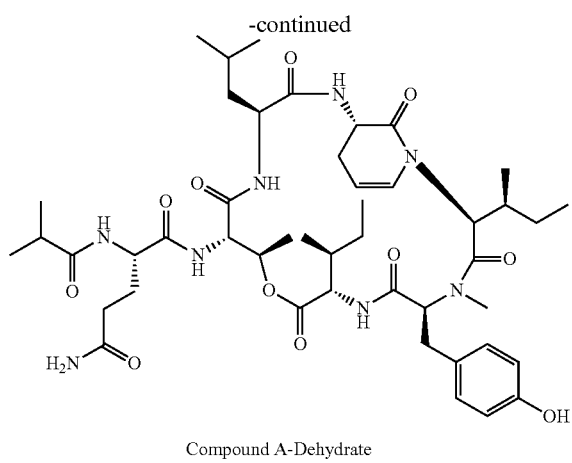

Compound A-Dehydrate

This allows to improve the yield of Compound A in any type of synthesis (be it chemical as in the present disclosure or by use of fermentation as in WO2009/024527).

For example, during cleavage of acid sensitive protecting groups in a compound comprising the ahp-subunit, e.g. Compound A in Example 1, the formation of large amounts of the corresponding dehydrated byproduct is observed. This byproduct is usually separated e.g. by chromatography and disposed. This leads to loss of valuable product and to low yield for this step. For example, if the oxidation product(s) of Compound 8 are subjected to acidic conditions to cleave the trityl- and t-butyl protecting groups (scheme 4), significant amounts of Compound-A-dehydrate are formed as byproduct. Depending on the acid concentration and reaction conditions, Compound-A-dehydrate might be formed even as major product in this product mixture.

For example, a ratio Compound A/Compound A-dehydrate (1:2) was observed when trifluoroacetic acid/dichloromethane (5:95 v/v) was used to cleave the protecting groups after the oxidation step (Example 1).

It was therefore searched for ways to convert the dehydrate byproduct into the desired product. It has now been found that this can be achieved by acid catalyzed equilibration of the product mixture in the presence of water under well defined conditions. Addition of water to the reaction mixture of example 1 and subsequent stirring at room temperature for 19 h gave a product mixture with a ratio Compound A/Compound A-dehydrate of ca. 96:4. Thus, addition of water to the reaction mixture after the acid-catalyzed deprotection step (scheme 4) changed the ratio of Compound A/Compound A-dehydrate from (1:2) under water free conditions to (96:4) after water addition and equilibration.

The formation of Compound A-dehydrate from Compound A under acidic deprotection conditions was confirmed by conversion of pure Compound A into Compound A-dehydrate using trifluoroacetic acid in DCM. Treatment of Compound A with 33% (v/v) TFA in DCM for 2 h at room temperature gave a product mixture of Compound A-dehydrate/Compound A in a ratio of 78:22 according to HPLC. The dehydration could be driven to >95% conversion, when water absorbing agents, such as molecular sieves were added to the reaction mixture. Thus, stirring of pure Compound A in a 1:2 mixture of TFA/DCM in the presence of molecular sieves gave the dehydrated-product in quantitative crude yield and ca. 96 area % HPLC purity (example 3B). There were still ca. 4 area % of Compound A present in the crude product.

Conversion of Compound A-dehydrate from Example 3B into Compound A was demonstrated by stirring Compound A-dehydrate in dichloromethane in the presence of trifluoroacetic acid and water (Example 3C). The product thus obtained comprised 95.6 area % Compound A and only 4.4 area % Compound A-dehydrate according to HPLC.

Reaction Scheme 7:

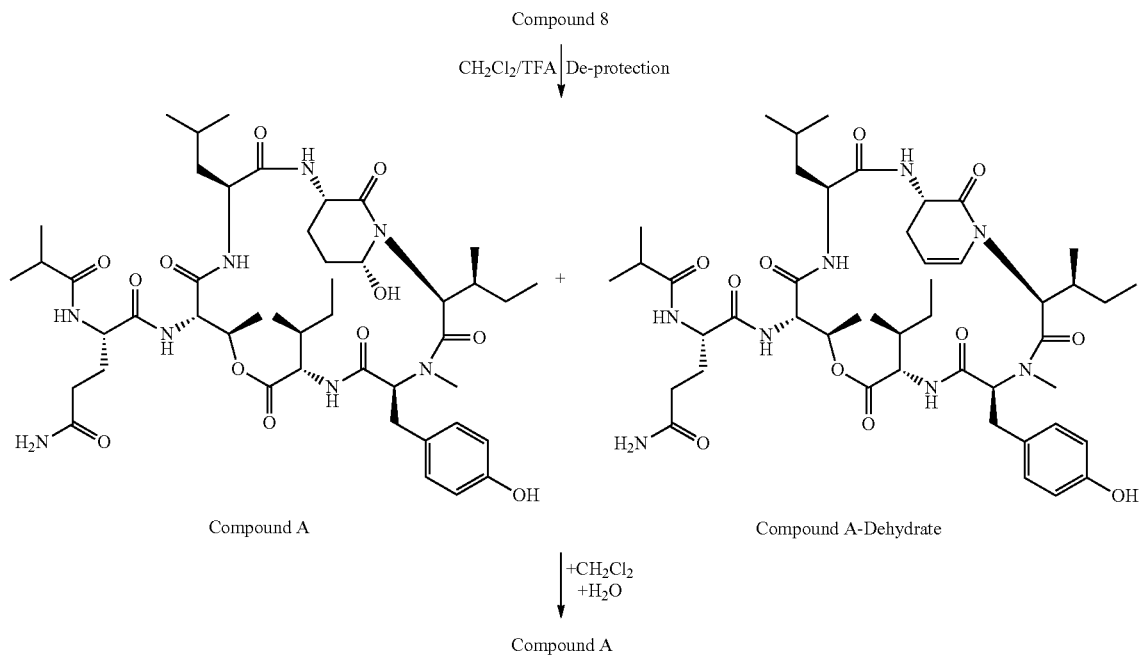

Experimental Details for Example 3

3A 23 mg product mixture from oxidation (compound 8 and cyclic aminals derived from it) was dissolved in DCM (5.7 mL) and TFA (0.3 mL) was added to the solution under intensive stirring. The reaction mixture was stirred for 5 h at room temperature, until an IPC(HPLC) indicated complete cleavage of the protecting groups. Compound A and Compound A-dehydrate were present in the reaction mixture in a ratio of 1:2, along with additional byproducts. The reaction mixture was diluted with DCM (5.7 mL) and the intensively stirred solution was treated with water (0.23 mL). HPLC after 19 h stirring time at room temperature indicated a ratio of 96:4 for Compound A/Compound A-dehydrate.

For workup, the reaction mixture was poured onto a solution of sodium acetate (1.62 g) in water (23 mL) and ethyl acetate (35 mL) was added. The phases were separated and the organic layer was extracted with water (2×25 mL). The water layers were extracted with ethyl acetate (35 mL) and the organic layers were combined. The solvent was evaporated at reduced pressure to obtain 22 mg of crude product as a foam. The crude product was purified by flash chromatography on silica gel with ethyl acetate/methanol 95:5 to 90:10 to obtain Compound A in 96.8 area % purity, accompanied by 1.8 area % of the 5-ring isomer.

3B

Compound A (250 mg) was dissolved in dichloromethane (10 mL) and trifluoroacetic acid (5 mL) was added, followed by the addition of molecular sieves (1 g). IPC(HPLC) after 1 h indicated a ratio of 17:83 for Compound A/Compound A-dehydrate. The reaction mixture was stirred for a total of 72 h at room temperature. For workup, the molecular sieves were removed by filtration and the solution was poured onto saturated aq. $NaHCO_3$-solution. The aqueous layer was extracted with ethyl acetate (50 mL). The organic phase was washed with water (20 mL) and the solvent was evaporated at reduced pressure and the residue was dried in vacuo to obtain quantitative yield (245 mg) crude product as a foam. HPLC analysis of the crude product indicated the presence of Compound A/Compound A-dehydrate at a ratio of ca. 4:96 area %.

HR-MS: calculated for $C_{46}H_{70}N_8O_{11}$ $[M+H]^+$= 911.52368, $[M+NH4]^+$=928.55023, $[M+Na]+$=933.50563. Found $[M+H]^+$=911.52372, $[M+NH4]^+$=928.55029, $[M+Na]^+$=933.50538. The structure of Compound A-dehydrate was confirmed by $^1$H-NMR.

$^1$H-NMR (600 MHz, $d_6$-DMSO) $\delta_H$: 0.06 (3H, d, J=6.6 Hz), 0.67 (3H, t, J=7.3 Hz), 0.70 (3H, d, J=7.0 Hz), 0.77 (3H, d, J=6.6 Hz), 0.81 (1H, m), 0.87 (6H, m), 1.00 (3H, d, J=7.0 Hz), 1.02 (3H, d, J=7.0 Hz), 1.06 (1H, m), 1.16 (3H, d, J=6.5 Hz), 1.17 (1H, m), 1.30 (1H, m), 1.41 (1H, m), 1.53 (1H, m), 1.74 (2H, m), 1.91 (2H, m), 2.01 (1H, m), 2.11 (2H, m), 2.45 (3H, m), 2.73 (3H, s), 2.74 (1H, m), 3.18 (1H, m), 4.32 (2H, m), 4.50 (1H, m), 4.54 (1H, m), 4.64 (1H, d, J=9.5 Hz), 4.77 (1H, d, J=11.0 Hz), 5.18 (1H, m), 5.26 (1H, m), 5.42 (1H, q, J=6.6 Hz), 6.25 (1H, d, J=7.3 Hz), 6.32 (1H, d, J=7.7 Hz), 6.67 (2H, d, J=8.4 Hz), 6.75 (1H, s), 7.04 (2H, d, J=8.4 Hz), 7.25 (1H, s), 7.30 (1H, d, J=8.8 Hz), 7.89 (1H, d, J=9.2 Hz), 7.98 (1H, d, J=8.1 Hz), 8.50 (1H, d, J=8.4 Hz), 9.24 (1H, s).

3C

Compound A-dehydrate (110 mg) from example 2 was dissolved in DCM (20 mL). TFA (1 g) and water (0.2 mL) were added and the reaction mixture was stirred for 20 h at room temperature. For workup, the reaction mixture was poured onto ethyl acetate (50 mL) and the ethyl acetate solution was extracted with a saturated aq. $NaHCO_3$-solution (50 mL). The organic layer was extracted with water (20 mL) and the solvent was evaporated. The residue was dissolved in ethyl acetate/isopropanol 9:1 (20 mL) and the solution was clear filtered over a 0.45 micrometer filter. The solvent was evaporated under reduced pressure and the residue was dried in vacuo at 45° C. to obtain 100 mg crude product. HPLC analysis indicated the presence of ca. 95.6 area % Compound A and ca. 4.4 area % Compound A-dehydrate.

What is claimed is:

1. A compound selected from a compound of any one of Formulae II, III, VI, VIII and XXV:

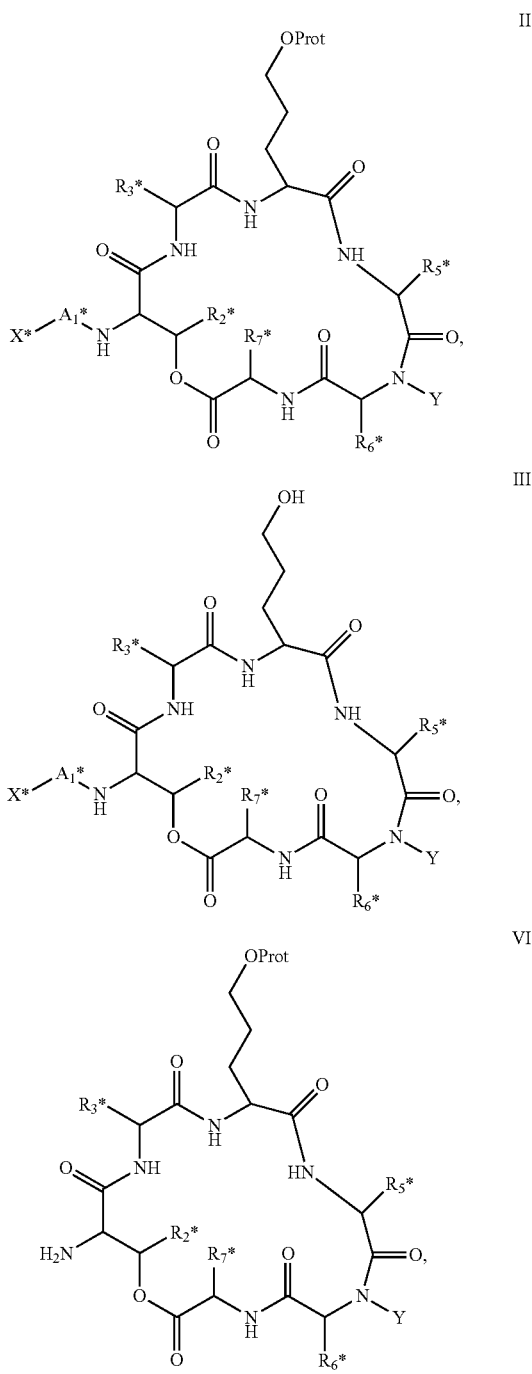

-continued

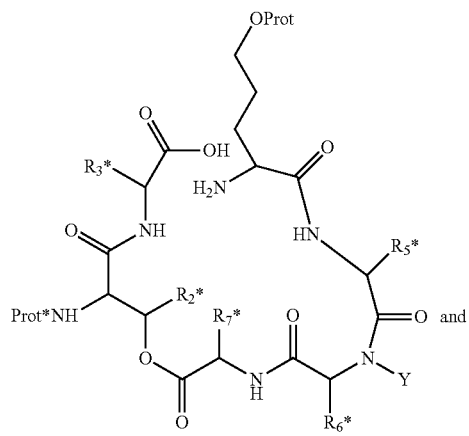

VIII

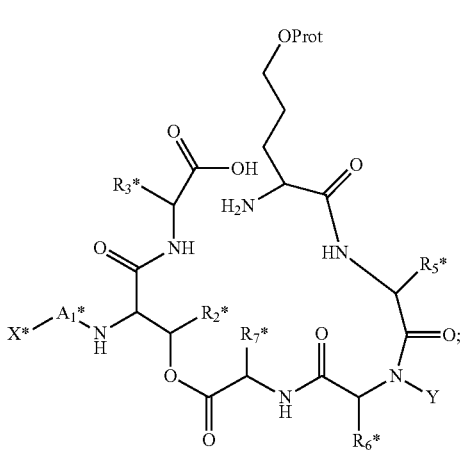

XXV wherein Prot is a protecting group, and Prot* is a protecting group that can be cleaved off selectively without affecting the other protecting groups present and which is a $C_3$-$C_8$alk-2-enyloxycarbonyl moiety;

Y is hydrogen or $C_{1-8}$-alkyl and X*, $A_1$*, $R_2$*, $R_3$*, $R_5$*, $R_6$*, and $R_7$* correspond to X, $A_1$, $R_2$, $R_3$, $R_5$, $R_6$, and $R_7$ respectively, wherein $A_l$ is a bivalent moiety of an amino acid with a terminal carboxy or carbamoyl group, and is bound at its right hand side in formula I via a carbonyl to the rest of the molecule; or is $C_{1-8}$-alkanoyl or phosphorylated hydroxy-$C_{1-8}$-alkanoyl;

X is bound via an N of $A_1$ and is acyl, or is absent if $A_1$ is $C_{1-8}$-alkanoyl or phosphorylated hydroxy-$C_{1-8}$-alkanoyl;

$R_2$ is $C_{1-8}$-alkyl;

$R_3$ is the side chain of leucine, isoleucine or valine;

$R_5$ is the side chain of phenylalanine, leucine, isoleucine or valine;

$R_6$ is the side chain of a hydroxy amino acid; and $R_7$ is the side chain of the amino acid leucine, isoleucine or valine; however with the proviso that reactive functional groups on these moieties are present in unprotected or protected form, or a salt thereof.

2. The compound according to claim 1 of Formula II:

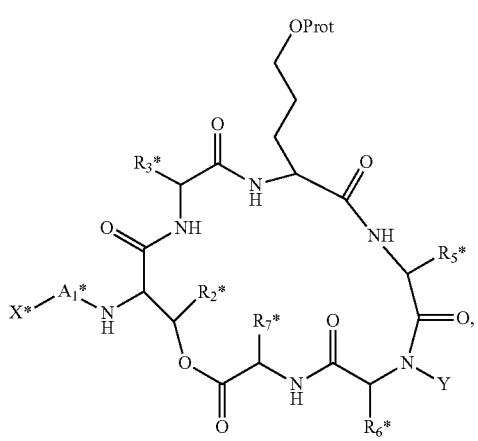

II or a salt thereof.

3. The compound according to claim 1, having Formula II,

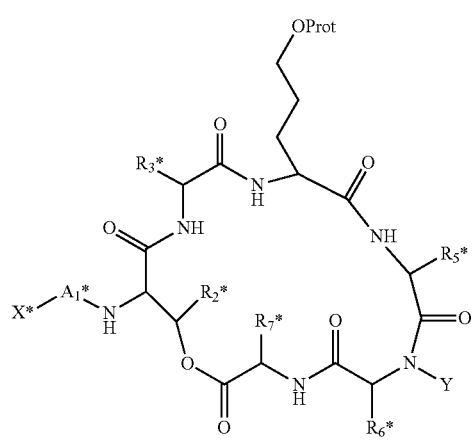

II wherein Prot is a protecting group, Y is methyl and X*, $A_1$*, $R_2$*, $R_3$*, $R_5$*, $R_6$*, and $R_7$* correspond to X, $A_1$, $R_2$, $R_3$, $R_5$, $R_6$, and $R_7$ respectively, wherein $A_l$ is a bivalent radical of L-glutamine bound via the carbonyl of its α-carboxyl group to the amino group at the right of $A_1$ in formula I and via its α-amino group to X, or is 2S-(2-hydroxy-3-phosphonooxy)-propionyl;

$R_2$ is methyl;

$R_3$ is isopropyl or isobutyl;

$R_5$ is sec-butyl or benzyl;

$R_6$ is 4-hydroxybenzyl;

$R_7$ is isopropyl or sec-butyl, and

X is acetyl or isobutyryl, or is absent if $A_l$ is 2S-(2-hydroxy-3-phosphonooxy)-propionyl, however with the proviso that reactive functional groups on these moieties are present in unprotected or protected form, or a salt thereof.

4. The compound according to claim 1 having Formula III,

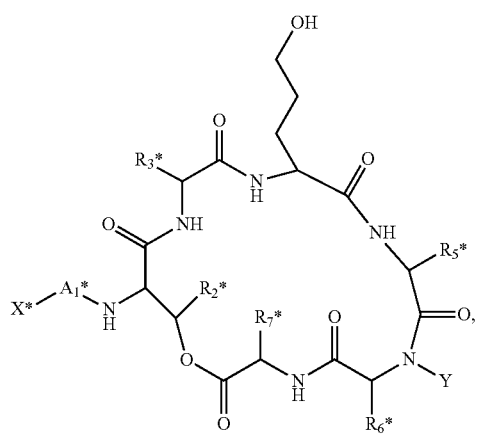

or a salt thereof.

5. The compound according to claim 1 having Formula III,

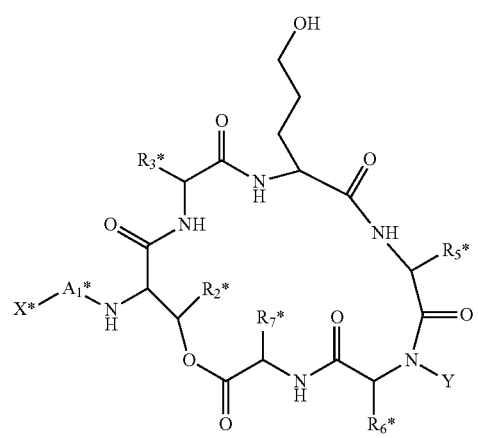

wherein

Y is methyl and X*, $A_1$*, $R_2$*, $R_3$*, $R_5$*, $R_6$*, and $R_7$* correspond to X, $A_1$, $R_2$, $R_3$, $R_5$, $R_6$, and $R_7$ respectively, wherein $A_1$ is a bivalent radical of L-glutamine bound via the carbonyl of its α-carboxyl group to the amino group at the right of $A_1$ in formula I and via its α-amino group to X, or is 2S-(2-hydroxy-3-phosphonooxy)-propionyl;

$R_2$ is methyl;

$R_3$ is isopropyl or isobutyl;

$R_5$ is sec-butyl or benzyl;

$R_6$ is 4-hydroxybenzyl;

$R_7$ is isopropyl or sec-butyl; and

X is acetyl or isobutyryl, or is absent if $A_1$ is 2S-(2-hydroxy-3-phosphonooxy)-propionyl, however with the proviso that reactive functional groups on these moieties are present in unprotected or protected form, or a salt thereof.

6. The compound according to claim 1 having Formula VI

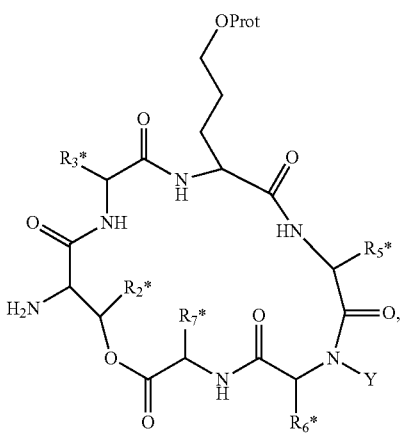

or a salt thereof.

7. The compound according to claim 1 having Formula VI

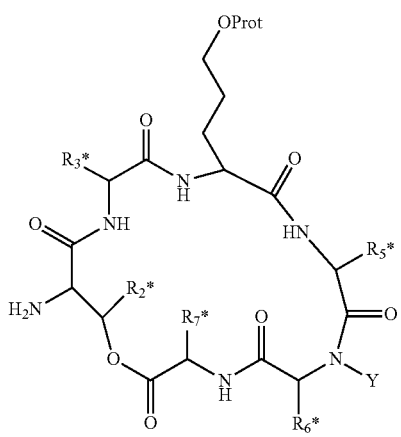

wherein Prot is a protecting group, Y is methyl and $R_2$*, $R_3$*, $R_5$*, $R_6$*, and $R_7$* correspond to $R_2$, $R_3$, $R_5$, $R_6$, and $R_7$ respectively, wherein $R_2$ is methyl;

$R_3$ is isopropyl or isobutyl;

$R_5$ is sec-butyl or benzyl;

$R_6$ is 4-hydroxybenzyl; and $R_7$ is isopropyl or sec-butyl, however with the proviso that reactive functional groups on these moieties are present in unprotected or protected form, or a salt thereof.

8. The compound of claim 1 having Formula VIII

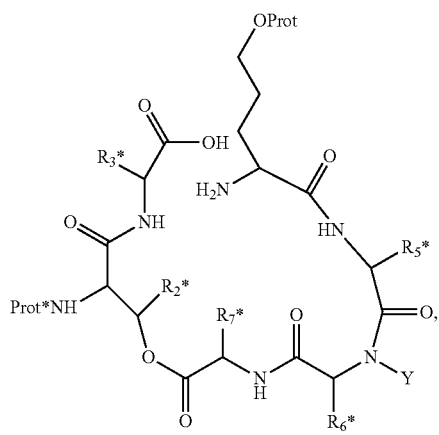

or a salt thereof.

9. The compound according to claim 1 having Formula VIII

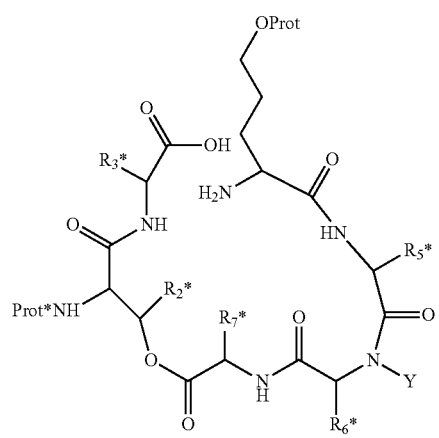

wherein Prot is a protecting group, Prot* is a protecting group that can be cleaved off selectively without affecting the other protecting groups present, Y is methyl and $R_2^*$, $R_3^*$, $R_5^*$, $R_6^*$, and $R_7^*$ correspond to $R_2$, $R_3$, $R_5$, $R_6$, and $R_7$ respectively, wherein $R_2$ is methyl;
$R_3$ is isopropyl or isobutyl;
$R_5$ is sec-butyl or benzyl;
$R_6$ is 4-hydroxybenzyl; and
$R_7$ is isopropyl or sec-butyl,
however with the proviso that reactive functional groups on these moieties are present in unprotected or protected form, or a salt thereof.

10. The compound according to claim 1 having Formula XXV

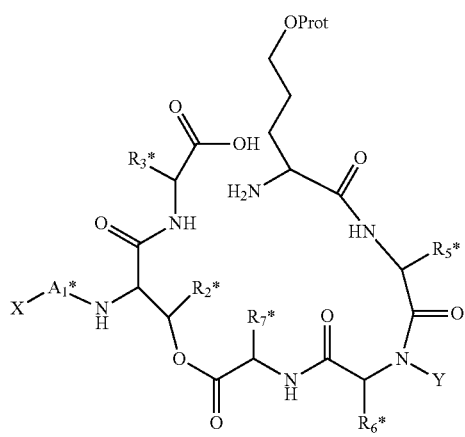

or a salt thereof.

11. The compound according to claim 1 having Formula XXV

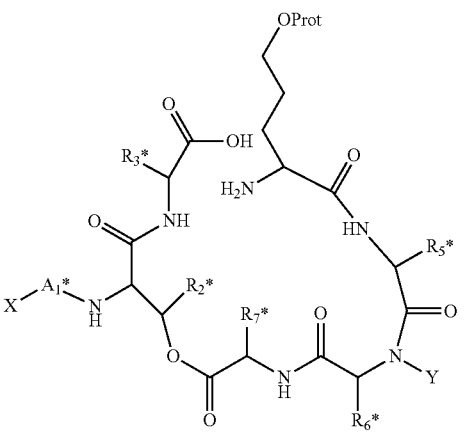

wherein Prot is a protecting group, Y is methyl and X*, $A_1^*$, $R_2^*$, $R_3^*$, $R_5^*$, $R_6^*$, and $R_7^*$ correspond to X, $A_1$, $R_2$, $R_3$, $R_5$, $R_6$, and $R_7$ respectively, wherein $A_1$ is a bivalent radical of L-glutamine bound via the carbonyl of its α-carboxyl group to the amino group at the right of $A_1$ in formula I and via its α-amino group to X, or is 2S-(2-hydroxy-3-phosphonooxy)-propionyl;

$R_2$ is methyl;
$R_3$ is isopropyl or isobutyl;
$R_5$ is sec-butyl or benzyl;
$R_6$ is 4-hydroxybenzyl;
$R_7$ is isopropyl or sec-butyl, and
X is acetyl or isobutyryl, or is absent if $A_1$ is 2S-(2-hydroxy-3-phosphonooxy)-propionyl, however with the proviso that reactive functional groups on these moieties are present in unprotected or protected form, or a salt thereof.

12. The compound according to claim 1 selected from
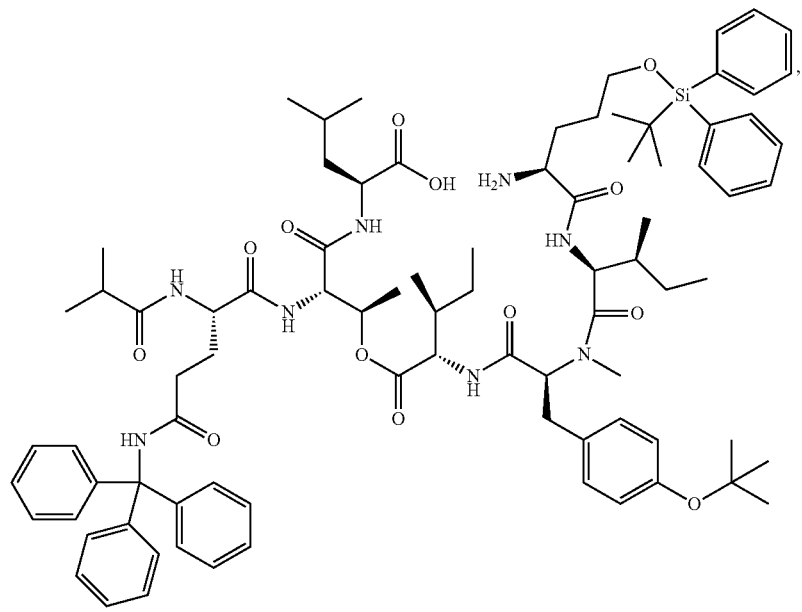
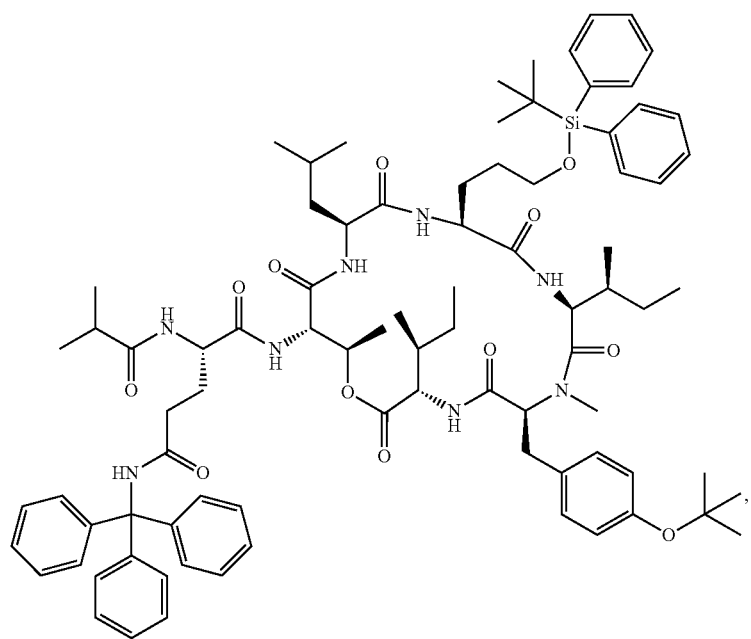

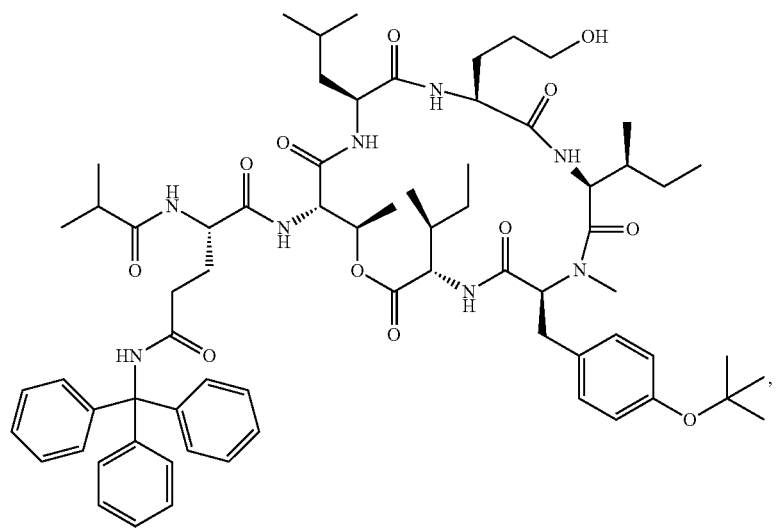
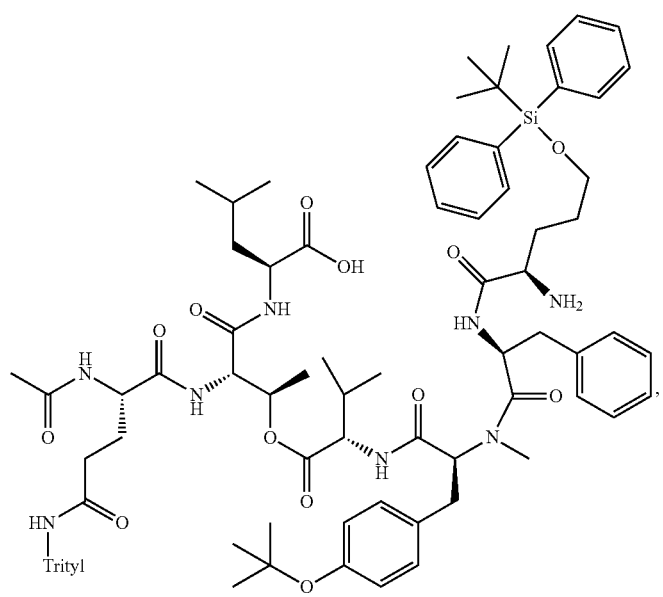

-continued
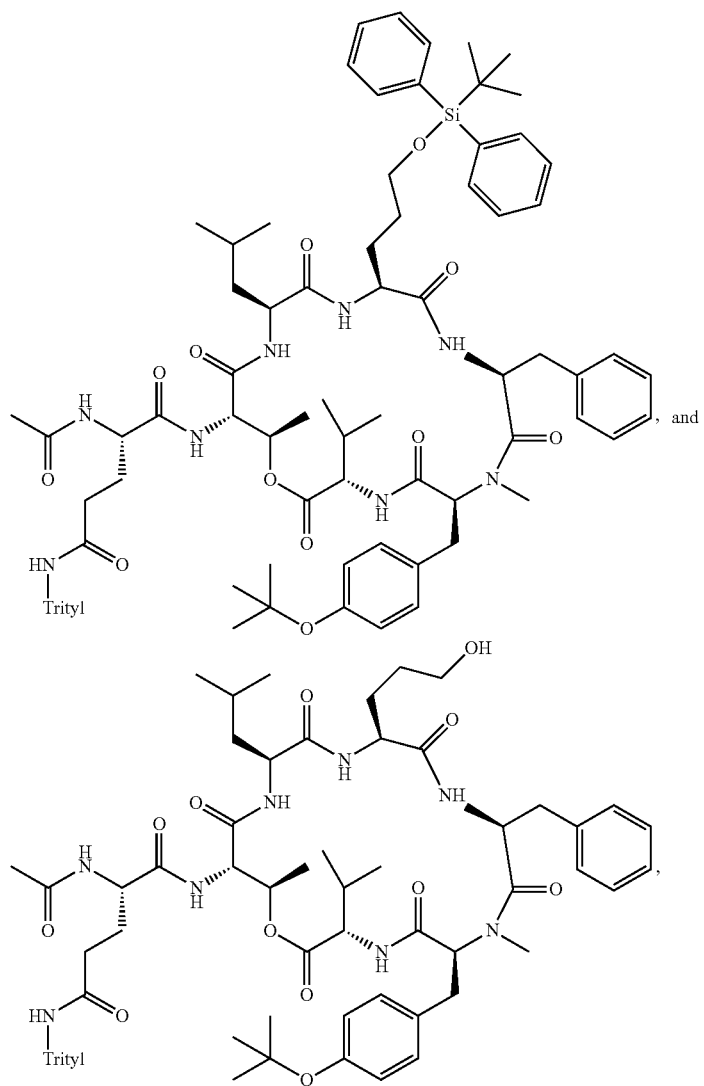
45
or a salt thereof.
* * * * *